(12) United States Patent
Spence et al.

(10) Patent No.: US 8,142,493 B2
(45) Date of Patent: Mar. 27, 2012

(54) METHOD OF HEART VALVE REPAIR

(75) Inventors: Paul A. Spence, Louisville, KY (US);
Walter Bruszewski, San Francisco, CA (US); Ed McNamara, Chelmsford, MA (US); Mark Maguire, San Mateo, CA (US)

(73) Assignee: Mitralign, Inc., Tewksbury, MA (US)

( * ) Notice: Subject to any disclaimer, the term of this patent is extended or adjusted under 35 U.S.C. 154(b) by 400 days.

(21) Appl. No.: 12/177,554

(22) Filed: Jul. 22, 2008

(65) Prior Publication Data
US 2008/0275503 A1  Nov. 6, 2008

Related U.S. Application Data

(62) Division of application No. 10/948,922, filed on Sep. 24, 2004, now Pat. No. 7,431,726.

(60) Provisional application No. 60/554,314, filed on Mar. 18, 2004, provisional application No. 60/531,855, filed on Dec. 23, 2003.

(51) Int. Cl.
*A61F 2/24* (2006.01)
(52) U.S. Cl. ...................... 623/2.36; 623/904
(58) Field of Classification Search ......... 623/2.36–2.38
See application file for complete search history.

(56) References Cited

U.S. PATENT DOCUMENTS

| | | | |
|---|---|---|---|
| 2,143,910 A | 1/1939 | Didusch | |
| 3,674,014 A | 7/1972 | Tillander | |
| 3,794,041 A | 2/1974 | Frei et al. | |
| 3,841,521 A | 10/1974 | Jarvik | |
| 3,986,493 A | 10/1976 | Hendren, III | |
| 4,042,979 A | 8/1977 | Angell | |
| 4,055,861 A | 11/1977 | Carpentier et al. | |
| 4,258,705 A | 3/1981 | Sorensen et al. | |
| 4,369,787 A | 1/1983 | Lasner et al. | |
| 4,489,446 A | 12/1984 | Reed | |
| 4,532,926 A | 8/1985 | O'Holla | |
| 4,809,713 A | 3/1989 | Grayzel | |
| 4,917,698 A | 4/1990 | Carpentier et al. | |
| 4,945,912 A | 8/1990 | Langberg | |
| 5,016,353 A | 5/1991 | Iten | |
| 5,041,129 A | 8/1991 | Hayhurst et al. | |
| 5,041,130 A | 8/1991 | Cosgrove et al. | |
| 5,061,277 A | 10/1991 | Carpentier et al. | |
| 5,104,407 A | 4/1992 | Lam et al. | |
| 5,123,914 A | 6/1992 | Cope | |
| 5,171,232 A | 12/1992 | Castillo et al. | |

(Continued)

FOREIGN PATENT DOCUMENTS

EP  1016377 A2  7/2000

(Continued)

OTHER PUBLICATIONS

U.S. Patent and Trademark Office, International Search Report and Written Opinion in PCT Application No. PCT/US2008/056620, Oct. 15, 2008.

(Continued)

*Primary Examiner* — Suzette J Gherbi
(74) *Attorney, Agent, or Firm* — Leason Ellis LLP

(57) ABSTRACT

Catheter based systems and methods for securing tissue including the annulus of a mitral valve. The systems and methods employ catheter based techniques and devices to plicate tissue and perform an annuloplasty.

12 Claims, 76 Drawing Sheets

U.S. PATENT DOCUMENTS

| | | |
|---|---|---|
| 5,201,880 A | 4/1993 | Wright et al. |
| 5,203,777 A | 4/1993 | Lee |
| 5,306,234 A | 4/1994 | Johnson |
| 5,306,296 A | 4/1994 | Wright et al. |
| 5,337,736 A | 8/1994 | Reddy |
| 5,360,444 A | 11/1994 | Kusuhara |
| 5,364,393 A | 11/1994 | Auth et al. |
| 5,429,131 A | 7/1995 | Scheinman et al. |
| 5,450,860 A | 9/1995 | O'Connor |
| 5,452,513 A | 9/1995 | Zinnbauer et al. |
| 5,464,023 A | 11/1995 | Viera |
| 5,480,388 A | 1/1996 | Zadini et al. |
| 5,545,178 A | 8/1996 | Kensey et al. |
| 5,565,122 A | 10/1996 | Zinnbauer et al. |
| 5,571,215 A | 11/1996 | Sterman et al. |
| 5,593,424 A | 1/1997 | Northrup |
| 5,607,471 A | 3/1997 | Seguin et al. |
| 5,623,943 A | 4/1997 | Hackett et al. |
| 5,626,590 A | 5/1997 | Wilk |
| 5,640,955 A | 6/1997 | Ockuly et al. |
| 5,669,919 A | 9/1997 | Sanders et al. |
| 5,674,279 A | 10/1997 | Wright et al. |
| 5,682,906 A | 11/1997 | Sterman et al. |
| 5,690,656 A | 11/1997 | Cope et al. |
| 5,706,827 A | 1/1998 | Ehr et al. |
| 5,716,367 A | 2/1998 | Koike et al. |
| 5,716,397 A | 2/1998 | Myers |
| 5,716,399 A | 2/1998 | Love |
| 5,776,080 A | 7/1998 | Thome et al. |
| 5,776,189 A | 7/1998 | Khalid |
| 5,797,939 A | 8/1998 | Yoon |
| 5,813,996 A | 9/1998 | St. Germain et al. |
| 5,824,066 A | 10/1998 | Gross |
| 5,827,300 A | 10/1998 | Fleega |
| 5,829,447 A | 11/1998 | Stevens et al. |
| 5,830,224 A | 11/1998 | Cohn et al. |
| 5,851,185 A | 12/1998 | Berns |
| 5,860,920 A | 1/1999 | McGee et al. |
| 5,868,733 A | 2/1999 | Ockuly et al. |
| 5,888,240 A | 3/1999 | Carpentier et al. |
| 5,906,579 A | 5/1999 | Vander Salm et al. |
| 5,911,720 A | 6/1999 | Bourne et al. |
| 5,928,224 A | 7/1999 | Laufer |
| 5,931,818 A | 8/1999 | Werp et al. |
| 5,944,738 A | 8/1999 | Amplatz et al. |
| 5,967,984 A | 10/1999 | Chu et al. |
| 5,980,515 A | 11/1999 | Tu |
| 5,984,939 A | 11/1999 | Yoon |
| 6,015,414 A | 1/2000 | Werp et al. |
| 6,042,581 A | 3/2000 | Ryan et al. |
| 6,050,472 A | 4/2000 | Shibata |
| 6,050,936 A | 4/2000 | Schweich, Jr. et al. |
| 6,068,637 A | 5/2000 | Popov et al. |
| 6,068,648 A | 5/2000 | Cole et al. |
| 6,071,292 A | 6/2000 | Makower et al. |
| 6,099,460 A | 8/2000 | Denker |
| 6,102,945 A | 8/2000 | Campbell |
| 6,126,647 A | 10/2000 | Posey et al. |
| RE36,974 E | 11/2000 | Bonutti |
| 6,159,234 A | 12/2000 | Bonutti et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,183 A | 12/2000 | Kuehn et al. |
| 6,173,199 B1 | 1/2001 | Gabriel |
| 6,190,353 B1 | 2/2001 | Makower et al. |
| 6,197,017 B1 | 3/2001 | Brock et al. |
| 6,206,895 B1 | 3/2001 | Levinson |
| 6,210,432 B1 | 4/2001 | Solem et al. |
| 6,231,587 B1 | 5/2001 | Makower |
| 6,267,781 B1 | 7/2001 | Tu |
| 6,269,819 B1 | 8/2001 | Oz et al. |
| 6,285,903 B1 | 9/2001 | Rosenthal et al. |
| 6,287,317 B1 | 9/2001 | Makower et al. |
| 6,298,257 B1 | 10/2001 | Hall et al. |
| 6,306,133 B1 | 10/2001 | Tu et al. |
| 6,312,447 B1 | 11/2001 | Grimes |
| 6,319,263 B1 | 11/2001 | Levinson |
| 6,332,089 B1 | 12/2001 | Acker et al. |
| 6,332,893 B1 | 12/2001 | Mortier et al. |
| 6,352,543 B1 | 3/2002 | Cole |
| 6,385,472 B1 | 5/2002 | Hall et al. |
| 6,401,720 B1 | 6/2002 | Stevens et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,447,522 B2 | 9/2002 | Gambale et al. |
| 6,461,366 B1 | 10/2002 | Seguin |
| 6,500,184 B1 | 12/2002 | Chan et al. |
| 6,524,303 B1 | 2/2003 | Garibaldi |
| 6,530,952 B2 | 3/2003 | Vesely |
| 6,537,198 B1 | 3/2003 | Vidlund et al. |
| 6,537,314 B2 | 3/2003 | Langberg et al. |
| 6,542,766 B2 | 4/2003 | Hall et al. |
| 6,544,230 B1 | 4/2003 | Flaherty et al. |
| 6,554,852 B1 | 4/2003 | Oberlander |
| 6,562,019 B1 | 5/2003 | Sell |
| 6,565,562 B1 | 5/2003 | Shah et al. |
| 6,589,208 B2 | 7/2003 | Ewers et al. |
| 6,594,517 B1 | 7/2003 | Nevo |
| 6,596,014 B2 | 7/2003 | Levinson et al. |
| 6,619,291 B2 | 9/2003 | Hlavka et al. |
| 6,626,919 B1 | 9/2003 | Swanstrom |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,655,386 B1 | 12/2003 | Makower et al. |
| 6,656,221 B2 | 12/2003 | Taylor et al. |
| 6,669,687 B1 | 12/2003 | Saadat |
| 6,669,707 B1 | 12/2003 | Swanstrom et al. |
| 6,676,702 B2 | 1/2004 | Mathis |
| 6,689,164 B1 | 2/2004 | Sequin |
| 6,699,263 B2 | 3/2004 | Cope |
| 6,702,825 B2 | 3/2004 | Frazier et al. |
| 6,702,826 B2 | 3/2004 | Liddicoat et al. |
| 6,718,985 B2 | 4/2004 | Hlavka et al. |
| 6,723,038 B1 | 4/2004 | Schroeder et al. |
| 6,730,112 B2 | 5/2004 | Levinson |
| 6,733,509 B2 | 5/2004 | Nobles et al. |
| 6,736,808 B1 | 5/2004 | Motamedi et al. |
| 6,746,472 B2 | 6/2004 | Frazier et al. |
| 6,764,500 B1 | 7/2004 | Muijs Van De Moer et al. |
| 6,769,434 B2 | 8/2004 | Liddicoat et al. |
| 6,793,618 B2 | 9/2004 | Schweich, Jr. et al. |
| 6,866,673 B2 | 3/2005 | Oren et al. |
| 6,913,608 B2 | 7/2005 | Liddicoat et al. |
| 6,921,407 B2 | 7/2005 | Nguyen et al. |
| 6,923,823 B1 | 8/2005 | Bartlett et al. |
| 6,942,694 B2 | 9/2005 | Liddicoat et al. |
| 6,945,978 B1 | 9/2005 | Hyde |
| 6,964,674 B1 | 11/2005 | Matsuura et al. |
| 6,964,683 B2 | 11/2005 | Kowalsky et al. |
| 7,004,958 B2 * | 2/2006 | Adams et al. ................ 606/219 |
| 7,037,334 B1 | 5/2006 | Hlavka et al. |
| 7,101,395 B2 | 9/2006 | Tremulis et al. |
| 7,166,127 B2 | 1/2007 | Spence et al. |
| 7,211,094 B2 | 5/2007 | Gannoe et al. |
| 2001/0005787 A1 | 6/2001 | Oz et al. |
| 2001/0039436 A1 | 11/2001 | Frazier et al. |
| 2001/0049492 A1 | 12/2001 | Frazier et al. |
| 2002/0013571 A1 | 1/2002 | Goldfarb et al. |
| 2002/0016628 A1 | 2/2002 | Langberg et al. |
| 2002/0026198 A1 | 2/2002 | Ockuly et al. |
| 2002/0026216 A1 | 2/2002 | Grimes |
| 2002/0029080 A1 | 3/2002 | Mortier et al. |
| 2002/0042621 A1 | 4/2002 | Liddicoat et al. |
| 2002/0072758 A1 | 6/2002 | Reo et al. |
| 2002/0087169 A1 | 7/2002 | Brock et al. |
| 2002/0087173 A1 | 7/2002 | Alferness et al. |
| 2002/0087178 A1 | 7/2002 | Nobles et al. |
| 2002/0095167 A1 | 7/2002 | Liddicoat et al. |
| 2002/0100485 A1 | 8/2002 | Stevens et al. |
| 2002/0103532 A1 | 8/2002 | Langberg et al. |
| 2002/0107531 A1 | 8/2002 | Schreck et al. |
| 2002/0128708 A1 | 9/2002 | Northrup, III et al. |
| 2002/0156526 A1 | 10/2002 | Hlavka et al. |
| 2002/0165535 A1 | 11/2002 | Lesh et al. |

| | | |
|---|---|---|
| 2002/0169359 A1 | 11/2002 | McCarthy et al. |
| 2002/0169502 A1 | 11/2002 | Mathis |
| 2002/0169504 A1 | 11/2002 | Alferness et al. |
| 2002/0173841 A1 | 11/2002 | Ortiz et al. |
| 2002/0183766 A1 | 12/2002 | Seguin |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0078671 A1 | 4/2003 | Lesniak et al. |
| 2003/0083538 A1 | 5/2003 | Adams et al. |
| 2003/0105474 A1 | 6/2003 | Bonutti |
| 2003/0105520 A1 | 6/2003 | Alferness et al. |
| 2003/0120340 A1 | 6/2003 | Liska et al. |
| 2003/0130730 A1 | 7/2003 | Cohn et al. |
| 2003/0144697 A1 | 7/2003 | Mathis et al. |
| 2003/0160721 A1 | 8/2003 | Gilboa et al. |
| 2003/0171776 A1 | 9/2003 | Adams et al. |
| 2003/0171806 A1 | 9/2003 | Mathis et al. |
| 2003/0199974 A1 | 10/2003 | Lee et al. |
| 2003/0208195 A1 | 11/2003 | Thompson et al. |
| 2003/0212453 A1 | 11/2003 | Mathis et al. |
| 2003/0220685 A1 | 11/2003 | Hlvka et al. |
| 2003/0233142 A1 | 12/2003 | Morales et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044364 A1 | 3/2004 | DeVries et al. |
| 2004/0049211 A1 | 3/2004 | Tremulis et al. |
| 2004/0092962 A1 | 5/2004 | Thornton et al. |
| 2004/0093023 A1 | 5/2004 | Allen et al. |
| 2004/0127983 A1 | 7/2004 | Mortier et al. |
| 2004/0133063 A1 | 7/2004 | McCarthy et al. |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0186486 A1 | 9/2004 | Roue et al. |
| 2004/0186566 A1 | 9/2004 | Hindichs et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0260317 A1 | 12/2004 | Bloom et al. |
| 2005/0033446 A1 | 2/2005 | Deem et al. |
| 2005/0049681 A1 | 3/2005 | Greenhalgh et al. |
| 2005/0055087 A1 | 3/2005 | Starksen |
| 2005/0055089 A1 | 3/2005 | Macoviak et al. |
| 2005/0065550 A1 | 3/2005 | Starksen et al. |
| 2005/0065601 A1 | 3/2005 | Lee et al. |
| 2005/0075723 A1 | 4/2005 | Schroeder et al. |
| 2005/0107810 A1 | 5/2005 | Morales et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0216039 A1 | 9/2005 | Lederman |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267571 A1 | 12/2005 | Spence et al. |
| 2006/0069429 A1 | 3/2006 | Spence et al. |
| 2006/0142756 A1 | 6/2006 | Davies et al. |
| 2006/0212045 A1 | 9/2006 | Schilling et al. |
| 2007/0010857 A1 | 1/2007 | Sugimoto et al. |
| 2007/0080188 A1 | 4/2007 | Spence et al. |
| 2007/0106310 A1 | 5/2007 | Goldin et al. |
| 2007/0112424 A1 | 5/2007 | Spence et al. |
| 2008/0228165 A1 | 9/2008 | Spence et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |

FOREIGN PATENT DOCUMENTS

| | | |
|---|---|---|
| WO | 9604852 A1 | 2/1996 |
| WO | 9900059 A1 | 1/1999 |
| WO | 0003759 A2 | 1/2000 |
| WO | 0044311 A2 | 8/2000 |
| WO | 0060995 A2 | 10/2000 |
| WO | 0067640 A2 | 11/2000 |
| WO | 0200099 A2 | 1/2002 |
| WO | 02051329 A1 | 7/2002 |
| WO | 02096275 A2 | 12/2002 |
| WO | 03001893 A2 | 1/2003 |
| WO | 03007796 A2 | 1/2003 |
| WO | 03053289 A1 | 7/2003 |
| WO | 2004045378 A2 | 6/2004 |
| WO | 2004112658 A1 | 12/2004 |
| WO | 2005011463 A2 | 2/2005 |
| WO | 2005013832 A1 | 2/2005 |
| WO | 2005025644 A2 | 3/2005 |
| WO | 2006064490 A1 | 6/2006 |
| WO | 2007005394 A1 | 1/2007 |

OTHER PUBLICATIONS

U.S. Patent and Trademark Office, International Search Report and Written Opinion in PCT Application No. PCT/US2008/080735, Dec. 17, 2008.

U.S. Patent and Trademark Office, Office Action in U.S. Appl. No. 10/949,133, Dec. 10, 2008.

U.S. Patent and Trademark Office, Final Office Action in U.S. Appl. No. 10/949,412, Jan. 15, 2009.

Cardiac Surgery Renaissance, Anatomical Landscape; Composite Profile of CABG and Valve Procedures, Apr. 25, 1996, Cardiology Roundtable Interviews.

F. Maisano et al., The Double-Orifice Technique as a Standardized Approach to Treat Mitral Regurgitation Due to Severe Myxomatous Disease: Surgical Technique, European Journal of Cardio-thoracis Surgery, 1998.

Douglas P. Zipes, MD et al., Ablation of Free Wall Accessory Pathways, Catheter Ablation of Arrhythmias, Chapter 8, 7 pgs., 1994.

Gsolt L. Nagy et al., Mitral Annuloplasty with a Suture Technique, European Journal of Cardio-thoracic Surgery 18, Aug. 15, 2000, 1 pg.

David L.S. Morales et al., Development of an Off Bypass Mitral Valve Repair, Department of Surgery, Columbia University, College of Physicians and Surgeons, New York, NY.

http://www.hsforum.com/vol2/issue2/1999-4963 tables.html.
http:/www.hsforum.com/vol2/issue2/1999-4963figures.html.
http://medtronic.com/cardiac/heartvalves/duran_band/.

European Patent Office, Supplementary Search Report in EP Application No. 02764186.9, Jan. 26, 2007.

European Patent Office, Supplementary Search Report in EP Application No. 02733960.5, Jan. 25, 2007.

European Patent Office, International Search Report and Written Opinion in PCT Application Serial No. PCT/US2006/024897, Dec. 6, 2006.

U.S. Patent and Trademark Office, Office Action in U.S. Appl. No. 10/948,922, Sep. 11, 2007.
U.S. Patent and Trademark Office, Office Action in U.S. Appl. No. 11/111,044, Jul. 16, 2007.
U.S. Patent and Trademark Office, Office Action in U.S. Appl. No. 10/622,207, May 21, 2007.
U.S. Patent and Trademark Office, Office Action in U.S. Appl. No. 10/622,207, Jul. 14, 2006.
U.S. Patent and Trademark Office, Office Action in U.S. Appl. No. 10/622,207, Aug. 23, 2005.
U.S. Patent and Trademark Office, Office Action in U.S. Appl. No. 10/622,207, Dec. 28, 2004.
European Patent Office, European Examination Report in Application Serial No. 02764186.9, Feb. 11, 2008.
U.S. Patent and Trademark Office, Office Action in U.S. Appl. No. 11/111,044, Feb. 26, 2008.
U.S. Patent and Trademark Office, Office Action in U.S. Appl. No. 10/948,923, Mar. 18, 2008.
U.S. Patent and Trademark Office, Office Action in U.S. Appl. No. 10/949,412, Aug. 6, 2008.
U.S. Patent and Trademark Office, Office Action in U.S. Appl. No. 10/689,872, Aug. 8, 2008.
U.S. Patent and Trademark Office, Office Action in U.S. Appl. No. 10/622,207, Apr. 11, 2008.

* cited by examiner

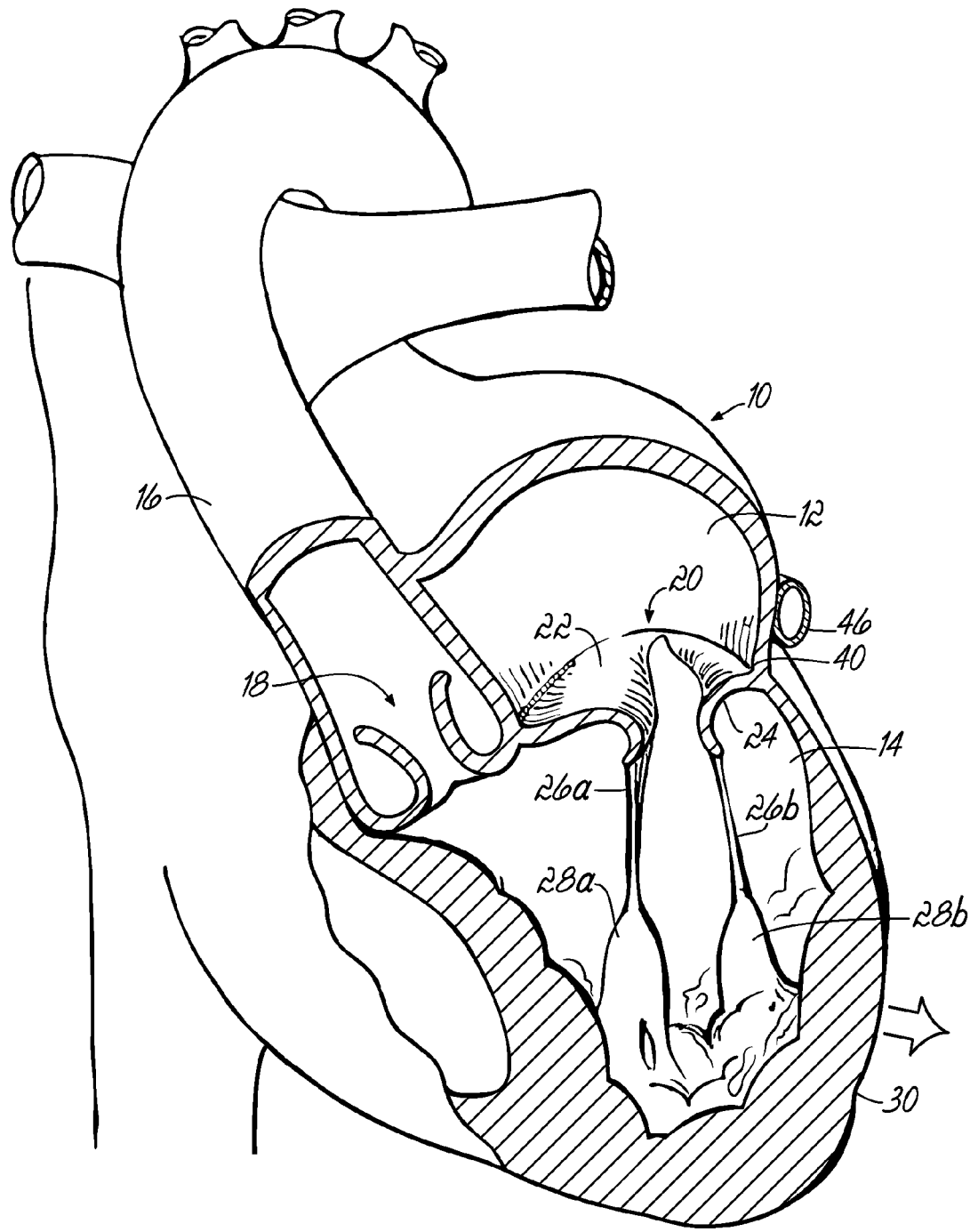
FIG. A

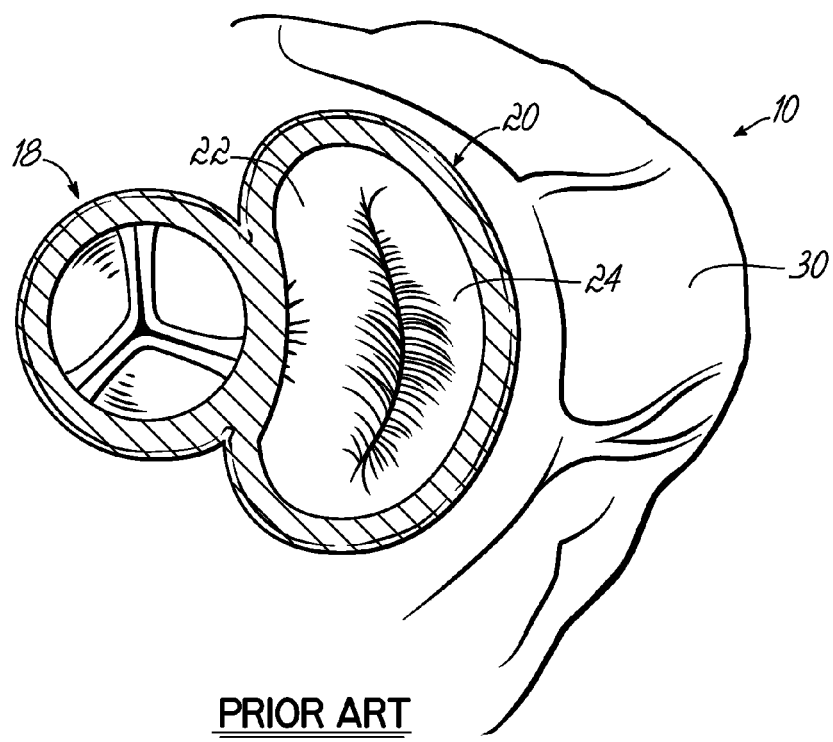
PRIOR ART
FIG. B
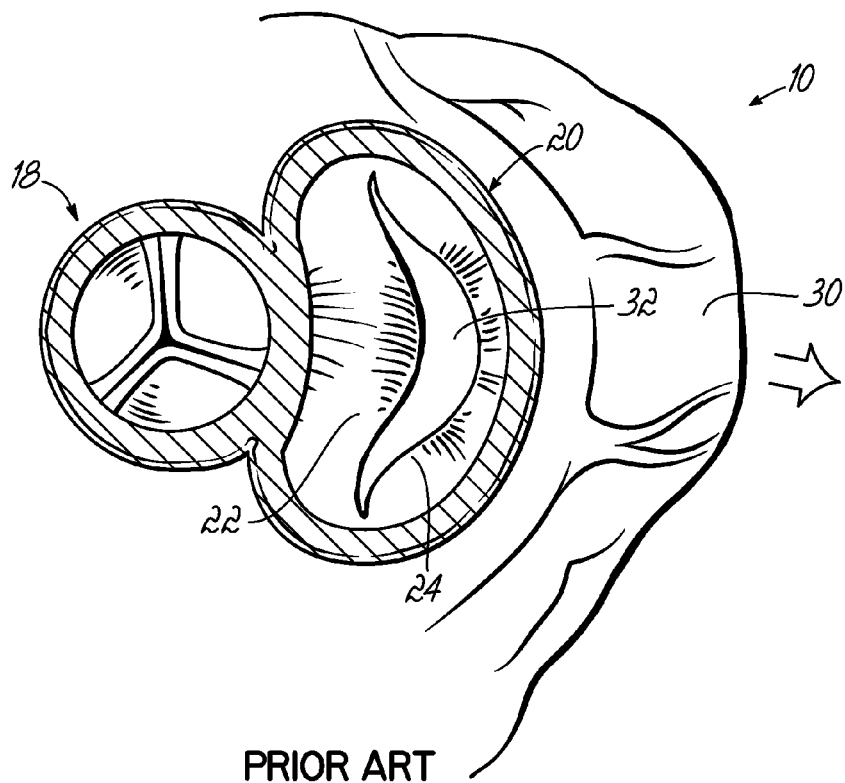
PRIOR ART
FIG. C

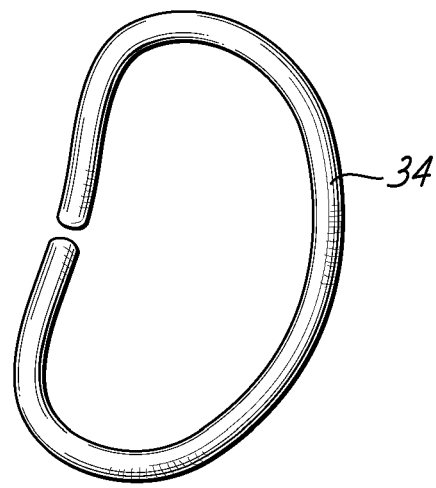
PRIOR ART
FIG. D
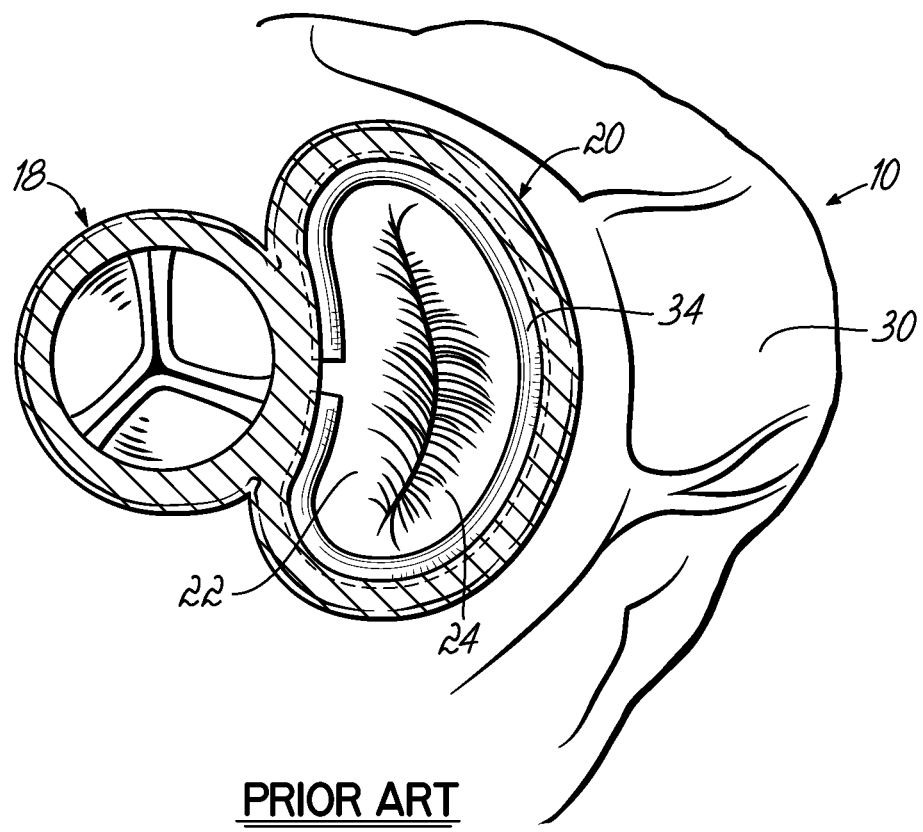
PRIOR ART
FIG. E

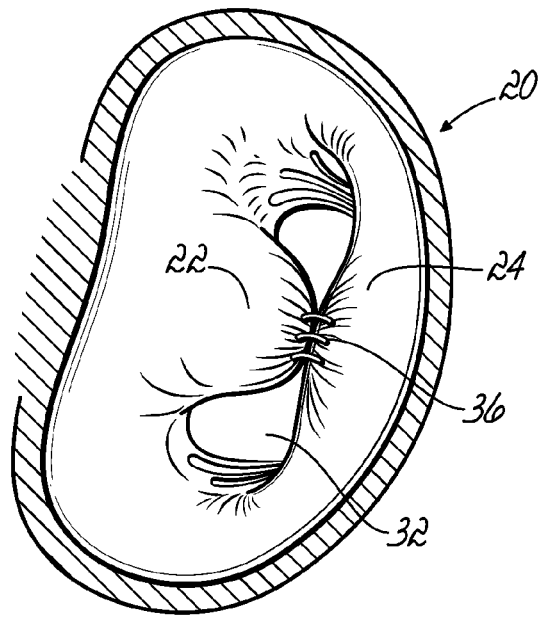
PRIOR ART
FIG. F
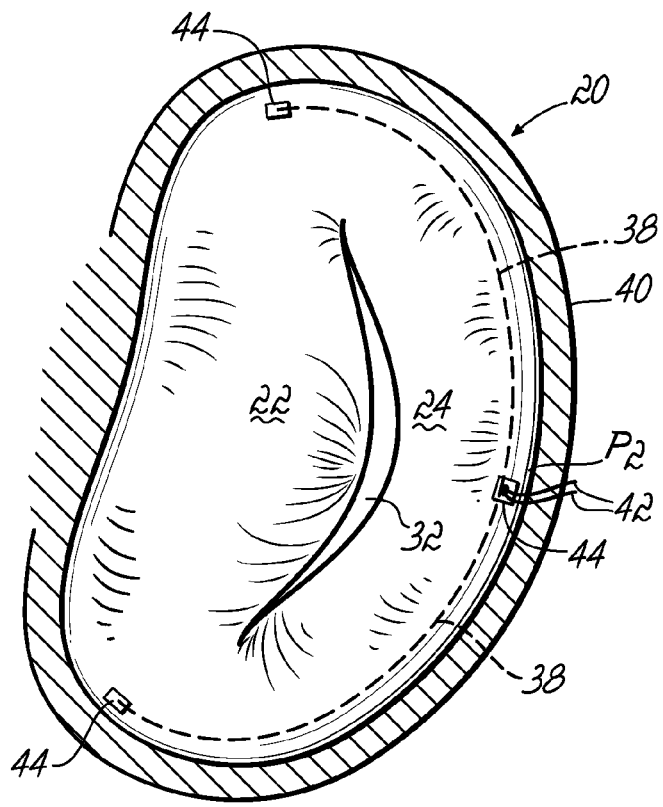
PRIOR ART
FIG. G

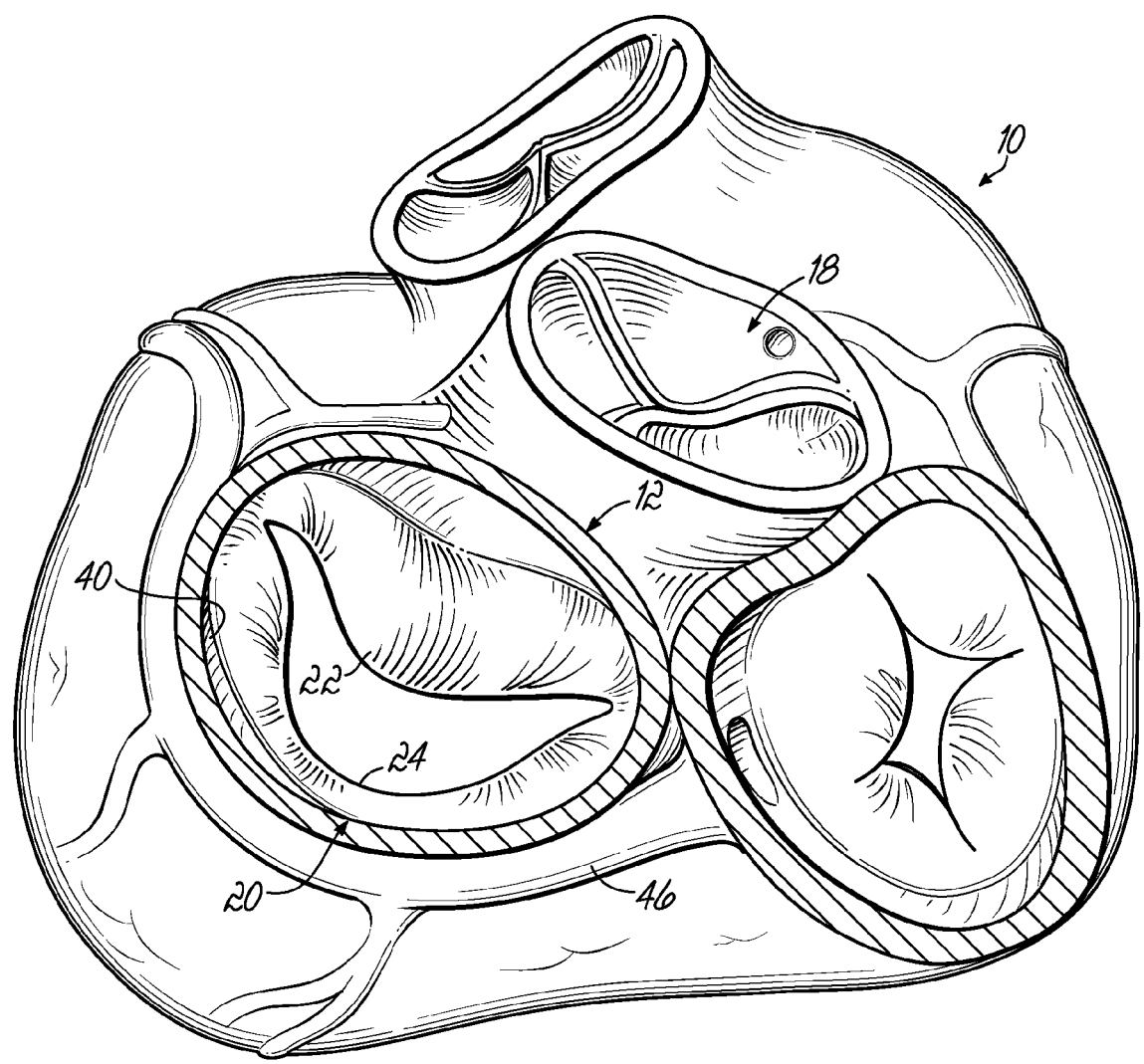
FIG. H

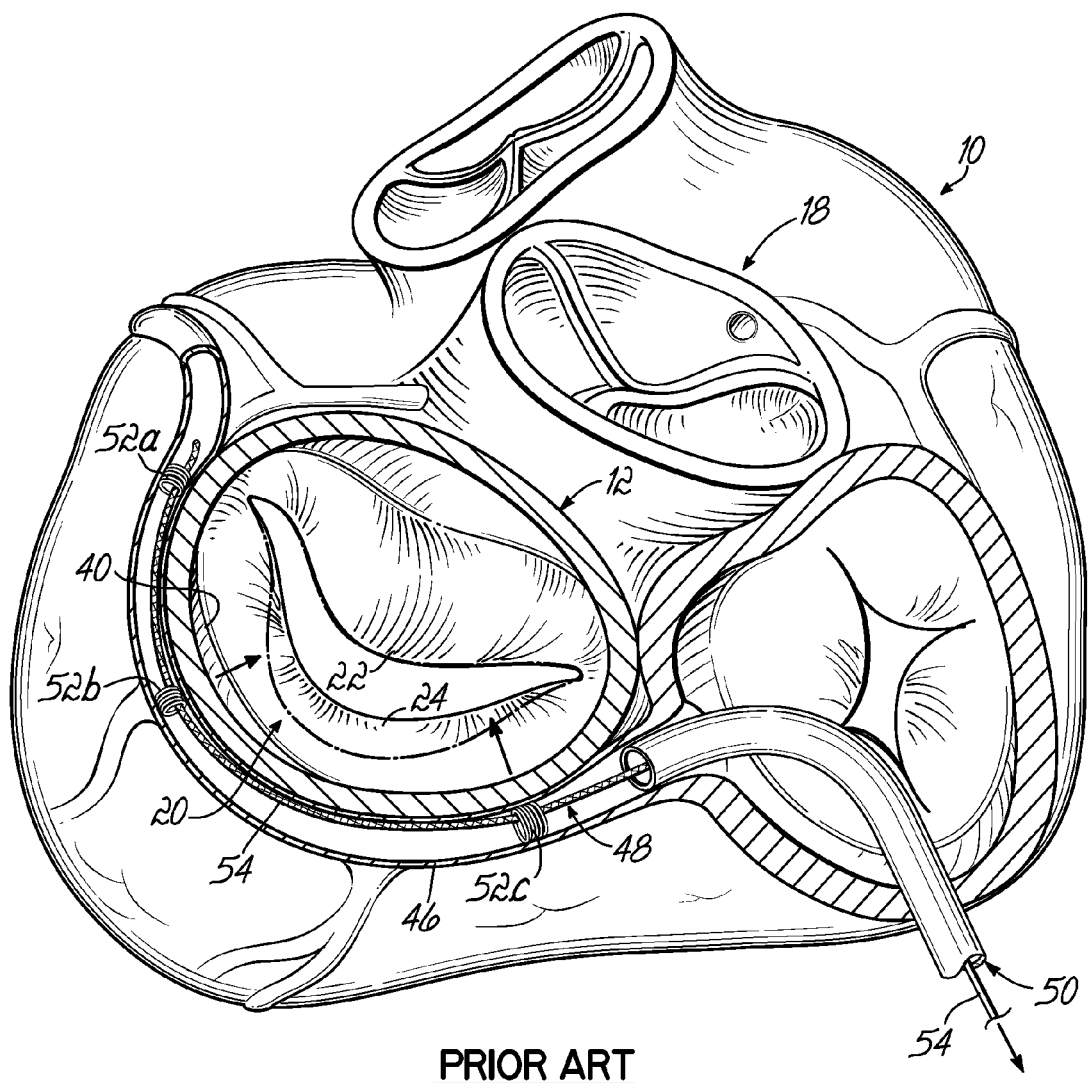
PRIOR ART
FIG. I

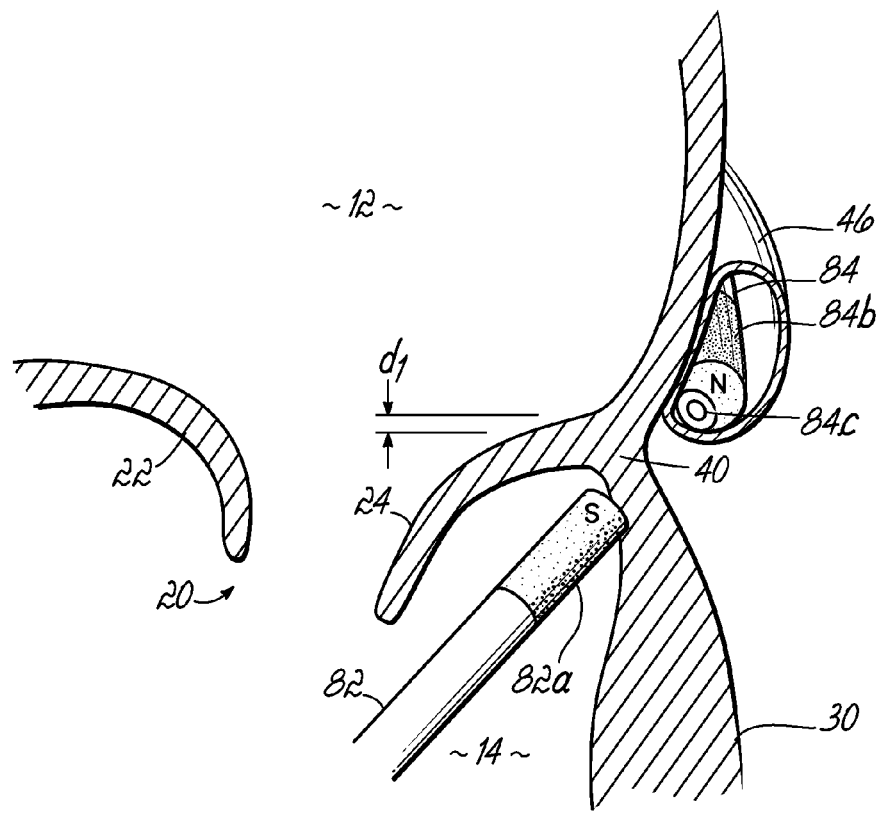
FIG. 7A
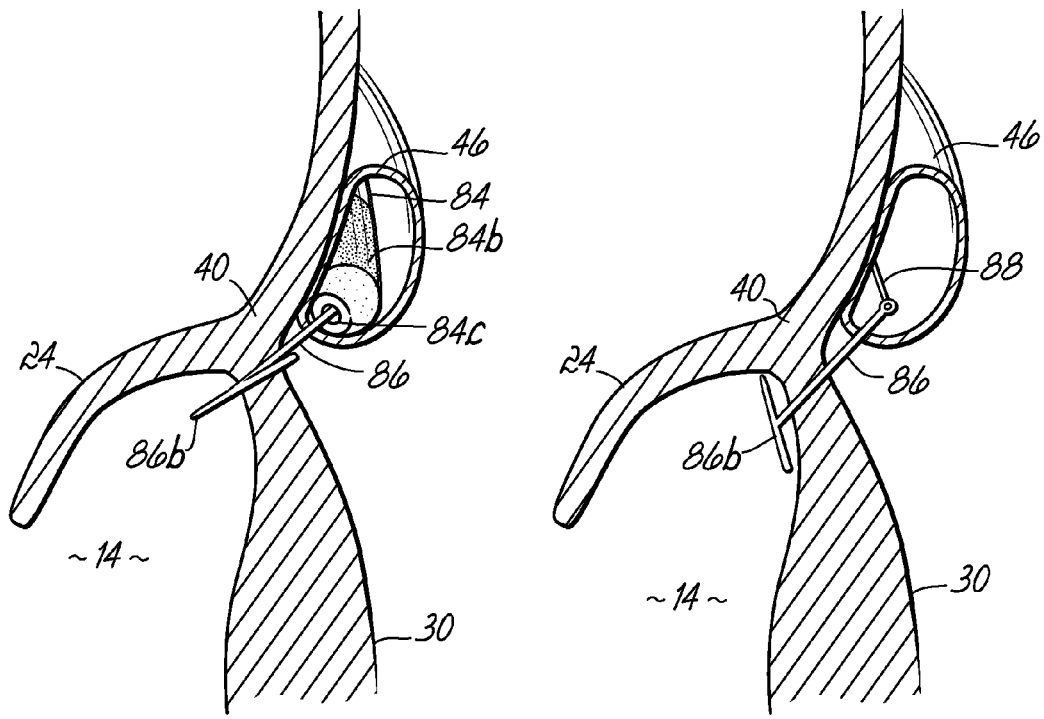
FIG. 7B
FIG. 7C

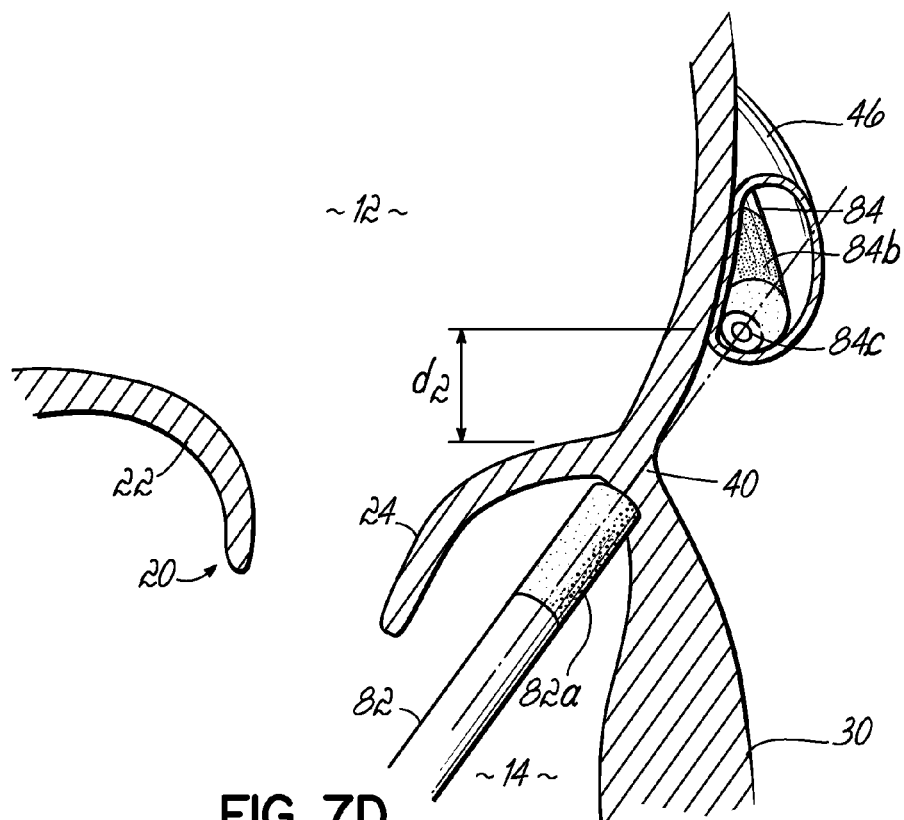
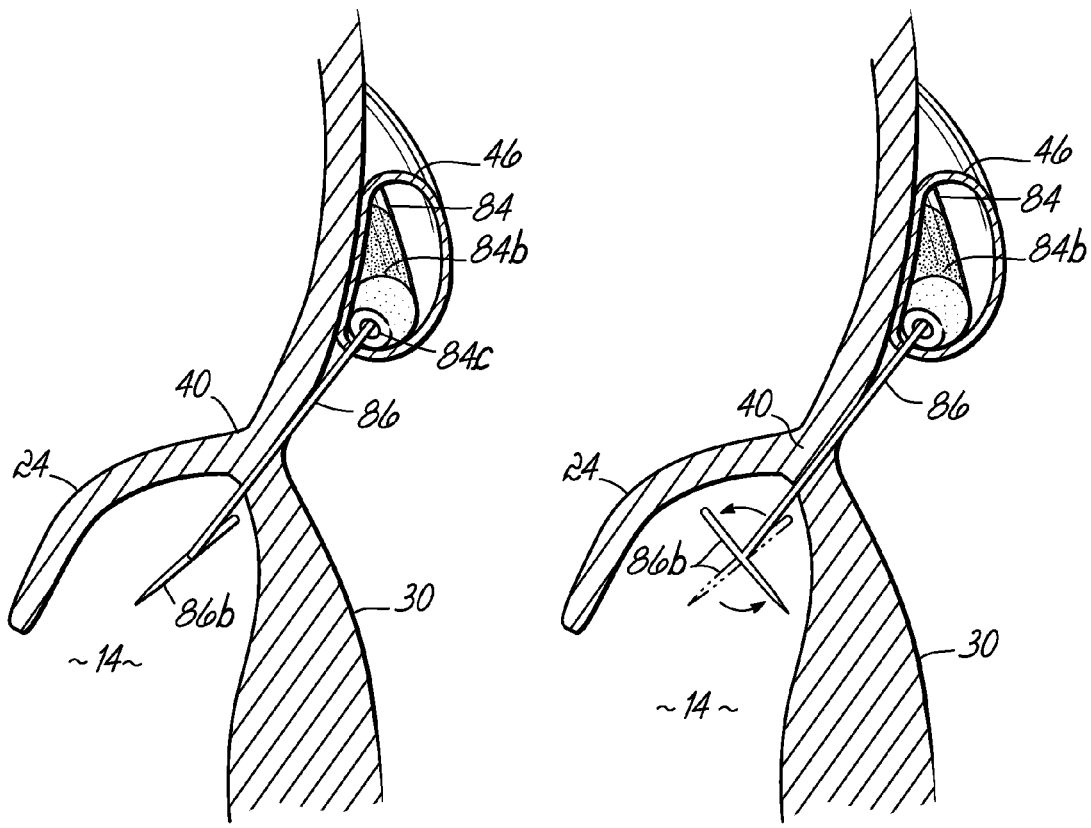
FIG. 7D
FIG. 7E  FIG. 7F

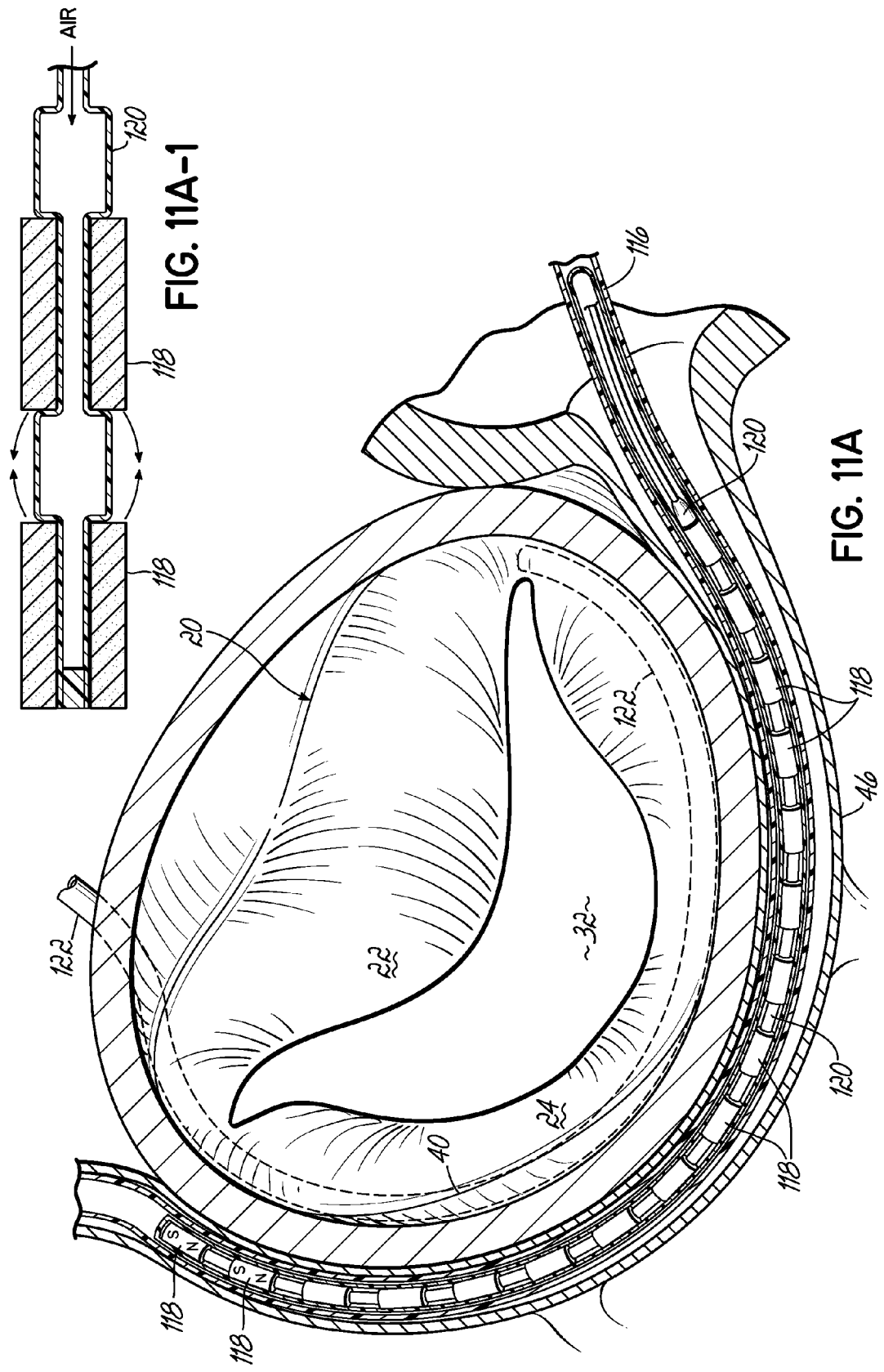

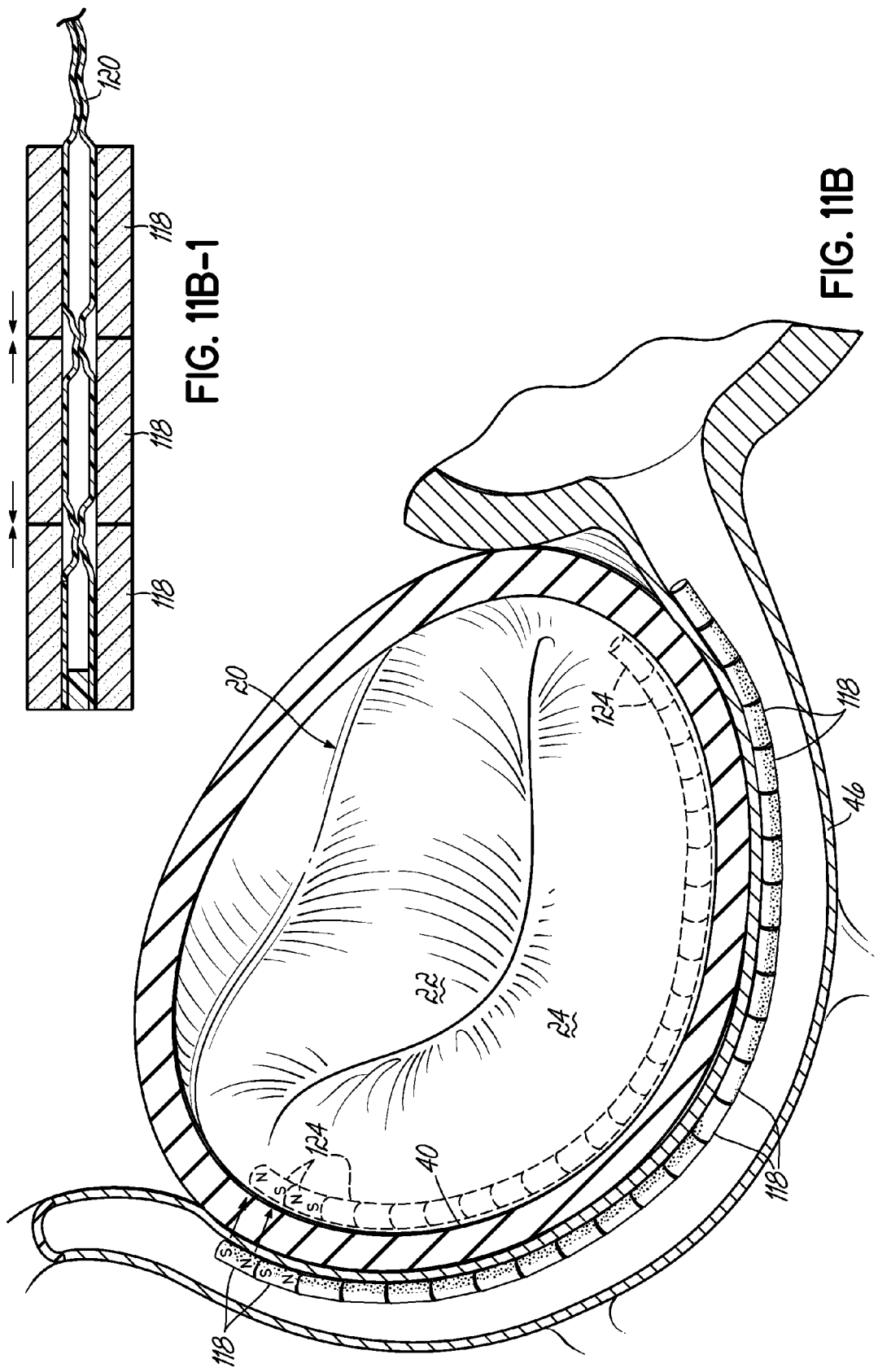

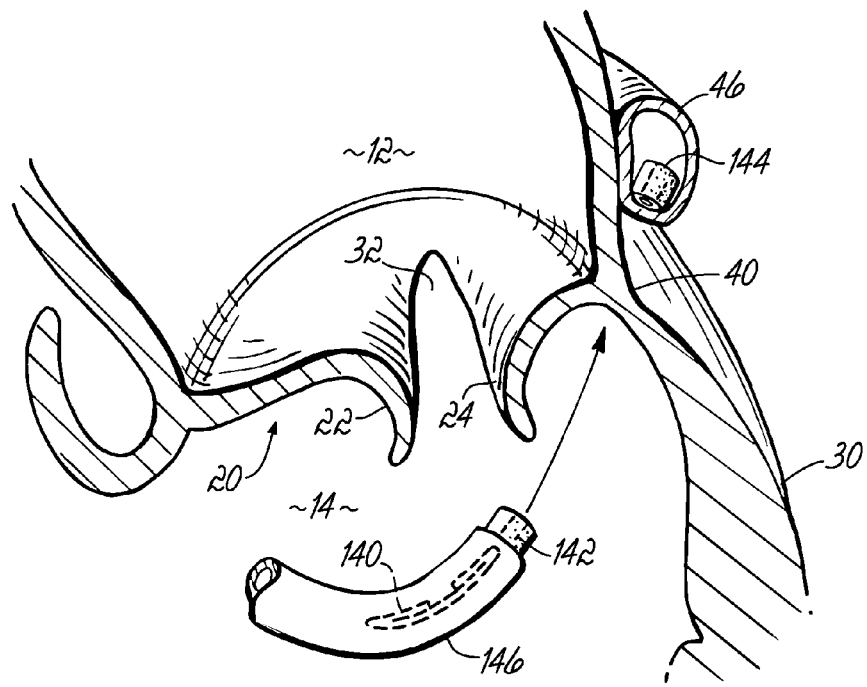
FIG. 15A
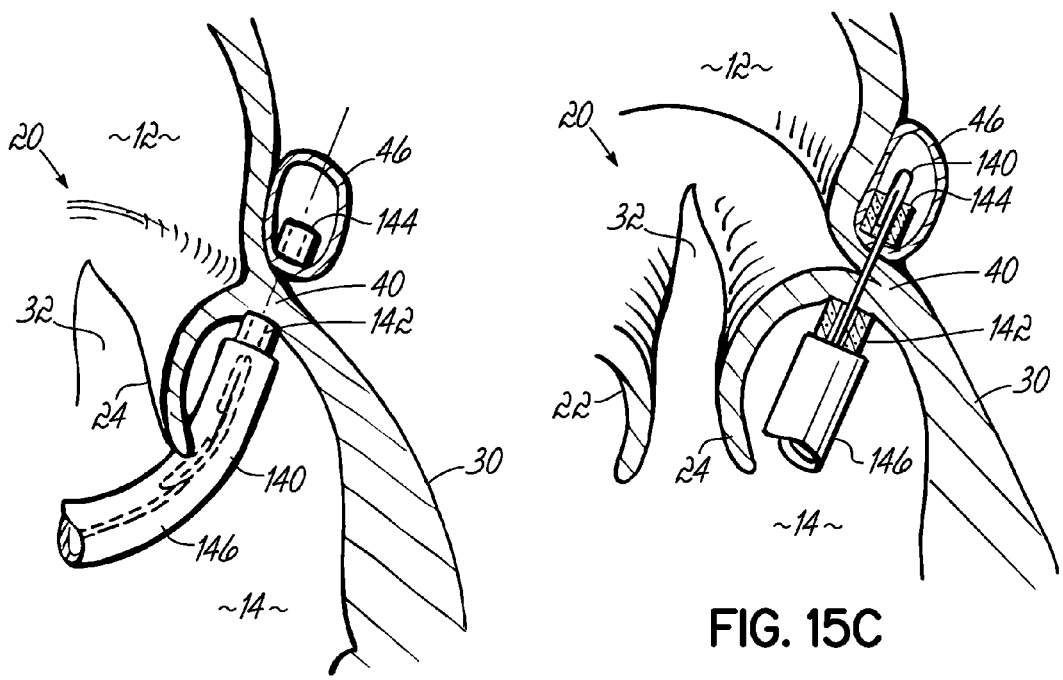
FIG. 15B
FIG. 15C

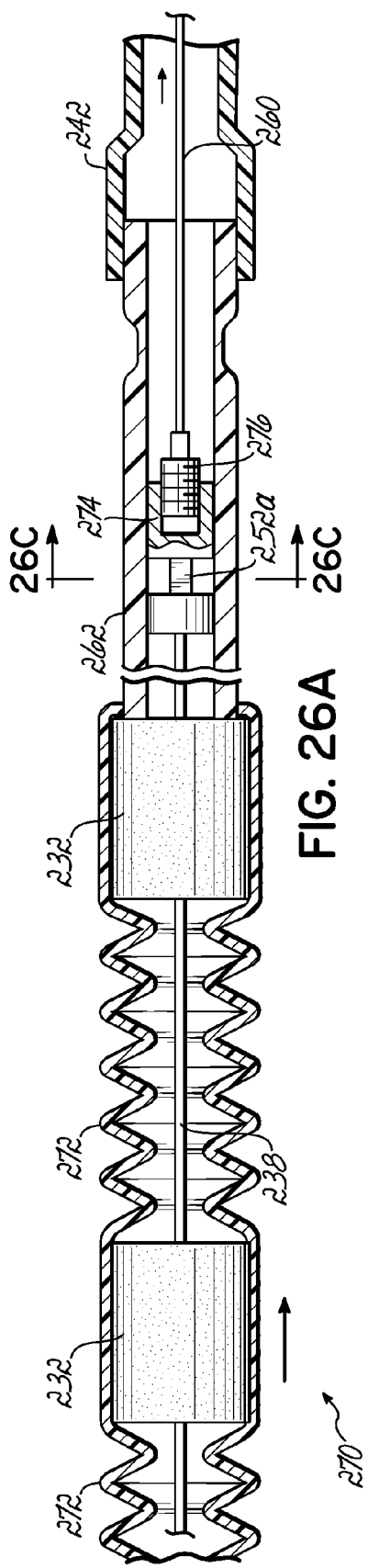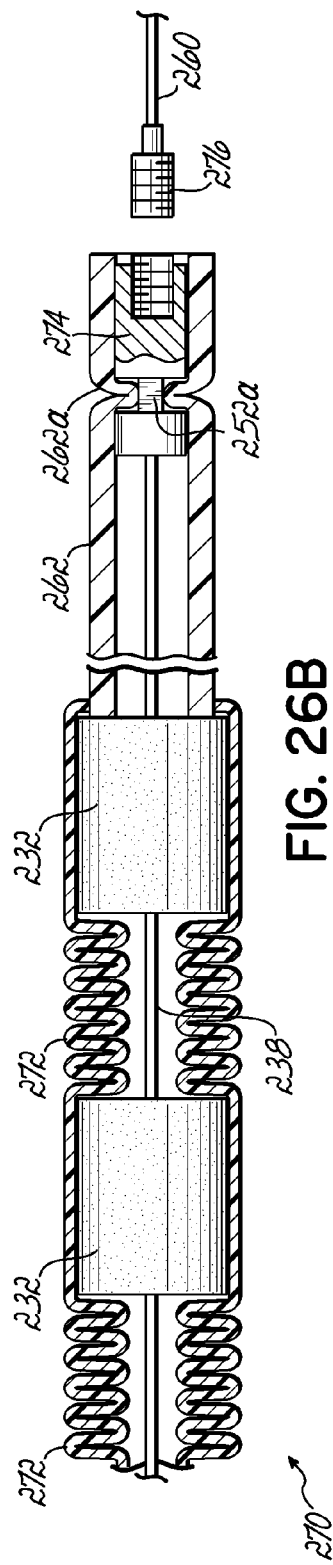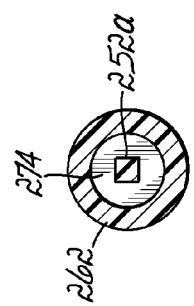
FIG. 26A
FIG. 26B
FIG. 26C

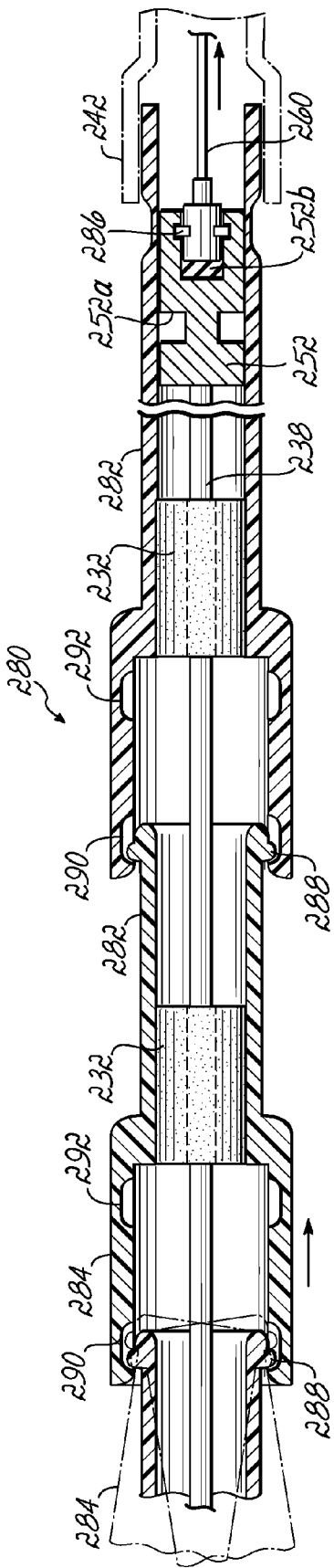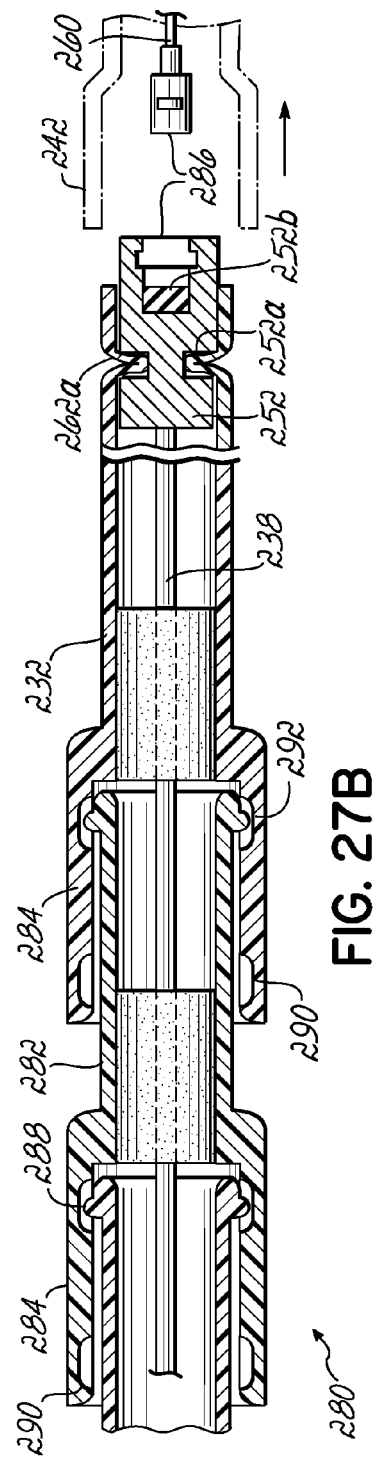
FIG. 27A
FIG. 27B

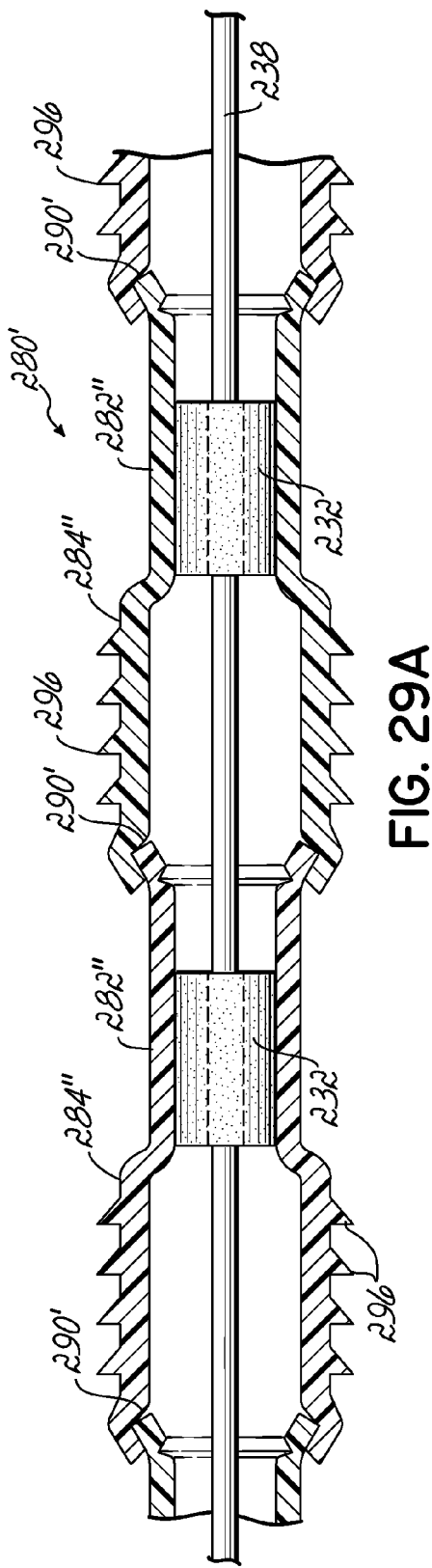
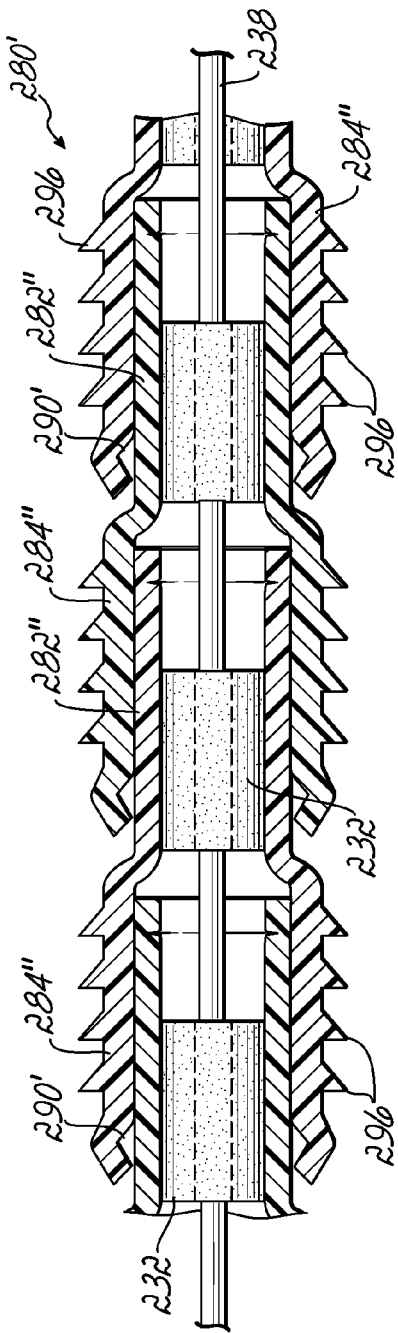
FIG. 29A
FIG. 29B

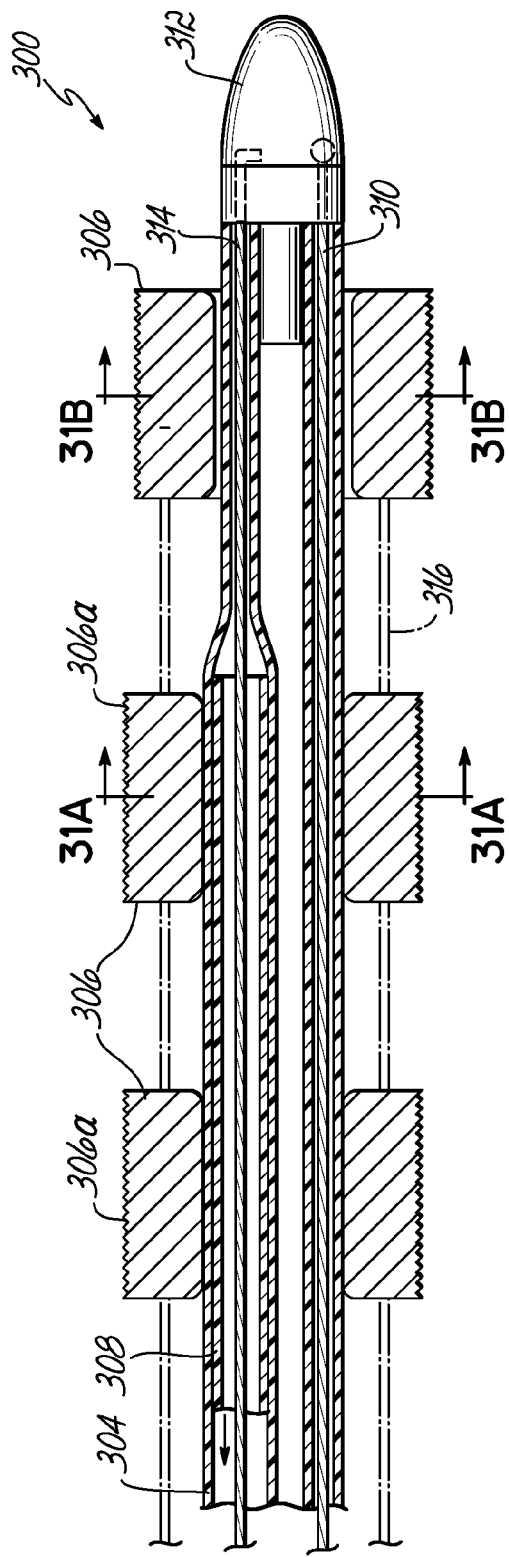
FIG. 30
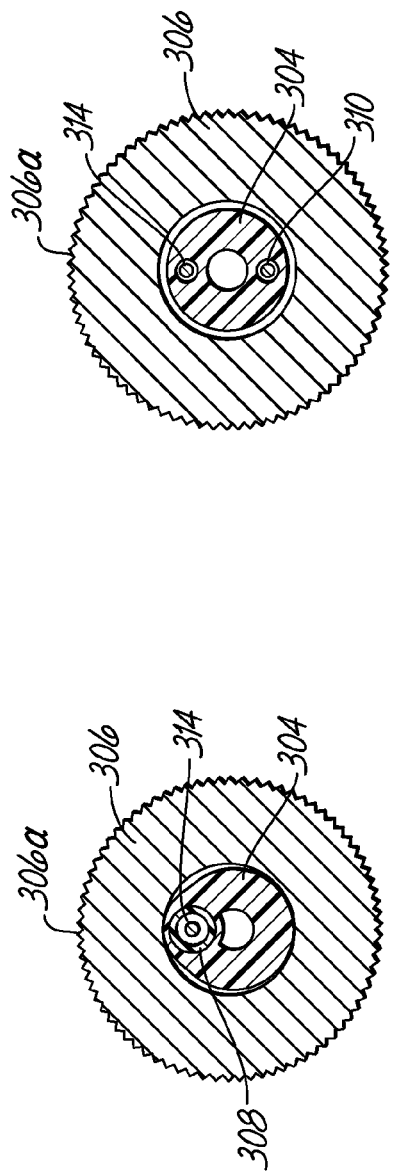
FIG. 31B
FIG. 31A

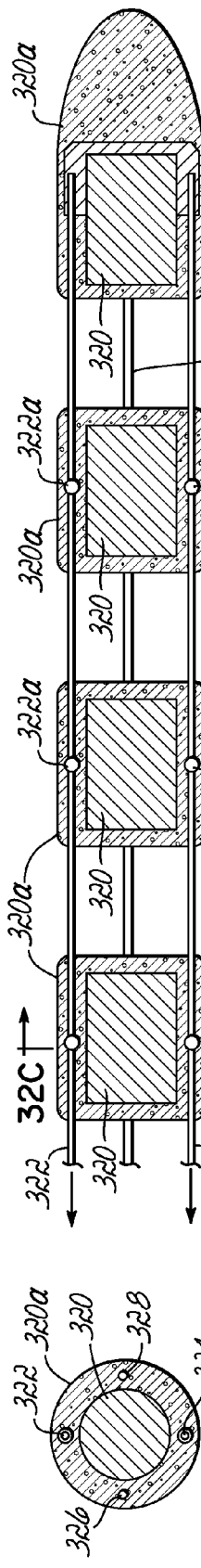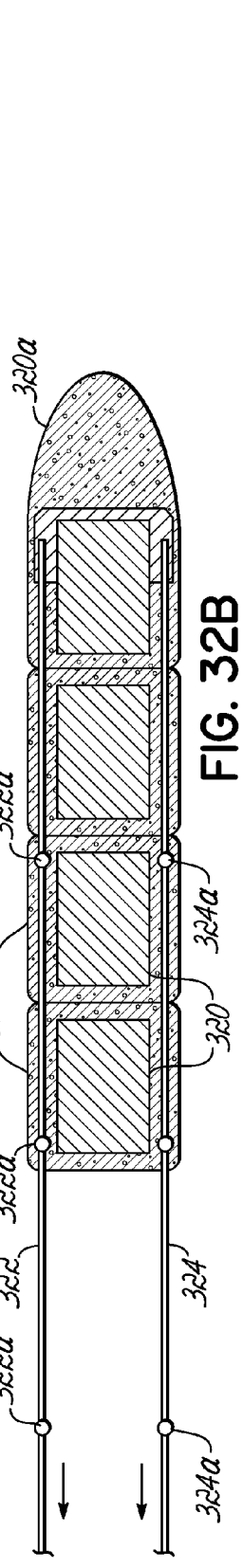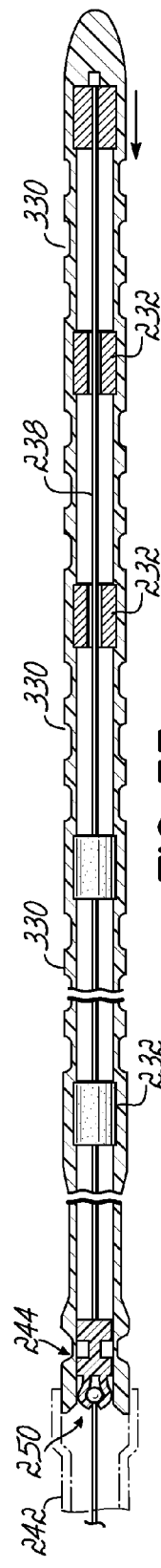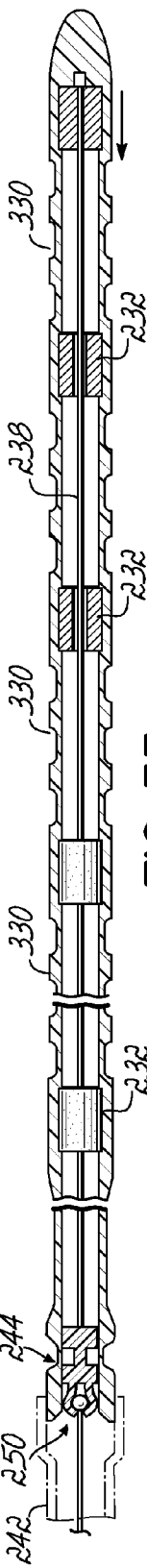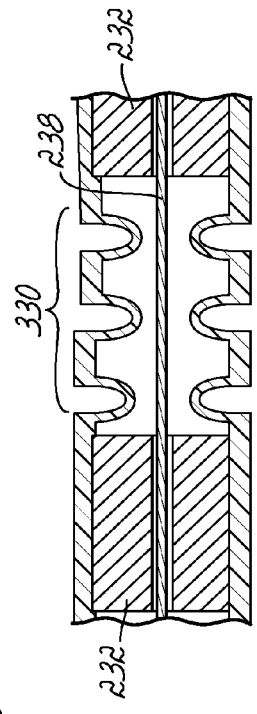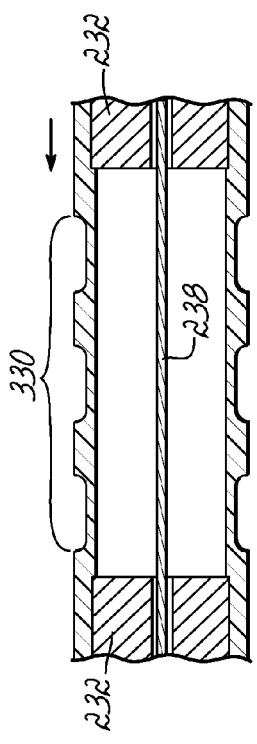

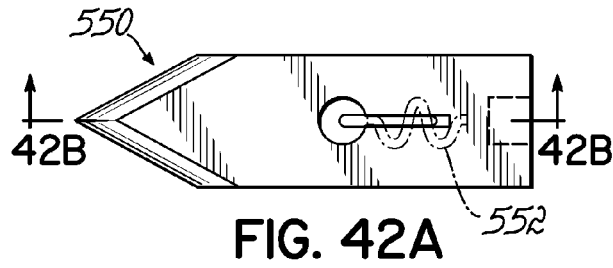
FIG. 42A
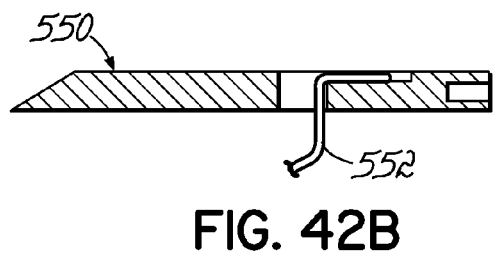
FIG. 42B
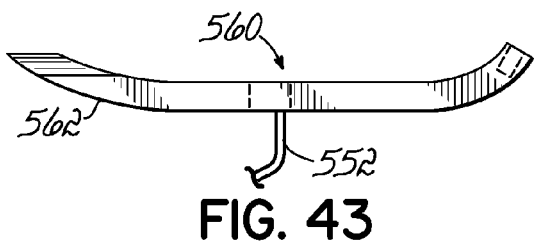
FIG. 43
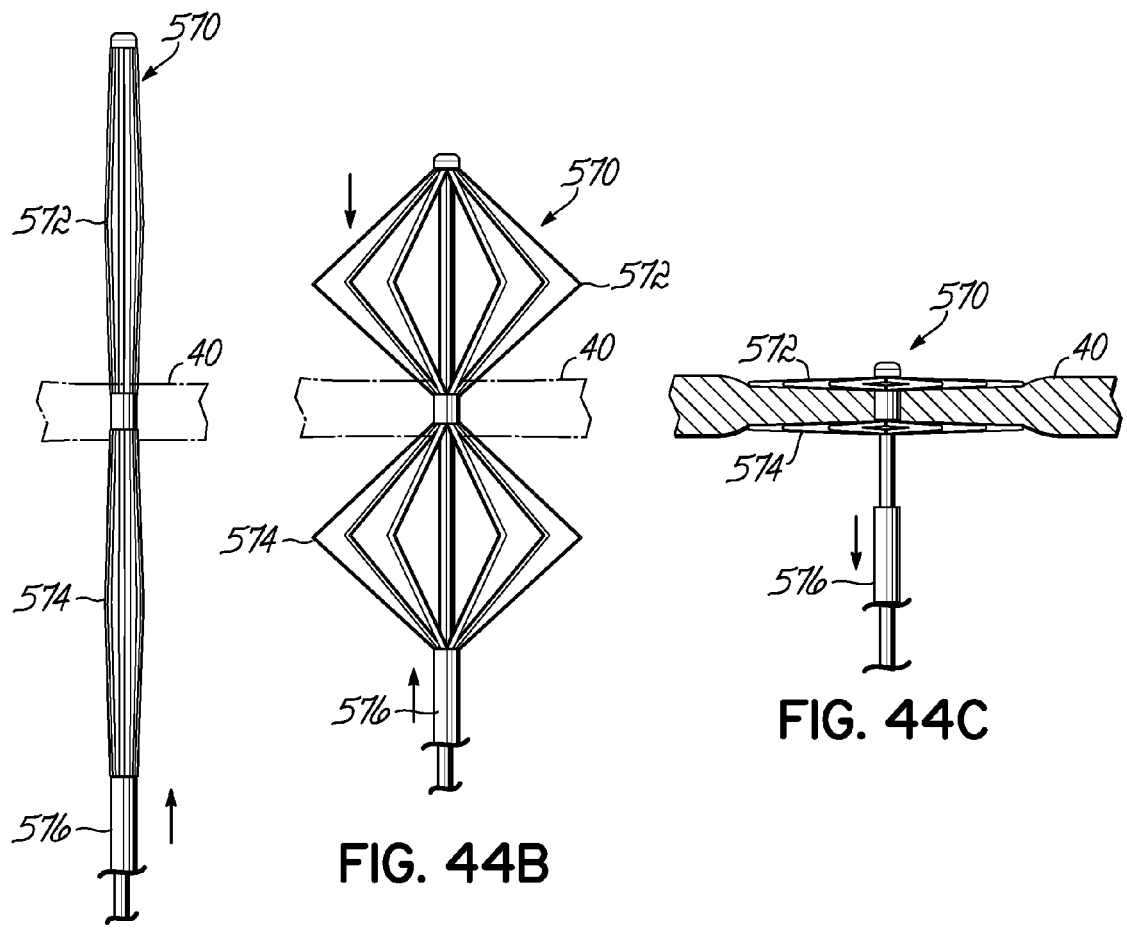
FIG. 44A
FIG. 44B
FIG. 44C

METHOD OF HEART VALVE REPAIR

CROSS-REFERENCE TO RELATED APPLICATIONS

This application is a divisional of U.S. Ser. No. 10/948,922, filed on Sep. 24, 2004 (pending) and assigned to the assignee of the present invention. The disclosure of U.S. Ser. No. 10/948,922 is hereby fully incorporated by reference herein.

The present application also claims the benefit of U.S. Provisional Application No. 60/531,855 filed on Dec. 23, 2003 (expired) and U.S. Provisional Application No. 60/554,314 filed Mar. 18, 2004 (expired), the disclosures of which are hereby incorporated herein by reference.

FIELD OF THE INVENTION

The present invention relates generally to techniques for treating mitral valve insufficiencies such as mitral valve leakage due to prolapse, papillary muscle dysfunction, or annular dilation. More particularly, the present invention relates to systems and methods for treating a leaking mitral valve in a minimally invasive manner. Various aspects of the invention further pertain more generally to magnetic guidance and/or fastener delivery systems used for approximating or otherwise operating on tissue.

BACKGROUND OF THE INVENTION

Congestive heart failure (CHF), which is often associated with an enlargement of the heart, is a leading cause of death. As a result, the market for the treatment of CHF is becoming increasingly prevalent. For instance, the treatment of CHF is a leading expenditure of Medicare and Medicaid dollars in the United States. Typically, the treatment of CHF enables many who suffer from CHF to enjoy an improved quality of life.

Referring initially to Fig. A, the anatomy of a heart 10, specifically the left side of the heart 10, includes a left atrium (LA) 12 and a left ventricle (LV) 14. An aorta 16 receives blood from left ventricle 14 through an aortic valve 18, which serves to prevent regurgitation of blood back into left ventricle 14. A mitral valve 20 is positioned between left atrium 12 and left ventricle 14, and allows one-way flow of blood from the left atrium 12 to the left ventricle 14.

Mitral valve 20, which will be described below in more detail, includes an anterior leaflet 22 and a posterior leaflet 24 that are coupled to cordae tendonae 26 which serve as "tension members" that prevent the leaflets 22, 24 of mitral valve 20 from going past their closing point and prolapsing back into the left atrium. When left ventricle 14 contracts during systole, cordae tendonae 26 limit the upward (toward the left atrium) motion of the anterior and posterior leaflets past the point at which the anterior and posterior leaflets 22, 24 meet and seal to prevent backflow from the left ventricle to the left atrium ("mitral regurgitation" or "mitral insufficiency"). Cordae tendonae 26 arise from a columnae carnae or, more specifically, a musculi papillares (papillary muscles) 28 of the columnae carnae. In various figures herein, some anatomical features have been deleted solely for clarity.

Fig. B is a cut-away top-view representation of mitral valve 20 and aortic valve 18. Anterior leaflet 22 and posterior leaflet 24 of the mitral valve 20 are generally thin, flexible membranes. When mitral valve 20 is closed (as shown in Fig. B), anterior leaflet 22 and posterior leaflet 24 are generally aligned and contact one another along a "line of coaptation" several millimeters back from their free edges, to create a seal that prevents mitral regurgitation. Alternatively, when mitral valve 20 is opened, blood flows downwardly through an opening created between anterior leaflet 22 and posterior leaflet 24 into left ventricle 14.

Many problems relating to mitral valve 20 may occur and may cause many types of ailments. Such problems include, but are not limited to, mitral regurgitation. Mitral regurgitation, or leakage, is the backflow of blood from left ventricle 14 into the left atrium 12 due to an imperfect closure or prolapse of mitral valve 20. That is, leakage often occurs when the anterior and posterior leaflets to not seal against each other, resulting in a gap 32 between anterior leaflet 22 and posterior leaflet 24.

In general, a relatively significant gap 32 may exist between anterior leaflet 22 and posterior leaflet 24 (as shown in Fig. C) for a variety of different reasons. For example, a gap 32 may exist due to congenital malformations, because of ischemic disease, or because the heart 10 has been damaged by a previous heart attack. A gap 32 may also be created when congestive heart failure, e.g., cardiomyopathy, or some other type of distress which causes a heart to be enlarged. Enlargement of the heart can result in dilation (stretching) of the mitral annulus. This enlargement is usually limited to the posterior valve annulus and is associated with the posterior leaflet, because the anterior annulus is a relatively rigid fibrous structure. When the posterior annulus enlarges, it causes the posterior leaflet to move away from the anterior leaflet, causing a gap because the two leaflets no longer form proper coaptation, and this results in leakage of blood through the valve, or regurgitation.

Leakage through mitral valve 20 generally causes a heart 10 to operate less efficiently, as the heart 10 must pump blood both out to the body via the aorta, and also back (in the form of mitral regurgitation) back into the left atrium. Leakage through mitral valve 20, or general mitral insufficiency, is thus often considered to be a precursor to CHF or a cause of progressive worsening of heart failure. There are generally different levels of symptoms associated with heart failure. Such levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort, and has symptoms of cardiac insufficiency even at rest. In general, correcting or reducing the degree of mitral valve leakage may be successful in allowing the NYHA classification grade of a patient to be reduced. For instance, a patient with a Class 4 classification may have his classification reduced to Class 3 or Class 2 and, hence, be relatively comfortable at rest or even on mild physical exertion. By eliminating the flow of blood backwards into the left atrium, therapies that reduce mitral insufficiency reduce the work load of the heart and may prevent or slow the worsening of heart function and congestive heart failure symptoms that is common when a significant degree of mitral insufficiency remains uncorrected.

Treatments used to correct for mitral valve leakage or, more generally, CHF, are typically highly invasive, open-heart surgical procedures as described below. In extreme cases, this may include implantation of a ventricular assist device such as an artificial heart in a patient whose own heart is failing. The implantation of a ventricular assist device is often expensive, and a patient with a ventricular assist device must be placed on extended anti-coagulant therapy. As will be appreciated by those skilled in the art, anti-coagulant therapy reduces the risk of blood clots being formed, as for example, within the ventricular assist device. While reducing the risks of blood clots associated with the ventricular assist device is desirable, anti-coagulant therapies may increase the risk of uncontrollable bleeding in a patient, e.g., as a result of a fall, which is not desirable.

Rather than implanting a ventricular assist device, bi-ventricular pacing devices similar to pace makers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive, and is generally not effective in significantly reducing or eliminating the degree of mitral regurgitation.

Open-heart surgical procedures which are intended to correct for mitral valve leakage, specifically, can involve the implantation of a replacement valve. Valves from animals, e.g., pigs, may be used to replace a mitral valve 20 in a human. While the use of a pig valve may relatively successfully replace a mitral valve, such valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting between ribs or sometimes removing parts of one or more ribs, as opposed to dividing the sternum to open the entire chest of a patient. In other words, the opening occurs between the ribs in a port access procedure, rather than opening a patient's sternum.

One open-heart surgical procedure that is particularly successful in correcting for mitral valve leakage and, in addition, mitral regurgitation, is an annuloplasty procedure. During an annuloplasty procedure, a medical device—an annuloplasty ring—may be implanted surgically on the left atrial side of mitral annulus (the attachment of the base of the mitral valve to the heart) to cause the size of a dilated mitral valve annulus to be reduced to a relatively normal size, and specifically to move the posterior leaflet closer to the anterior leaflet to aid anterior-posterior leaflet coaptation and thus improve the quality of mitral valve closure and significantly reduce the amount of mitral insufficiency. Fig. D is a schematic representation of an annuloplasty ring 34. An annuloplasty ring 34 is shaped approximately like the contour of a normal mitral valve 20. That is, annuloplasty ring 34 is shaped substantially like the letter "D." Typically, annuloplasty ring 34 may be formed from a rod or tube of biocompatible material, e.g., plastic, that has a DACRON mesh covering.

In order for annuloplasty ring 34 to be implanted, a surgeon surgically attaches annuloplasty ring 34 to the mitral valve on the atrial side of the mitral valve 20. Conventional methods for installing ring 34 require open-heart surgery which involve opening a patient's sternum and placing the patient on a heart bypass machine. As shown in Fig. E, annuloplasty ring 34 is sewn to a posterior leaflet 24 and an anterior leaflet 22 of a top portion of mitral valve 20. In sewing annuloplasty ring 34 onto mitral valve 20, a surgeon generally sews the straight side of the "D" to the fibrous tissue located at the junction between the posterior wall of the aorta and the base of the anterior mitral valve leaflet. As the curved part of the ring is sewn to the posterior aspect of the annulus, the surgeon alternately acquires a relatively larger amount of tissue from the mitral annulus, e.g., a one-eighth inch bite of tissue, using a needle and thread, compared to a relatively smaller bite taken of the fabric covering of annuloplasty ring 34. Once a thread has loosely coupled annuloplasty ring 34 to mitral valve tissue, annuloplasty ring 34 is slid into contact with the mitral annulus 40 such that the tissue of the posterior mitral annulus that was previously stretched out, e.g., due to an enlarged heart, is effectively reduced in circumference and pulled forwards towards the anterior mitral leaflet by the tension applied by annuloplasty ring 34 by the thread that binds the annuloplasty ring 34 to the mitral annulus tissue. As a result, a gap, such as gap 32 of Fig. C, between anterior leaflet 22 and posterior leaflet 24 during ventricular contraction (systole) may be reduced and even substantially closed off in many cases thereby significantly reducing or even eliminating mitral insufficiency. After the mitral valve 20 is shaped by ring 34, the anterior and posterior leaflets 22, 24 will reform typically by pulling the posterior leaflet forward to properly meet the anterior leaflet and create a new contact line that will enable mitral valve 20 to appear and to function properly.

Once implanted, tissue generally grows over annuloplasty ring 34, and a line of contact between annuloplasty ring 34 and mitral valve 20 will essentially enable mitral valve 20 to appear and function normally. Although a patient who receives annuloplasty ring 34 may be subjected to anti-coagulant therapies, the therapies are not extensive, as a patient is only subjected to the therapies for a matter of weeks, e.g., until tissue grows over annuloplasty ring 34.

A second surgical procedure which is generally effective in reducing mitral valve leakage associated with prolapse of the valve leaflets involves placing a single edge-to-edge suture in the mitral valve 20 that opposes the mid-portions of anterior and posterior leaflets. With reference to Fig. F, such a surgical procedure, e.g., an Alfieri stitch procedure or a bow-tie repair procedure, will be described. An edge-to-edge stitch 36 is used to stitch together an area at approximately the center of the gap 32 defined between an anterior leaflet 22 and a posterior leaflet 24 of a mitral valve 20. Once stitch 36 is in place, stitch 36 is pulled in to form a suture which holds anterior leaflet 22 against posterior leaflet 24, as shown. By reducing the size of gap 32, the amount of leakage through mitral valve 20 may be substantially reduced.

Although the placement of edge-to-edge stitch 36 is generally successful in reducing the amount of mitral valve leakage through gap 32, edge-to-edge stitch 36 is conventionally made through open-heart surgery. In addition, the use of edge-to-edge stitch 36 is generally not suitable for a patient with an enlarged, dilated heart, as blood pressure causes the heart to dilate outward, and may put a relatively large amount of stress on edge-to-edge stitch 36. For instance, blood pressure of approximately 120/80 or higher is typically sufficient to cause the heart 10 to dilate outward to the extent that edge-to-edge stitch 36 may become undone, or tear mitral valve tissue.

Another surgical procedure which reduces mitral valve leakage involves placing sutures along a mitral valve annulus around the posterior leaflet. A surgical procedure which places sutures along a mitral valve 20 will be described with respect to Fig. G. Sutures 38 are formed along the annulus 40 of a mitral valve 20 that surrounds the posterior leaflet 24 of mitral valve 20. These sutures may be formed as a double track, e.g., in two "rows" from a single strand of suture material 42. Sutures 38 are tied off at approximately a central point (P2) of posterior leaflet 24. Pledgets 44 are often positioned under selected sutures, e.g., at the two ends of the sutured length of annulus or at the central point P2, to prevent sutures 38 from tearing through annulus 40. When sutures 38 are tightened and tied off, the circumference of the annulus 40 may effectively be reduced to a desired size such that the size of a gap 32 between posterior leaflet 24 and an anterior leaflet 22 may be reduced.

The placement of sutures 38 along annulus 40, in addition to the tightening of sutures 38, is generally successful in reducing mitral valve leakage. However, the placement of sutures 38 is conventionally accomplished through open-heart surgical procedures. That is, like other conventional procedures, a suture-based annuloplasty procedure is invasive.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people who are not greatly inconvenienced by CHF symptoms, e.g., people at a Class 1 classification, may choose not to have corrective surgery. In addition, people who most need open heart surgery, e.g., people at a Class 4 classification, may either be too frail or too weak to undergo the surgery. Hence, many people who may benefit from a surgically repaired mitral valve may not undergo surgery.

Fig. H illustrates the cardiac anatomy, highlighting the relative position of the coronary sinus (CS) 46 running behind the posterior leaflet 24 of the mitral valve 20. Fig. I is an illustration of the same anatomy but schematically shows a cinching device 48 which is placed within the CS 46 using a catheter system 50, with distal, mid, and proximal anchors 52a, 52b, 52c within the lumen of the CS 46 to allow plication of the annulus 40 via the CS 46. In practice, these anchors 52a-c are cinched together, i.e., the distance between them is shortened by pulling a flexible tensile member 54 such as a cable or suture with the intent being to shorten the valve annulus 40 and pull the posterior leaflet 24 closer to the anterior leaflet 22 in a manner similar to an annuloplasty procedure. Unfortunately, since the tissue which forms the CS 46 is relatively delicate, the anchors 52a-c are prone to tear the tissue during the cinching procedure, and the effect on the mitral annulus may be reduced by the position of the coronary sinus up more towards the left atrium rather than directly over the mitral annulus itself. Other minimally invasive techniques have been proposed and/or developed but have various drawbacks related to such factors as effectiveness and/or cases and accuracy of catheter-based implementation.

Therefore, there remains a need for improved minimally invasive treatments for mitral valve leakage. Specifically, what is desired is a method for decreasing the circumference of the posterior mitral annulus, moving the posterior leaflet forwards towards the anterior leaflet and thereby reducing leakage between an anterior leaflet and a posterior leaflet of a mitral valve, in a manner that does not require conventional surgical intervention.

SUMMARY OF THE INVENTION

The invention provides a method of modifying an annulus of a heart valve in a first general aspect. The annulus lies generally below the coronary sinus at least at one location. The method comprises fastening the coronary sinus to the annulus to bring the annulus closer to the coronary sinus at least at the one location, and then reducing regurgitation by modifying the annulus. For example, the annulus may be modified by shortening the circumferential length (i.e., the arc length) of the annulus or changing the shape or other physical characteristic of the annulus. Fastening the coronary sinus can further comprise inserting a first guide element into the coronary sinus, directing a second guide element into the left ventricle so it lies under and/or adjacent to the annulus, securing the first and second guide elements together, and applying a fastener between the annulus and the coronary sinus.

The guide elements may be removed after applying the fastener, and therefore act as a temporary anchor for the fastener delivery device and/or the tissue to be secured. Alternatively, the guide elements, or portions thereof, may be left in place. The guide elements may comprise mechanical fasteners or other types of fasteners such as magnets (i.e., magnetic elements), or combinations thereof. One guide element of the invention comprises first and second spaced apart magnets on the distal support portion of a catheter. Repelling poles of the magnets face each other to create a circumferential virtual pole emanating around the gap formed between the spaced apart magnets. Securing the first and second guide elements together can further comprise magnetically attracting the first and second guide elements together. The same catheter device may be used to direct the second guide element and apply the fastener. In addition, the method can include applying a second fastener to the annulus, coupling the first and second fasteners together, and reducing the distance between the first and second fasteners to reduce the circumference of the annulus. In this case applying the first and second fasteners can occur through the same catheter device. More particularly, the method can involve serially applying the first and second fasteners through one lumen in a catheter device or, as another example, applying the first and second fasteners through different lumens of the same catheter device. In another aspect of the invention, at least one flexible tensile member is used to couple the first and second fasteners together and the flexible tensile member is tensioned to reduce the distance between the first and second fasteners. Shortening the circumferential length of the annulus can further comprise fastening a flexible fabric to the annulus and shortening the circumferential length of the flexible fabric.

In another general aspect, a method of modifying an annulus of a heart valve comprises applying first and second fasteners on opposite sides of the annulus through at least one catheter thereby holding heart tissue between the first and second fasteners, applying third and fourth fasteners on opposite sides of the annulus through at least one catheter thereby holding heart tissue between the third and fourth fasteners. As with the fasteners applied in the various aspects of this invention, different catheters or different catheter portions may be used to apply the different fasteners or the same catheter may be used. The first and second fasteners are coupled and the third and fourth fasteners are coupled using at least one flexible tensile member. The distance between adjacent ones of at least two of the first, second, third and fourth fasteners is reduced by applying tension to the flexible tensile member thereby modifying the annulus.

The first, second, third, and fourth fasteners can include at least one magnet and/or at least one mechanical fastening element, such as a mechanical element configured to penetrate and engage with tissue. In addition, the method can include using at least one magnet delivered through a catheter to guide at least one of the fasteners into position. As one option, the guiding magnet may be removed after guiding the fastener or fasteners into position. The fastener or fasteners may be delivered through the guiding magnet.

In another general aspect of the invention, a heart valve annulus is modified by delivering a first fastener through a catheter into the coronary sinus, and delivering a second fastener through a catheter to at least one of two locations, the two locations being 1) generally above the annulus in the left atrium, and 2) generally below the annulus in the left ventricle. The fasteners are secured to the annulus and the distance between the first and second fasteners is reduced to thereby modify the annulus with the respectively delivered fasteners. In another aspect, a flexible tensile member is connected between the fasteners, and the distance between the fasteners is reduced by tensioning the flexible tensile member to modify the annulus. The flexible tensile member may be locked into position with respect to the fasteners by applying a crimp member or other locking element, which may or may not be part of a fastener, to the flexible tensile member. In another embodiment, the fasteners are held in spaced apart positions while securing the fasteners to heart tissue at the two locations. The fasteners are biased toward each other to reduce the distance between adjacent fasteners and modify the annulus with the respectively delivered fasteners. Biasing the fasteners can further comprise magnetically attracting adjacent fasteners toward one another or, as another example, spring biasing adjacent fasteners toward one another. As one option, pressurized air may be used to hold the fasteners in the spaced apart positions prior to biasing the fasteners together. In another aspect, radio frequency energy or any other suitable method is used to form an aperture in the heart tissue in order to apply the fastener(s) through the tissue.

The invention further provides a system for modifying an annulus of a heart valve comprising a first catheter, a first magnet coupled with the first catheter in such a manner that the first catheter is operative to deliver the first magnet adjacent to the annulus. The system further includes a second catheter and a second magnet coupled with the second catheter in such a manner that the second catheter is operative to deliver the second magnet adjacent to the annulus. A fastener delivery portion may be operatively associated with the first catheter. The fastener delivery portion may be coupled at predetermined angle relative to an axis of magnetic attraction between the first and second magnets.

The fastener delivery portion can be movable relative to the first and second magnets so as to enable delivery of a fastener to a desired position. The system can further comprise a plurality of fastener delivery portions configured to deliver respective fasteners at spaced apart locations along the annulus. The plurality of fasteners may be coupled together with at least one flexible tensile member such that the flexible tensile member is capable of drawing the fasteners together and thereby modifying the annulus.

In another embodiment, a catheter system for modifying an annulus of a heart valve comprises a catheter having at least one lumen and first and second fasteners coupled together by an elongate flexible member such that the first fastener is movable along the elongate flexible member to a position closer to the second fastener. An actuation device is coupled in a releasable manner to the elongate flexible member and adapted to pull the elongate flexible member to thereby reduce the distance between the first and second fasteners. A coupling secures the elongate flexible member in a locked position relative to the first and second fasteners. The first and second fasteners can further comprise magnets and/or mechanical fasteners, such as fasteners having projections configured to penetrate heart tissue. The coupling further can further comprise a crimpable or other type of locking member. The first and second fasteners may be further coupled together by a length adjustable member configured to allow the distance between the first and second fasteners to be shortened as the actuation mechanism pulls the flexible tensile member. The length adjustable member can include first and second telescoping portions coupled together or, as another example, a generally accordion-shaped section.

In another embodiment, a catheter system for modifying an annulus of a heart valve comprises a catheter having at least one lumen and first and second fasteners coupled together by a flexible tensile member such that the first fastener is movable along the flexible tensile member relative to the second fastener. A first fastener delivery portion is coupled with the catheter and delivers the first fastener into a first position proximate the annulus. A second fastener delivery portion is coupled with the catheter and moves with respect to the first fastener delivery portion. The second fastener delivery portion delivers the second fastener into a second position proximate the annulus and spaced from the first position. This system can further include a third fastener coupled to the flexible tensile member, and a third fastener delivery portion coupled with the catheter and capable of delivering the third fastener into a third position proximate the annulus and spaced from the first and second positions. The system can also include first and second fastener drive members coupled respectively with the first and second fastener delivery portions, and being selectively movable to drive the first and second fasteners into the tissue proximate the annulus.

The systems of this invention can include fastener delivery portions comprising at least one spring and drive member each located, for example, at the distal end of a catheter device. Such fastener delivery portions can force the fastener(s) into tissue proximate the annulus. Catheters used in the invention can include a magnet at the distal end for coupling with another magnet located proximate the annulus thereby stabilizing the catheter during delivery of the fastener(s). A lock member may be secured to the flexible tensile member and used to selectively prevent relative movement between the delivered fasteners.

In another embodiment, a catheter system for modifying an annulus of a heart valve includes a catheter having at least one lumen and first and second fasteners coupled together by a flexible tensile member and adapted to be secured to heart tissue proximate the annulus. A rod is movable between a compact state within the lumen and an expanded state outside of the lumen. The first and second fasteners are further coupled to the rod such that the first fastener is movable along the rod relative to the second fastener by applying tension to the flexible tensile member. The rod may be generally C-shaped in the expanded state so as to follow the annulus. A third fastener may be coupled for movement along the rod and adapted to be secured to heart tissue proximate the annulus. A second flexible tensile member can be secured to the third fastener. The third fastener may then be moved along the rod relative to the second fastener by applying tension to the second flexible tensile member. A magnet can be connected to the rod and adapted to magnetically couple with a magnet in the coronary sinus for stabilizing the position of the rod as the fasteners are secured to the heart tissue.

Another catheter system for modifying an annulus of a heart valve generally comprises a catheter having at least one lumen and first and second fasteners adapted to be secured to heart tissue proximate the annulus. At least one flexible tensile member couples the first and second fasteners together. A locking device activated by way of a catheter to fix the fastener positions is provided. For example, a locking element delivery device is deployable through a catheter, which may be the same catheter as a fastener delivery catheter, or a different catheter. For example, the locking element can be a crimp and a compression applying mechanism deployed from the catheter can be configured to compress the crimp onto the flexible tensile member after the fasteners are pulled toward one another with the flexible tensile member to modify the annulus. Other types of locking elements may, for example, include spring elements or other biased elements which are held in an open position and then released into a closed or locked position onto one or more flexible tensile members. Any locking element which is selectively lockable onto a flexible tensile member may be used as appropriate for the application. A flexible tensile member releasing device is provided which releases the flexible tensile member from the catheter system is also provided. This may involve a mechanical disconnection mechanism, such as threads or other connectors, or a cutting mechanism associated which cuts the flexible tensile member after locking takes place, such as mentioned above. A third fastener is adapted to be secured to the heart tissue, and separate flexible tensile members may be connected with each of the fasteners and threaded through the locking element, such as a crimp. It will be appreciated that the term "flexible tensile members", as used herein, will apply to separate portions of a single element, such as a suture strand, wire, cable or other solid or hollow elongate structure which may be looped back on itself and locked in place, and it will also apply to separate elements altogether.

Another catheter system for modifying an annulus of a heart valve comprises first, second and third fasteners adapted to be secured to heart tissue proximate the annulus. First, second and third flexible tensile members are respectively connectable to the first, second and third fasteners. A generally V-shaped valve support member is provided having a pair of legs movable between a compact state suitable for carrying the valve support member within a catheter and an expanded state in which the legs are more separated. A free end of each leg includes respective first and second eyelets receiving the first and second flexible tensile members and an apex between the pair of legs including a third eyelet receiving the third flexible tensile member. First, second and third crimp members may be provided for respectively securing the first, second and third flexible tensile members with respect to the first, second and third eyelets after at least one of the flexible tensile members is pulled tight to modify the shape of the annulus.

Various additional features, advantages, and aspects of the invention will become more readily apparent to those of ordinary skill in the art upon review of the following detailed description of the illustrative embodiments taken in conjunction with the accompanying drawings.

BRIEF DESCRIPTION OF THE DRAWINGS

Fig. A is a cutaway of the left side of the heart showing the internal muscular and valve structure.

Fig. B is a top view showing the normal positions of a mitral valve and adjacent aortic valve.

Fig. C is a top view similar to Fig. B but illustrating the mitral valve in a prolapsed condition in which the posterior leaflet is separated from the anterior leaflet.

Fig. D is an elevational view illustrating a conventional annuloplasty ring.

Fig. E is a top view similar to Fig. B, but illustrating the attachment of the annuloplasty ring to the mitral valve annulus.

Fig. F is a top view of the mitral valve illustrating an Alfieri stitch technique for reducing the gap between the posterior and anterior leaflets.

Fig. G is a top view of the mitral valve illustrating another suturing technique which has been used to close the gap between the posterior and anterior leaflets.

Fig. H is a cross sectional view of the heart anatomy illustrating the coronary sinus (CS) running behind the posterior leaflet of the mitral valve.

Fig. I is a cross sectional view of the heart anatomy similar to Fig. H, but illustrating a technique for inserting anchors into the CS using a catheter based system.

Figure 1A:
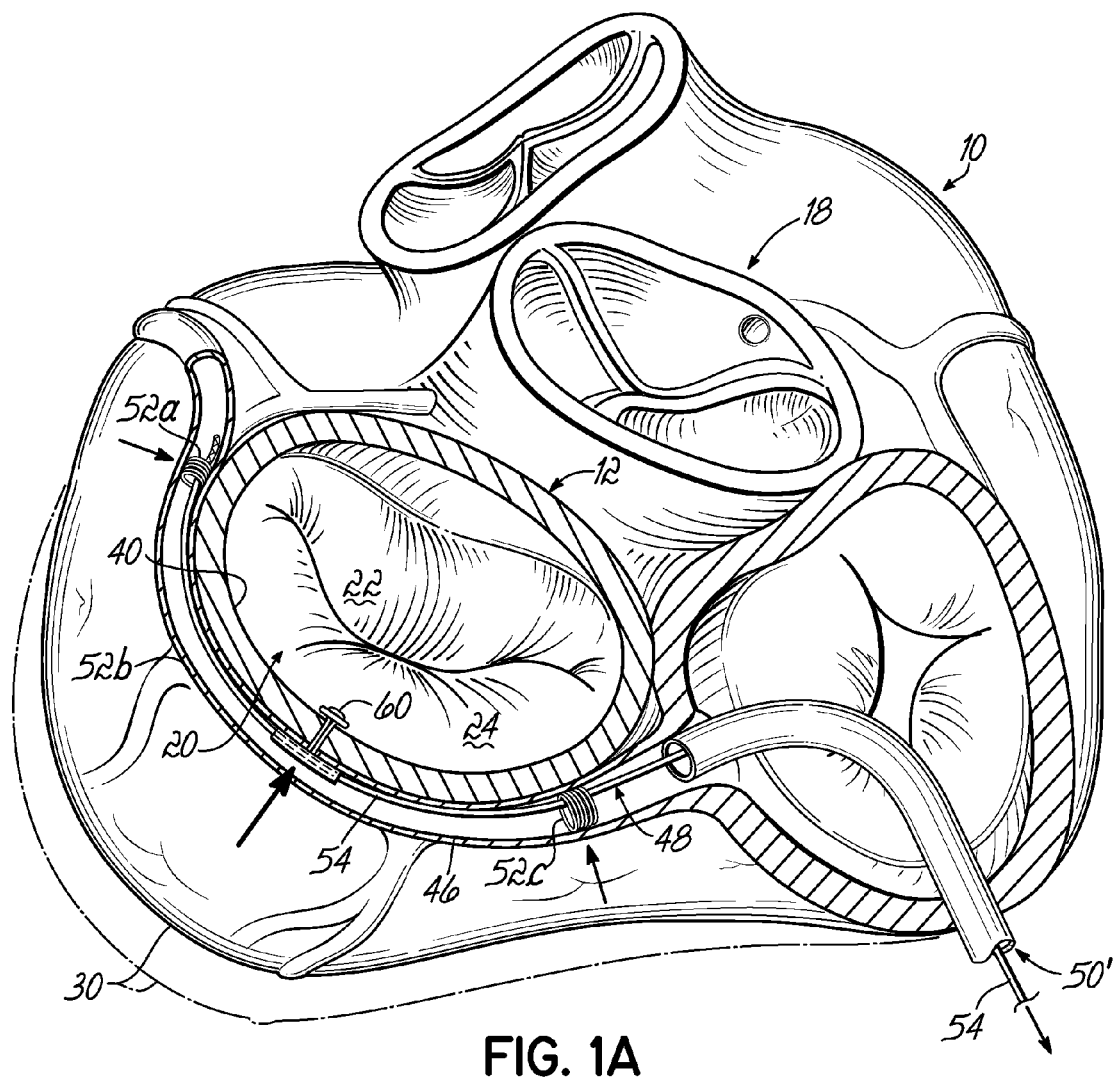

FIG. 1A is a cross sectional view of the heart anatomy similar to Fig. I but illustrating an improved catheter based procedure for inserting anchors into the CS and correcting for mitral valve insufficiency according to the invention.

Figure 1B:
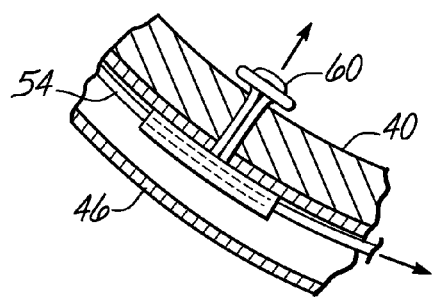

FIG. 1B is an enlarged view of the connector placed in accordance with the invention through the CS and the annulus tissue of the mitral valve.

Figure 2A:
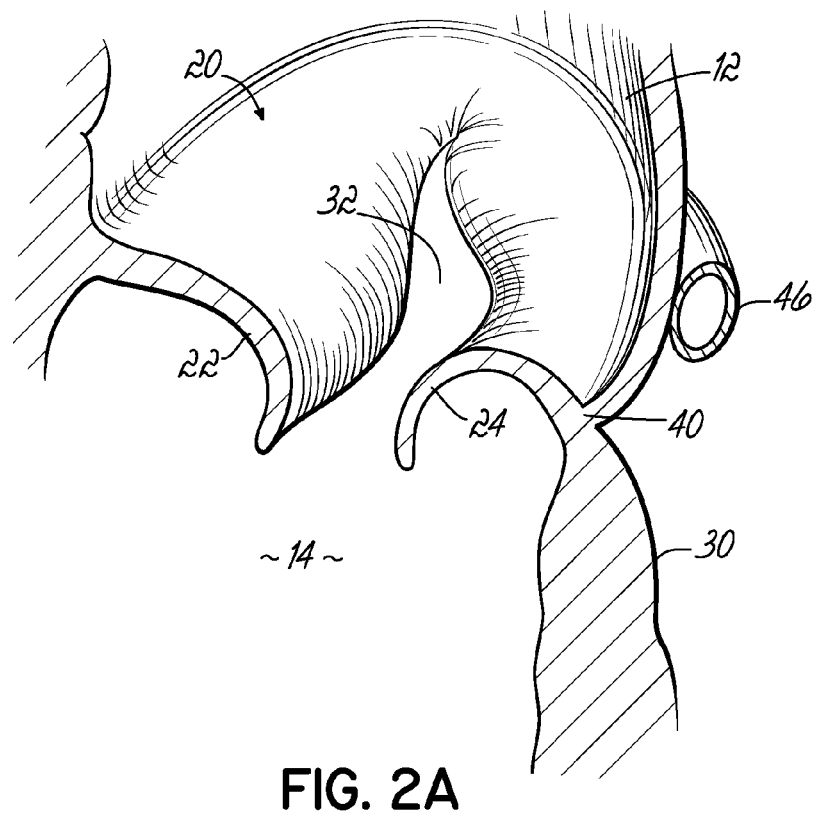

FIG. 2A is a cross sectional view of the mitral valve illustrating the posterior and anterior leaflets and the relative position of the CS with respect to the valve annulus.

Figure 2B:
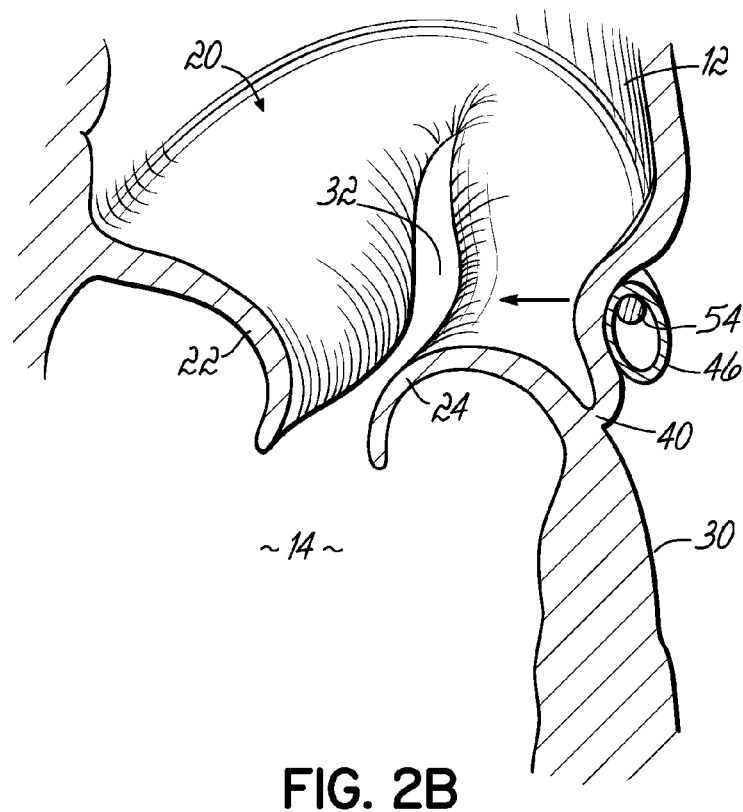

FIG. 2B is a view similar to FIG. 2A and illustrating the effect of cinching or pulling the CS toward the mitral valve opening at a location which is above the level of the valve annulus.

Figure 2C:
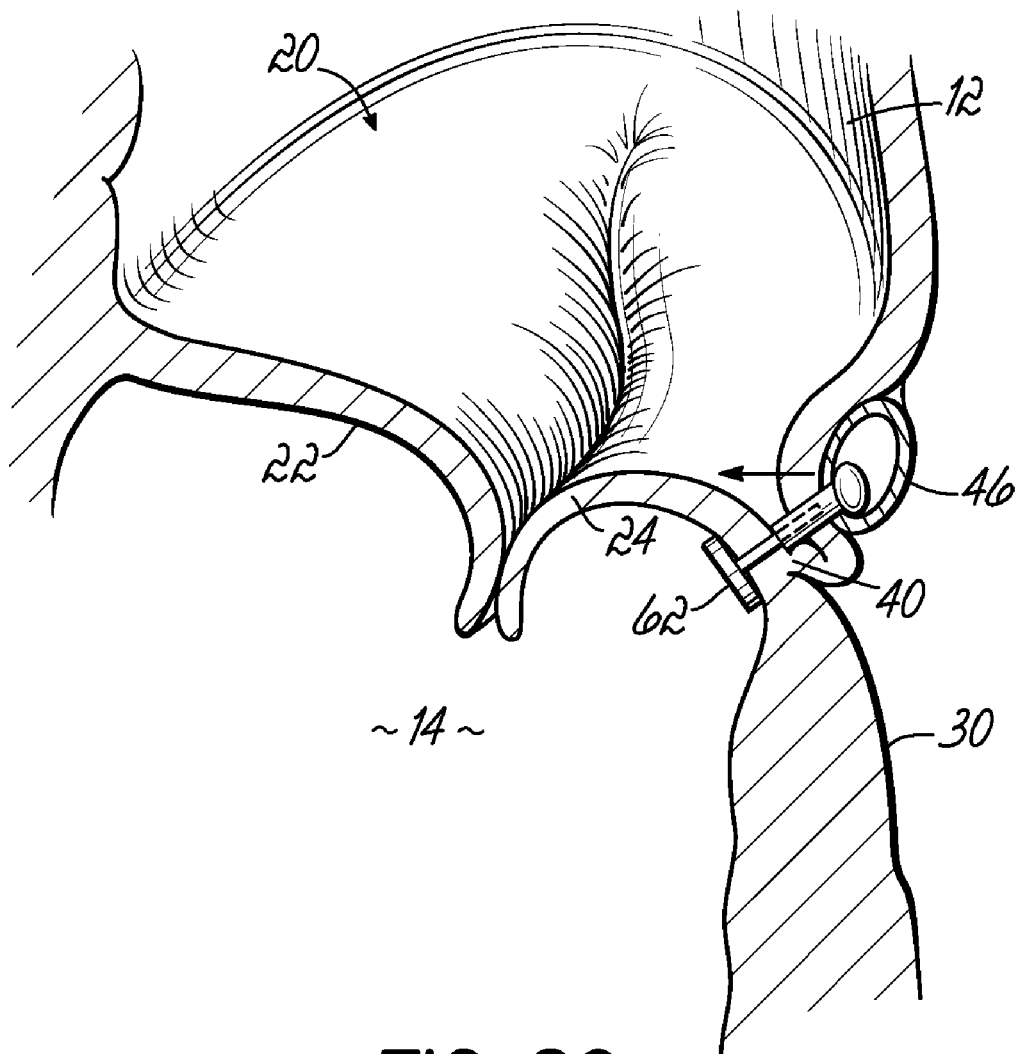

FIG. 2C is a view similar to FIG. 2B, but illustrating the placement of a fastener in accordance with the invention to bring the level of the CS closer to the annulus before cinching.

Figure 3:
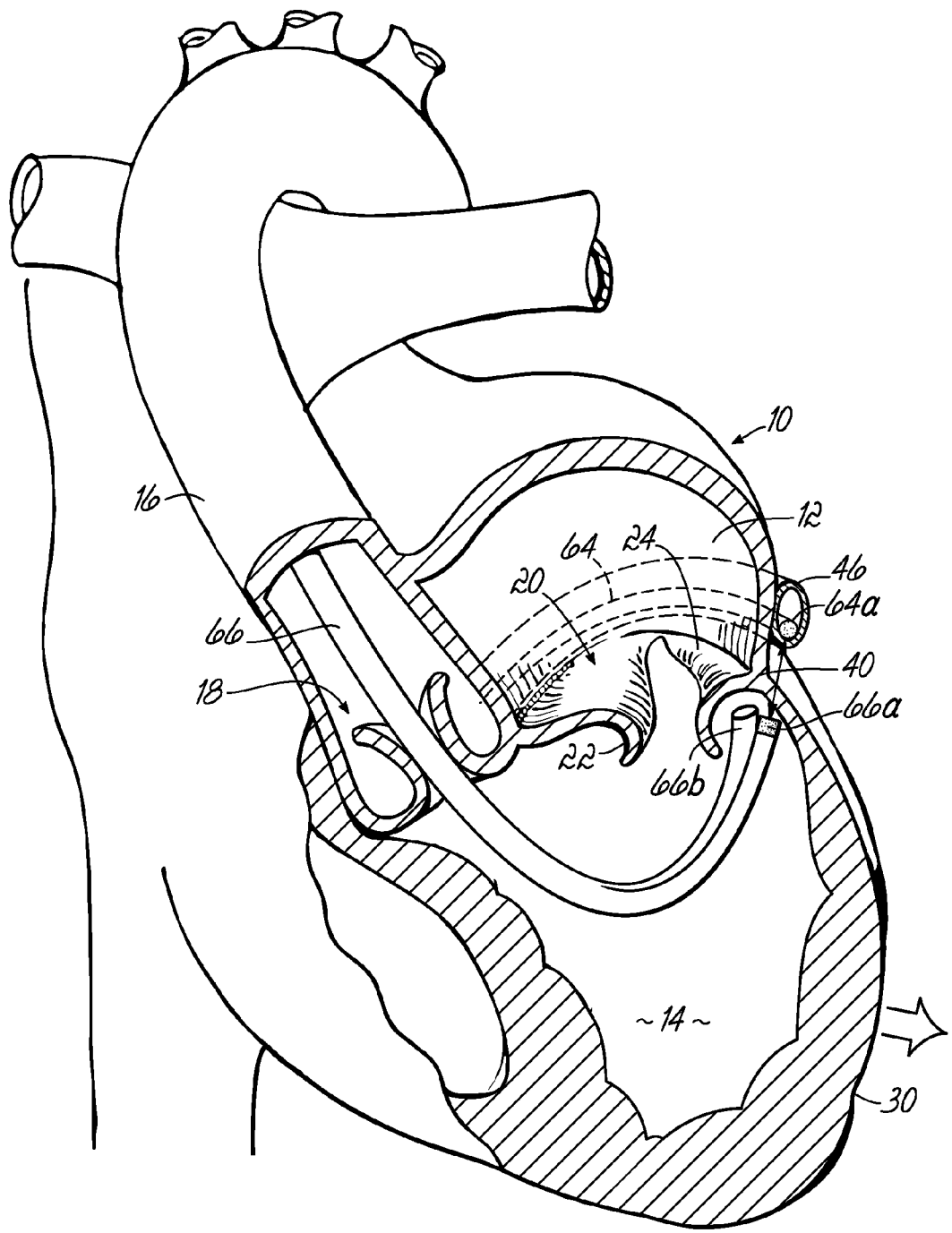

FIG. 3 is a cross sectional view of the heart anatomy, on the left side of the heart, illustrating a catheter based system according to the invention.

FIGS. 3A-3D illustrate a progression of steps in a catheter based method for correcting a mitral valve insufficiency in accordance with the invention.

Figure 4:
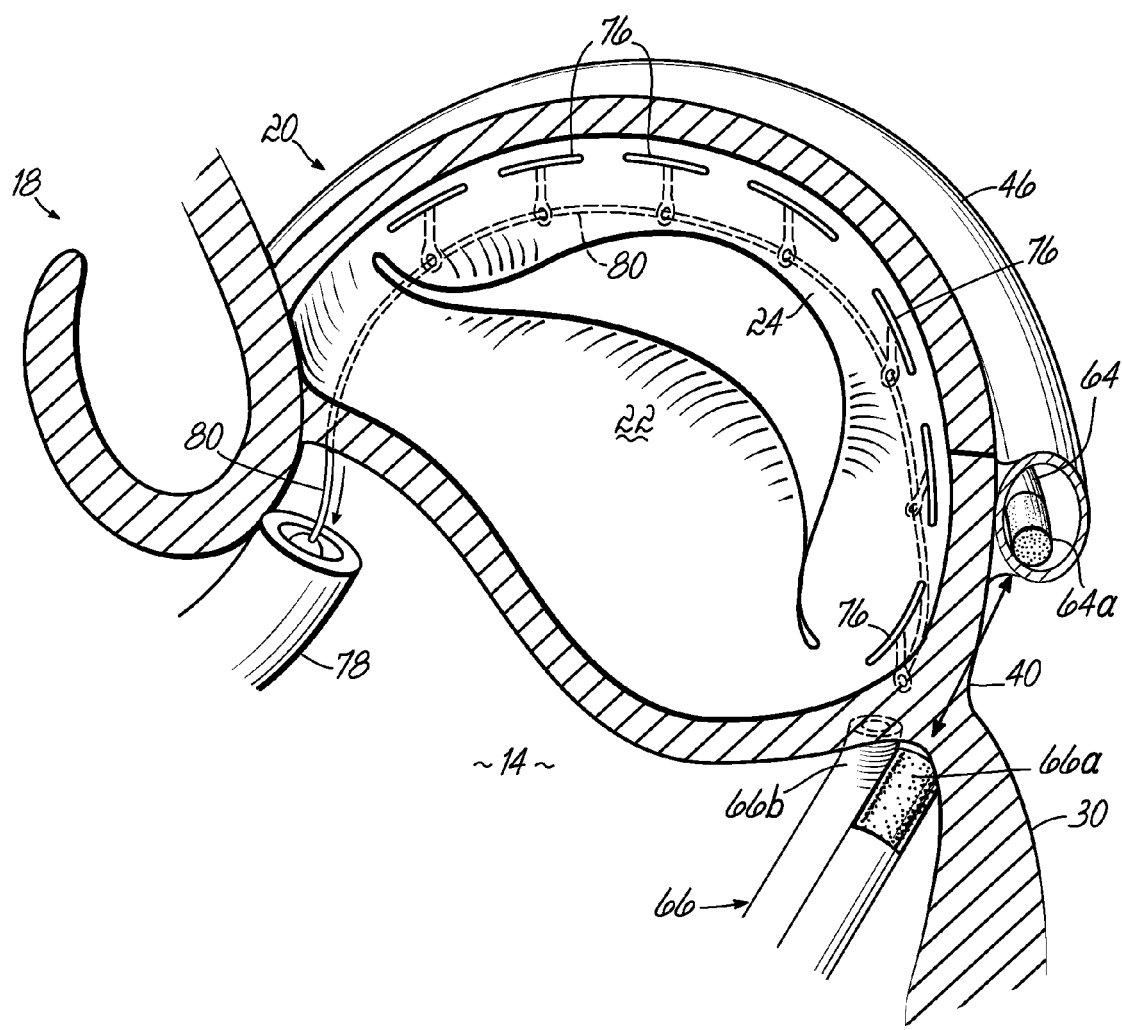
Figure 5:
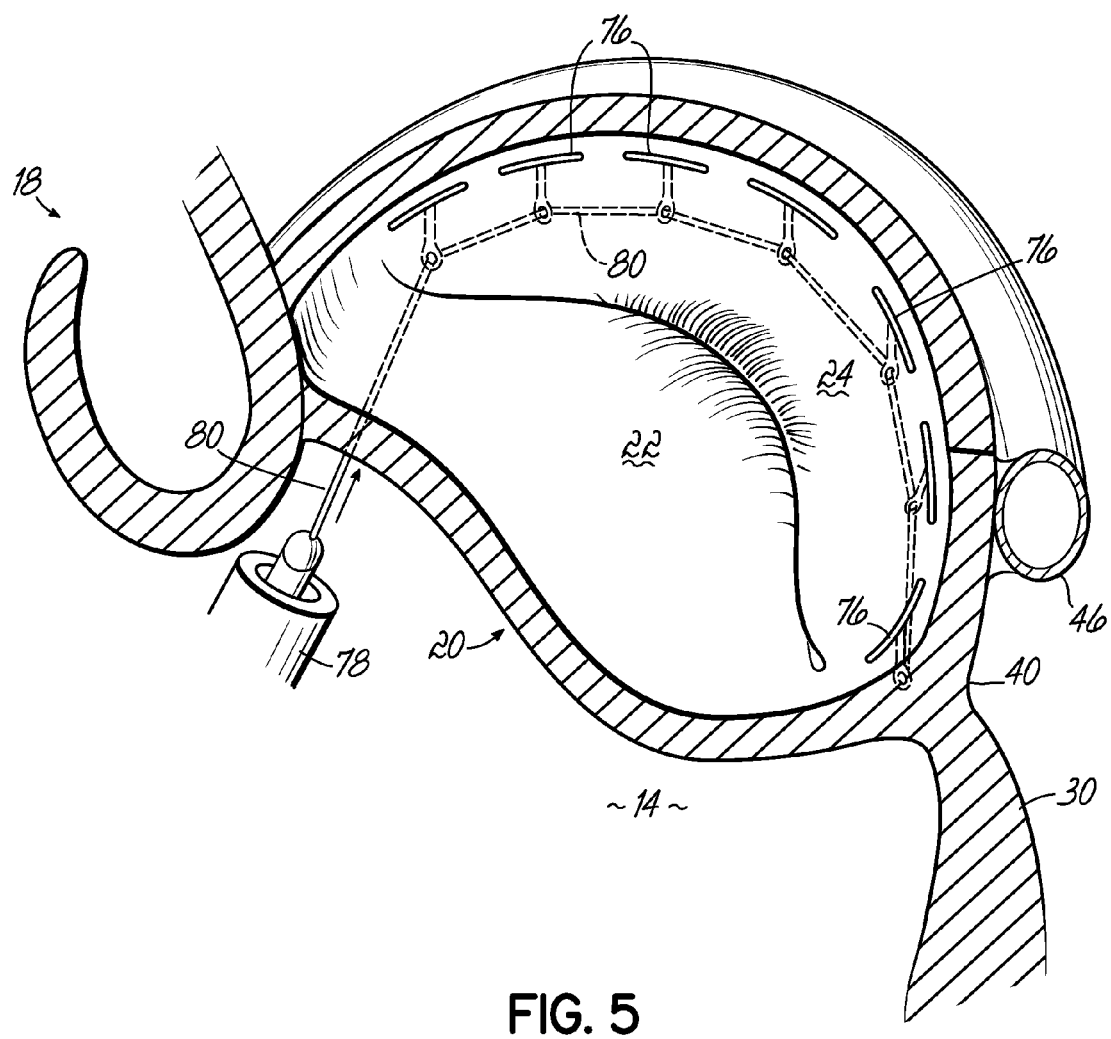

FIGS. 4 and 5 illustrate a cross section of the mitral valve in which anchors have been daisy chained together and then cinched to close the gap between the leaflets of the valve.

FIGS. 6A-6E-1 illustrate a cross section of the heart anatomy through the CS and illustrating a pair of catheter devices being used to successively apply fasteners in a daisy chained fashion and both cinch and lock the fasteners in place.

Figure 6A:
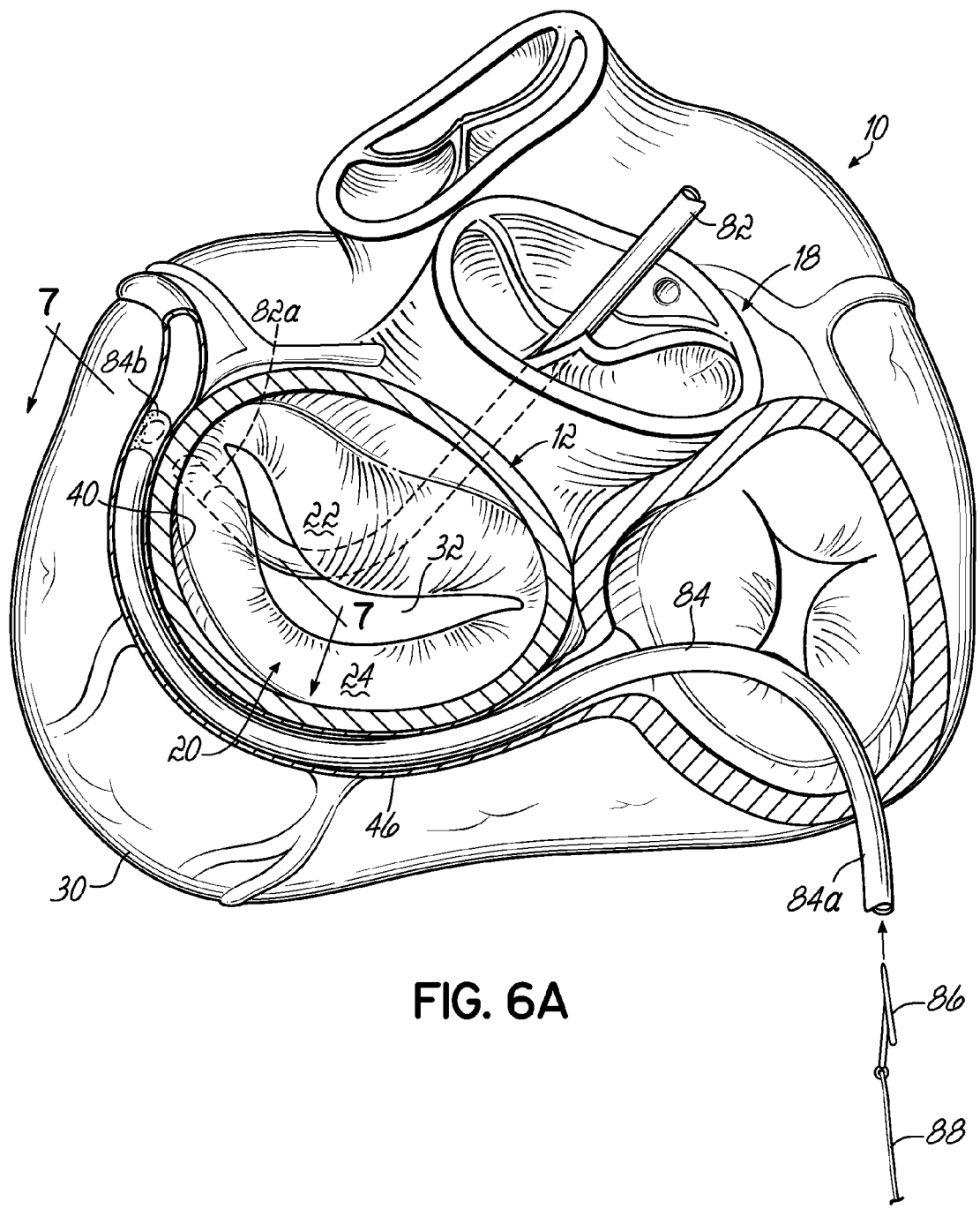
Figure 6B:
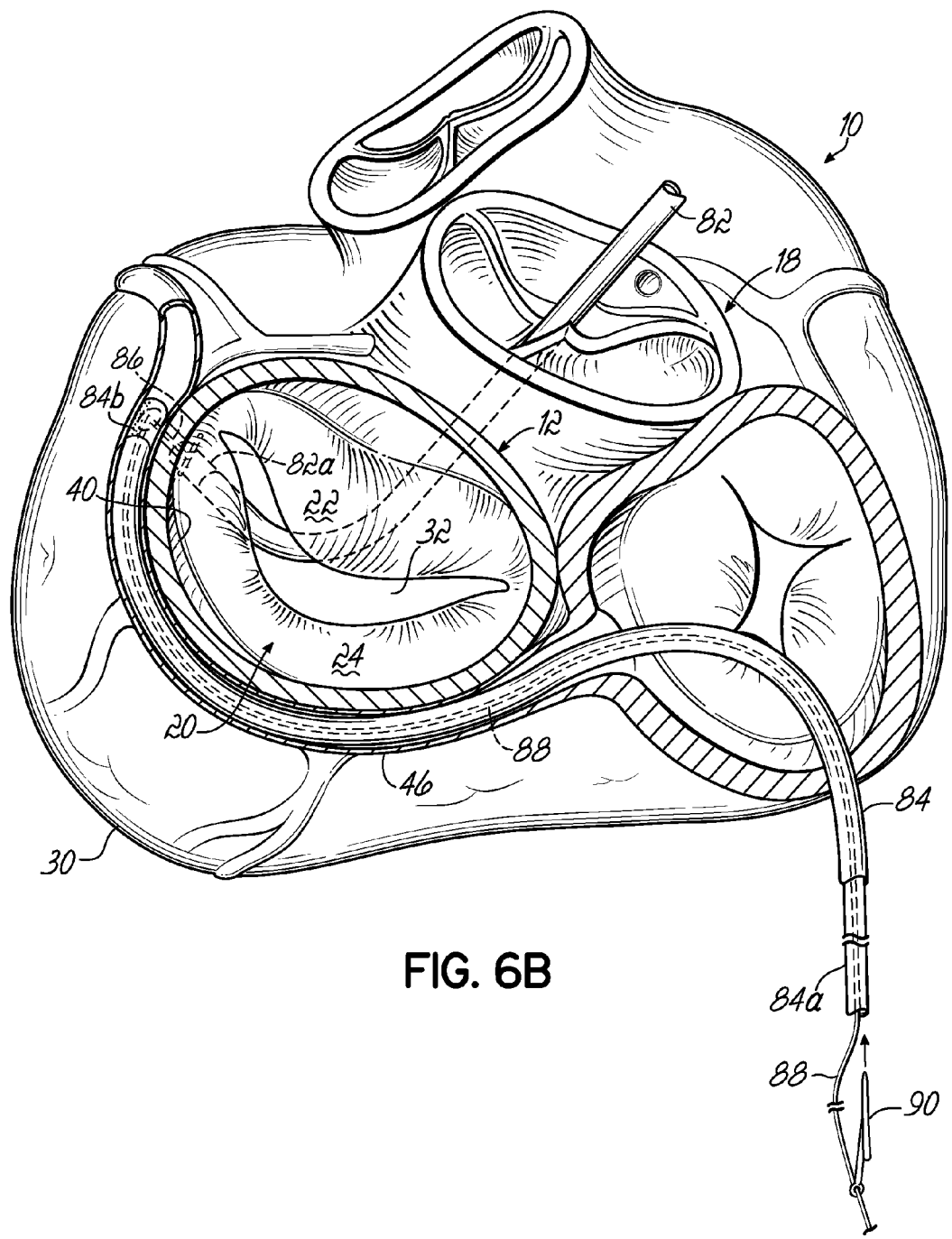
Figure 6C:
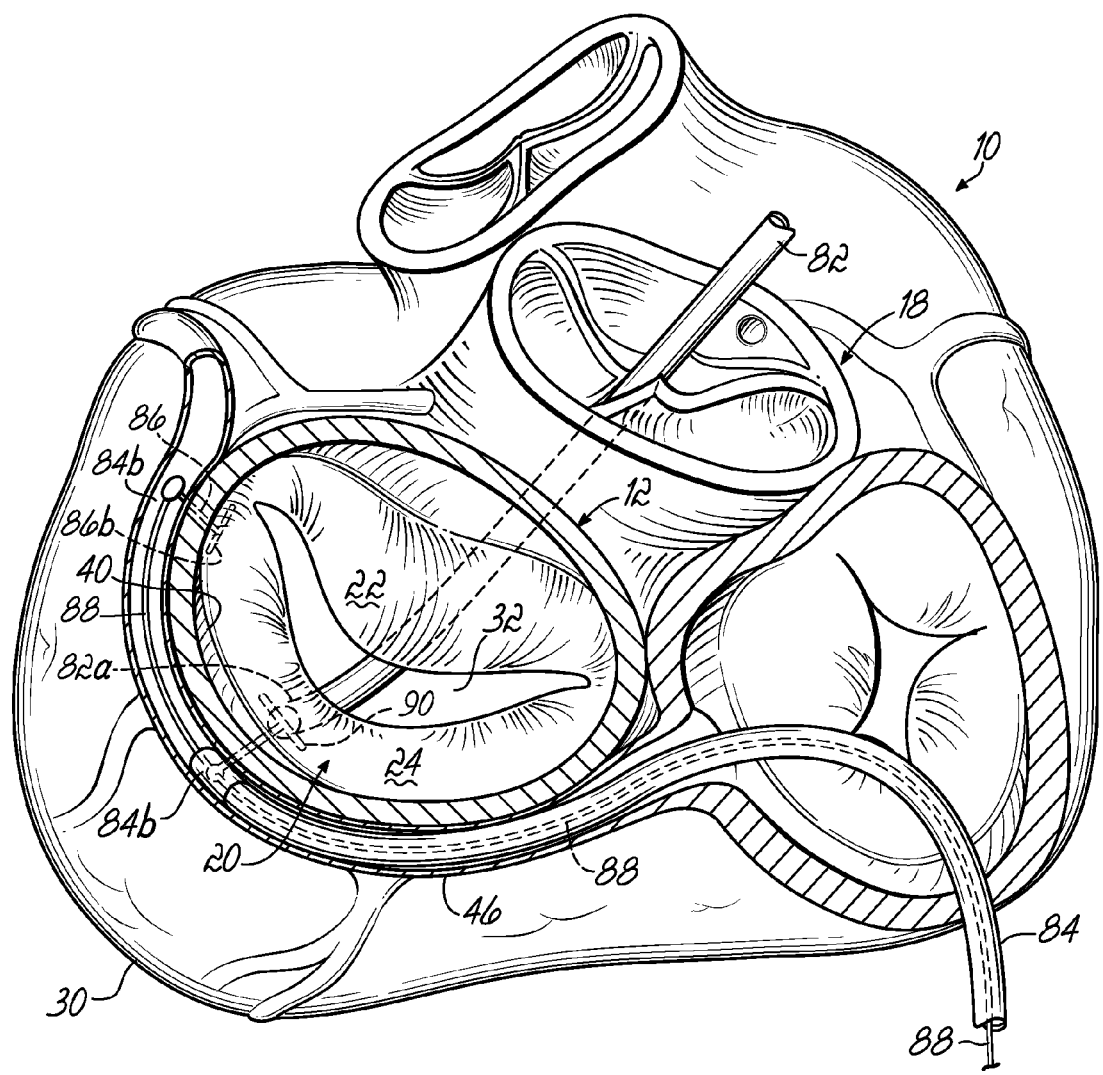
Figure 6D:
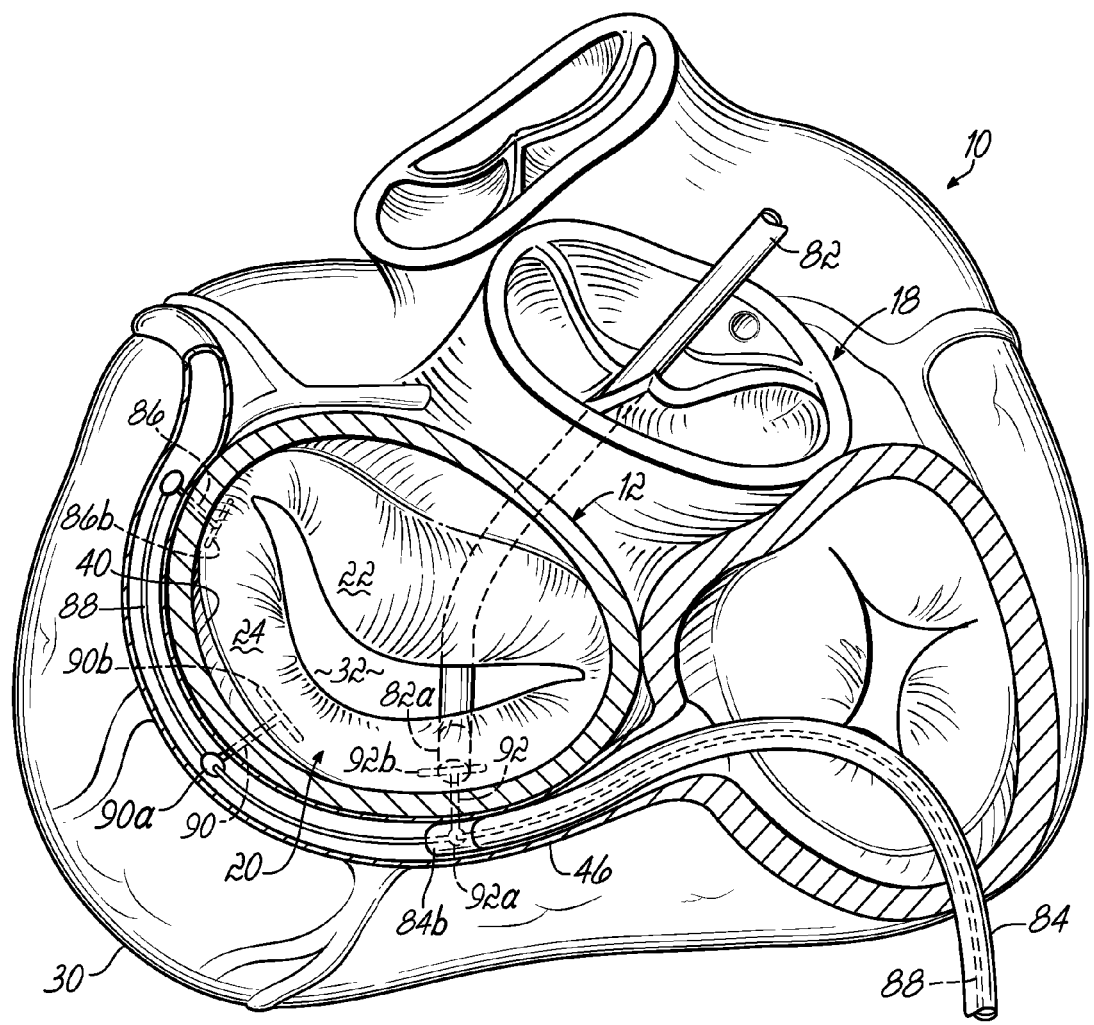
Figure 6E:
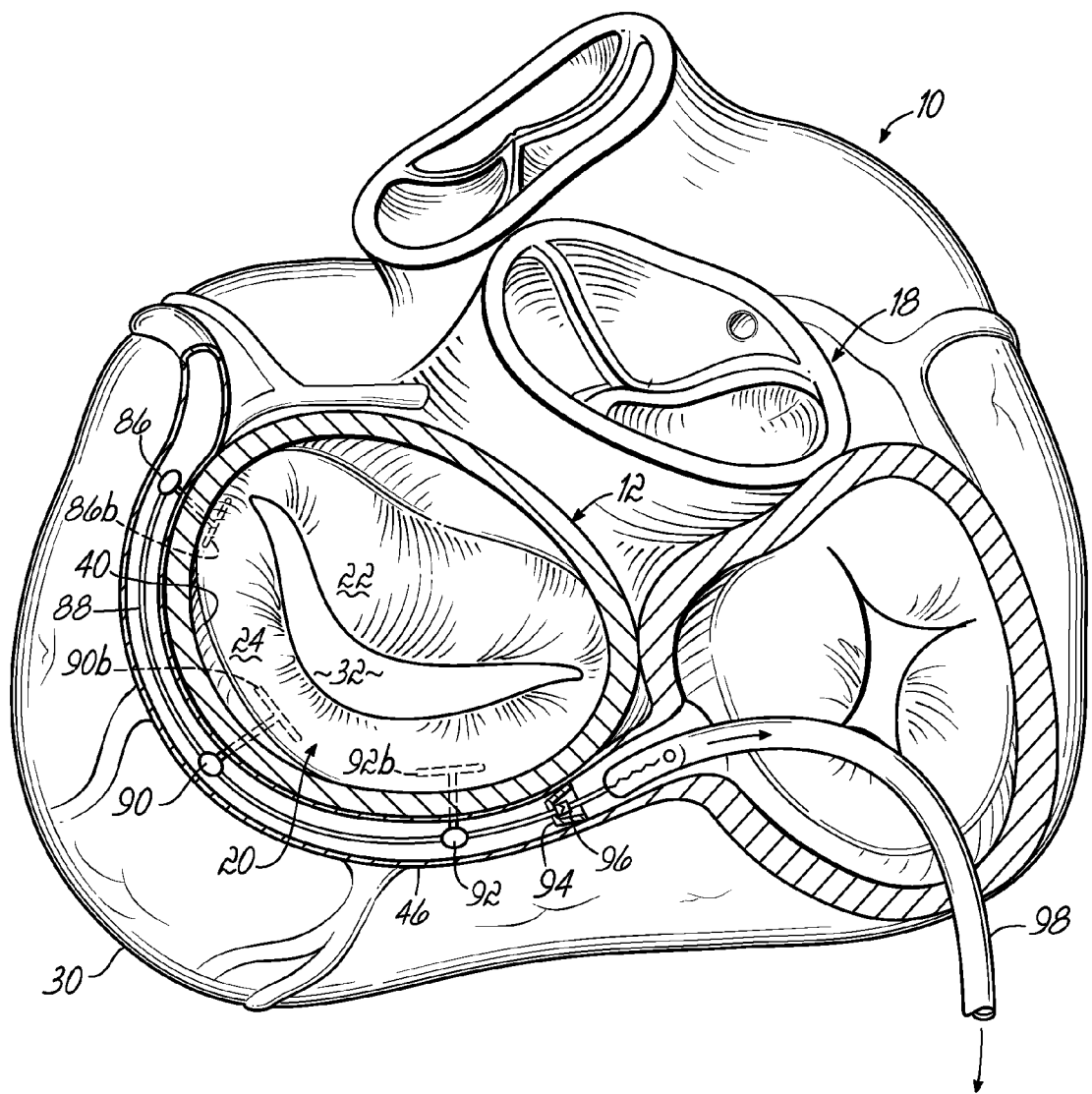
Figures 1, 6E:
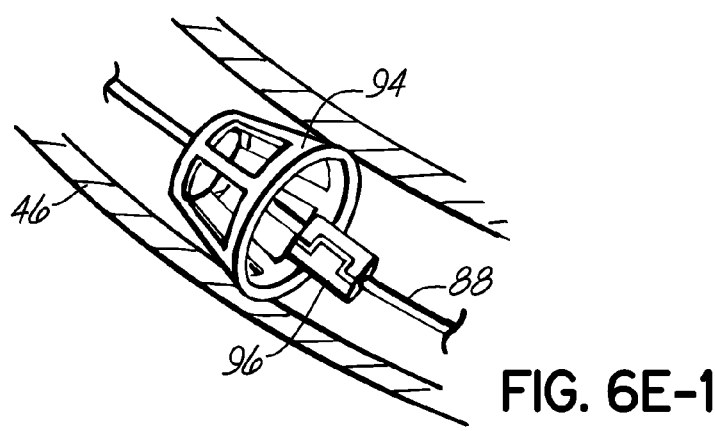
Figure 6F:
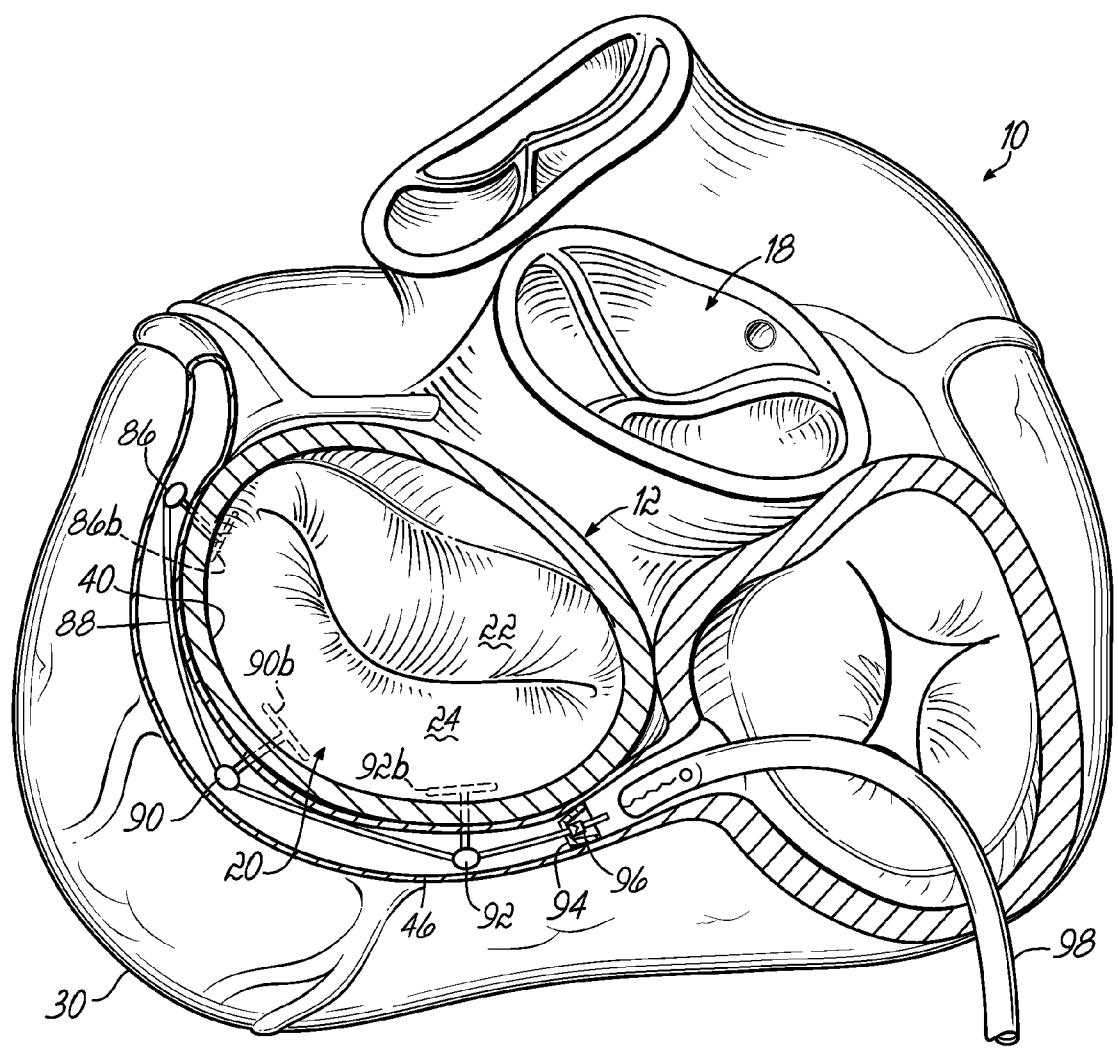
Figures 1, 6F:
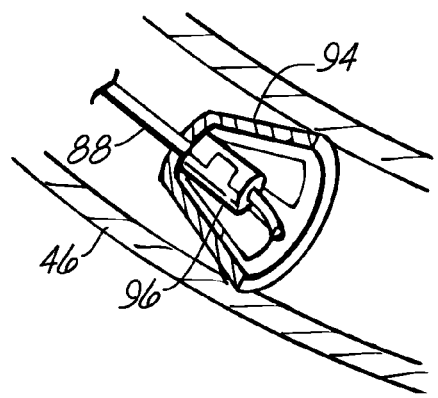

FIGS. 6F and 6F-1 illustrate the final locked positions of the fasteners, flexible tensile member and locking member placed via catheters.

FIGS. 7A-7G are enlarged cross sectional views of the mitral valve at the valve annulus taken generally along line 7-7 of FIG. 6A and showing the placement of a fastener from the CS downwardly through the valve annulus to the underside or left ventricle side of the valve.

Figure 8A:
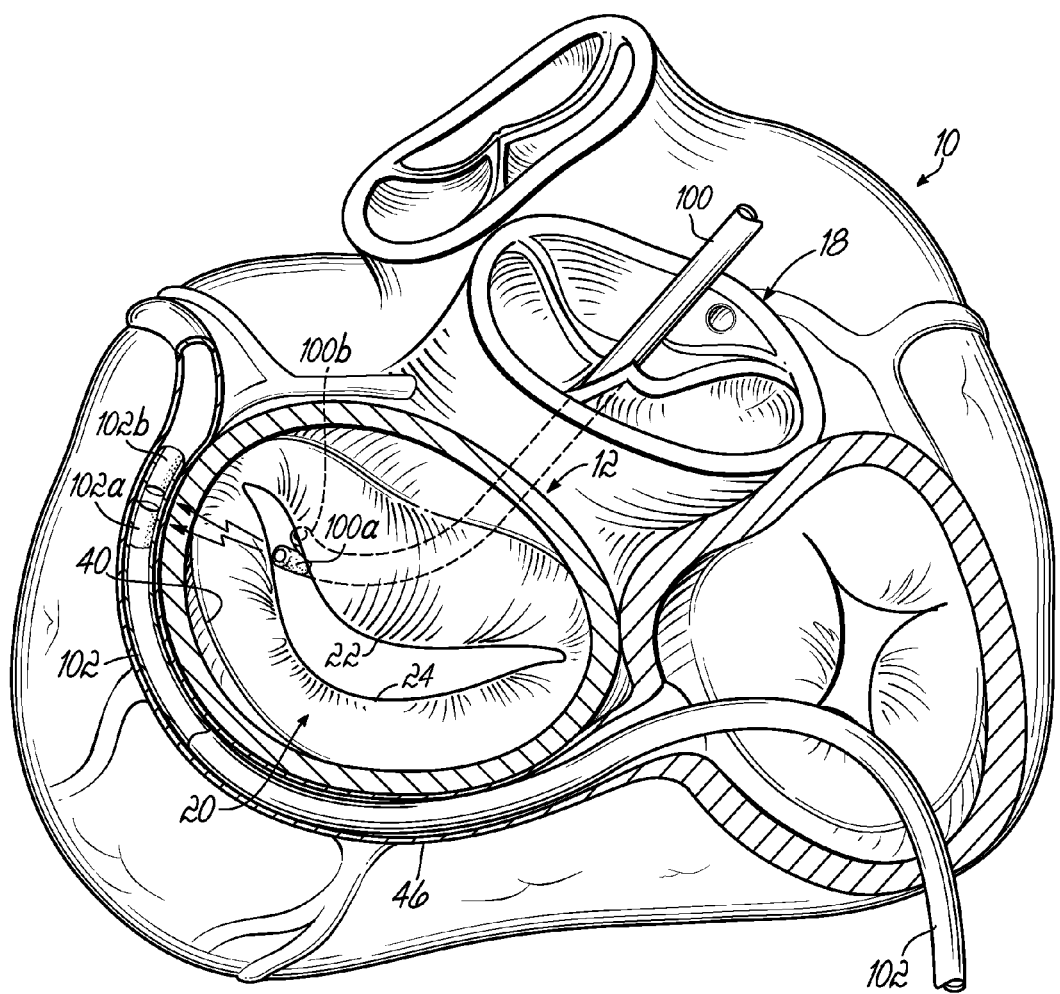
Figure 8B:
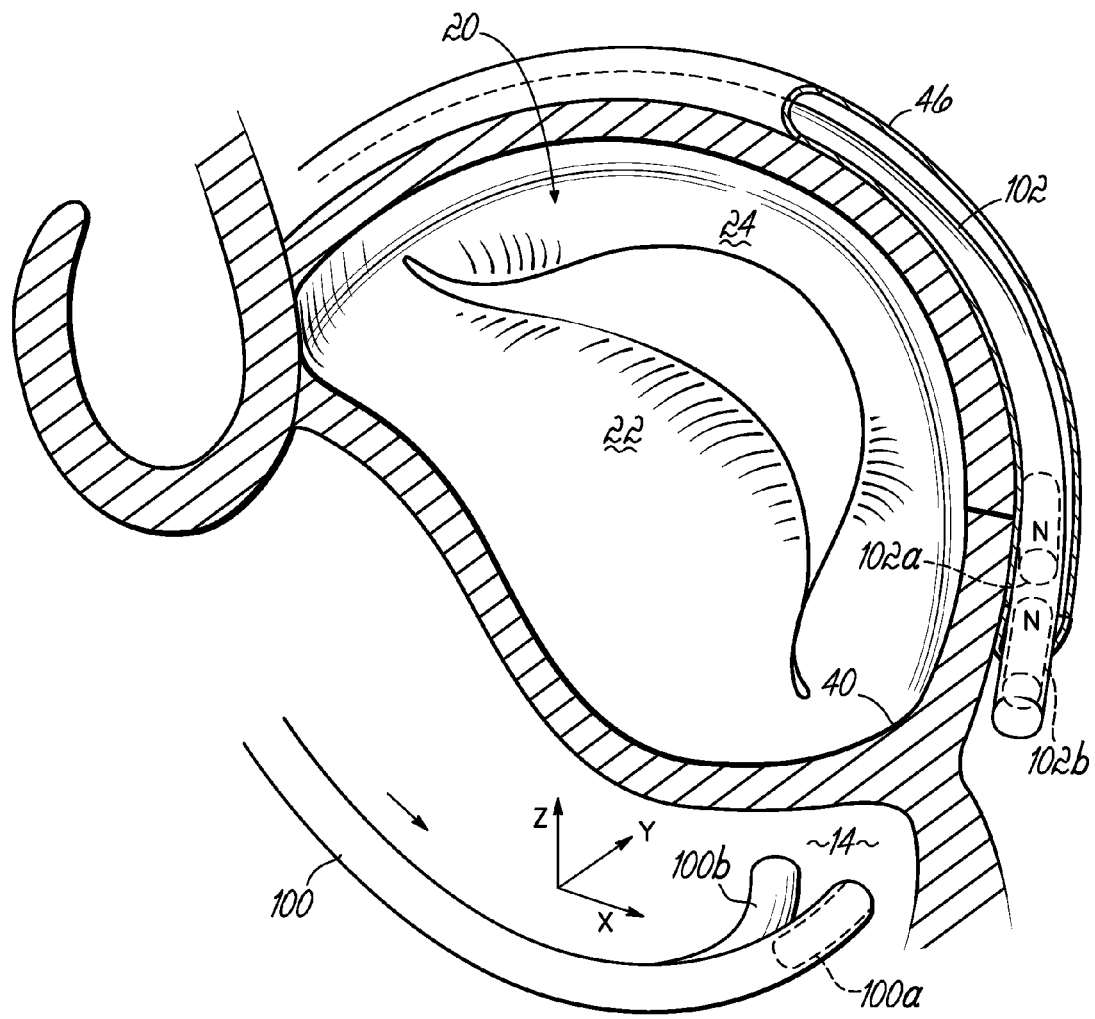

FIGS. 8A and 8B illustrate cross sectional views, respectively, through the CS and illustrating the use of a pair of magnets in the CS for magnetically guiding and locking up with a magnet on an anchor delivery catheter.

Figure 8C:
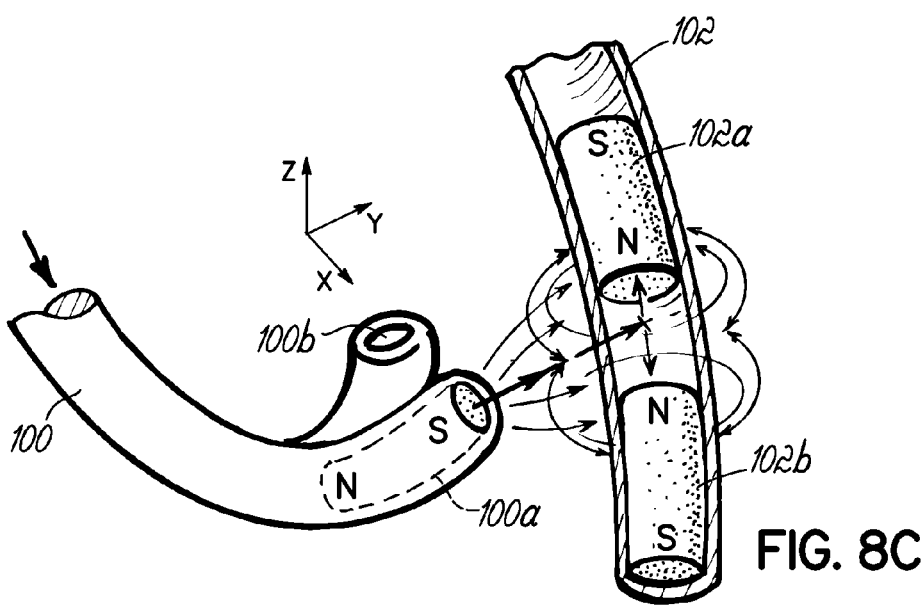

FIG. 8C is an enlarged view of the various magnets and their magnetic fields.

Figure 9:
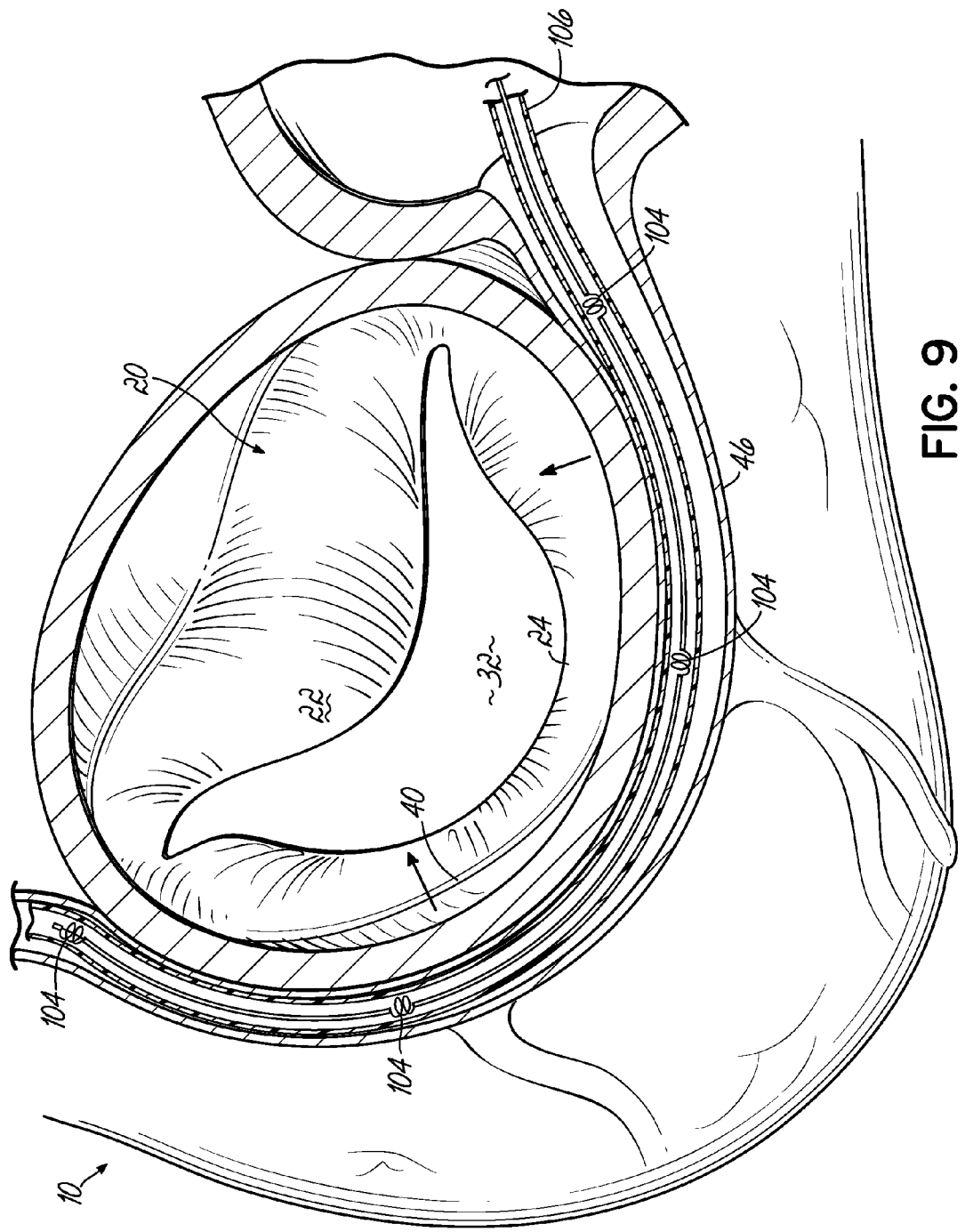

FIG. 9 is a cross sectional view of the heart anatomy through the CS, and illustrating the use of electromagnets in a catheter device.

Figure 10:
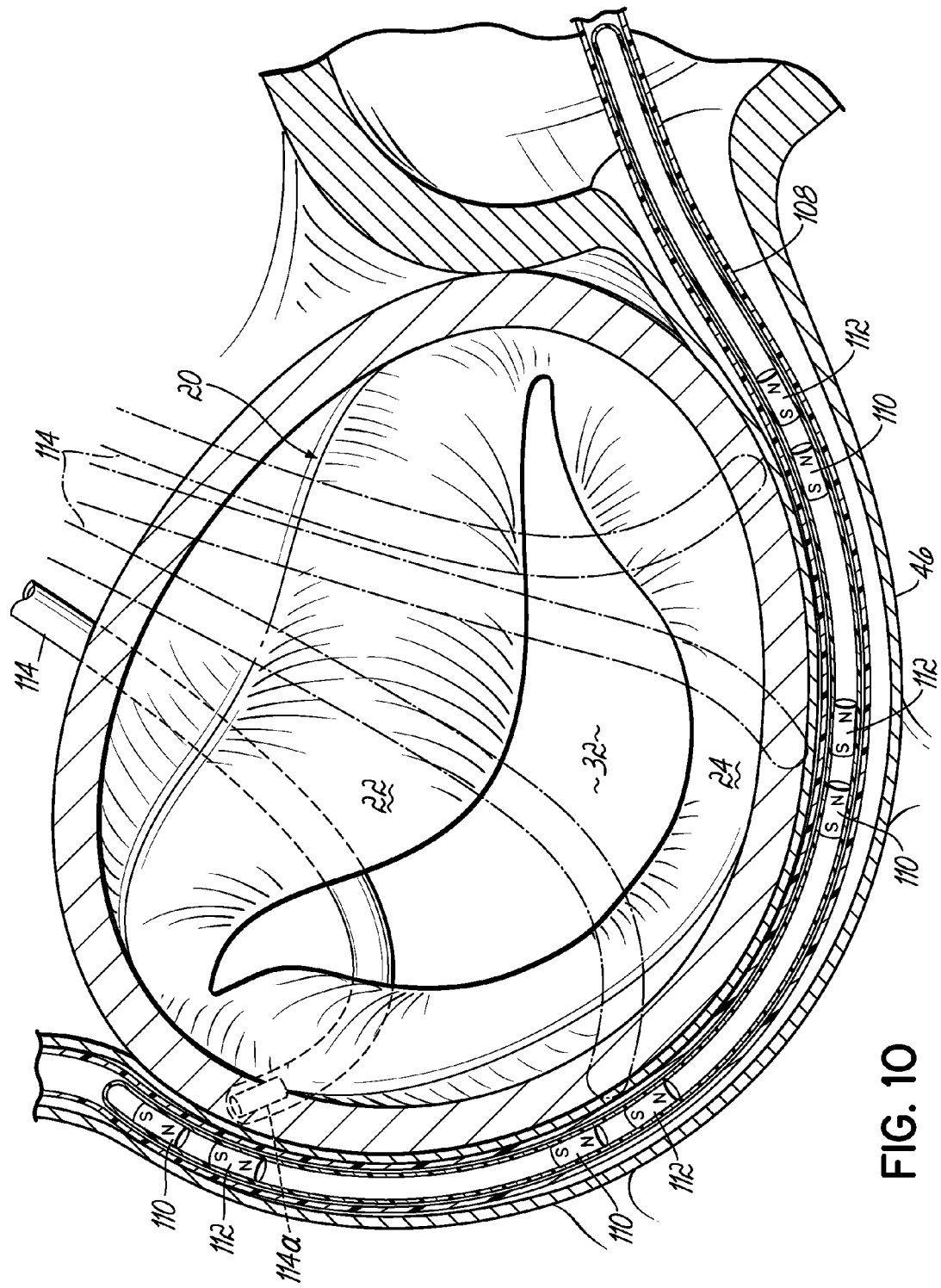

FIG. 10 is a cross sectional view of the heart anatomy through the CS and illustrating the successive positioning of a catheter device relative to another catheter device in the CS through the use of magnets.

FIGS. 11A and 11B illustrate cross sectional views of the heart anatomy through the CS and respectively illustrating nonactivated and activated positions of a series of magnetic fasteners used for correcting a mitral valve insufficiency.

FIGS. 11A-1 and 11B-1 respectively illustrate enlarged views of the magnetic fastener system in its nonactivated and activated states.

Figure 11C:
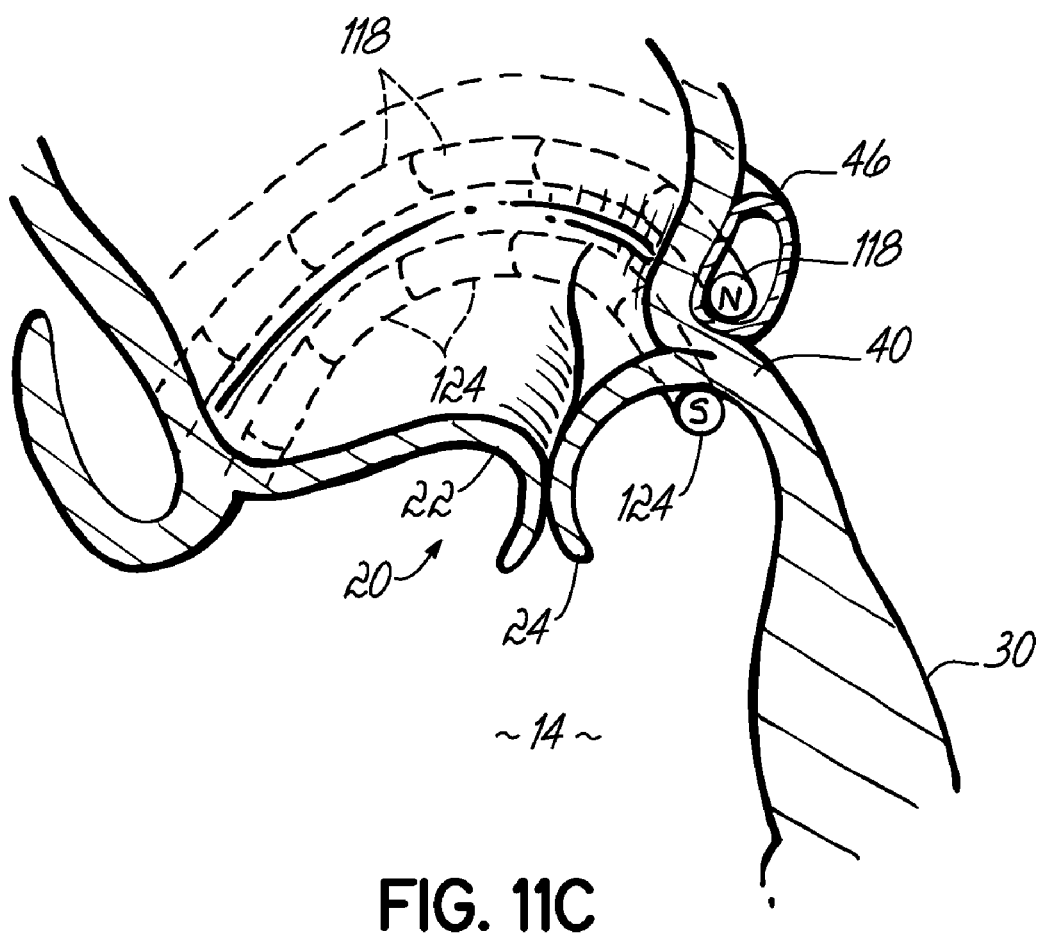

FIG. 11C is a cross sectional view through the mitral valve and CS illustrating the final activated position of the fastener system placed in accordance with FIGS. 11A and 11B.

Figure 12A:
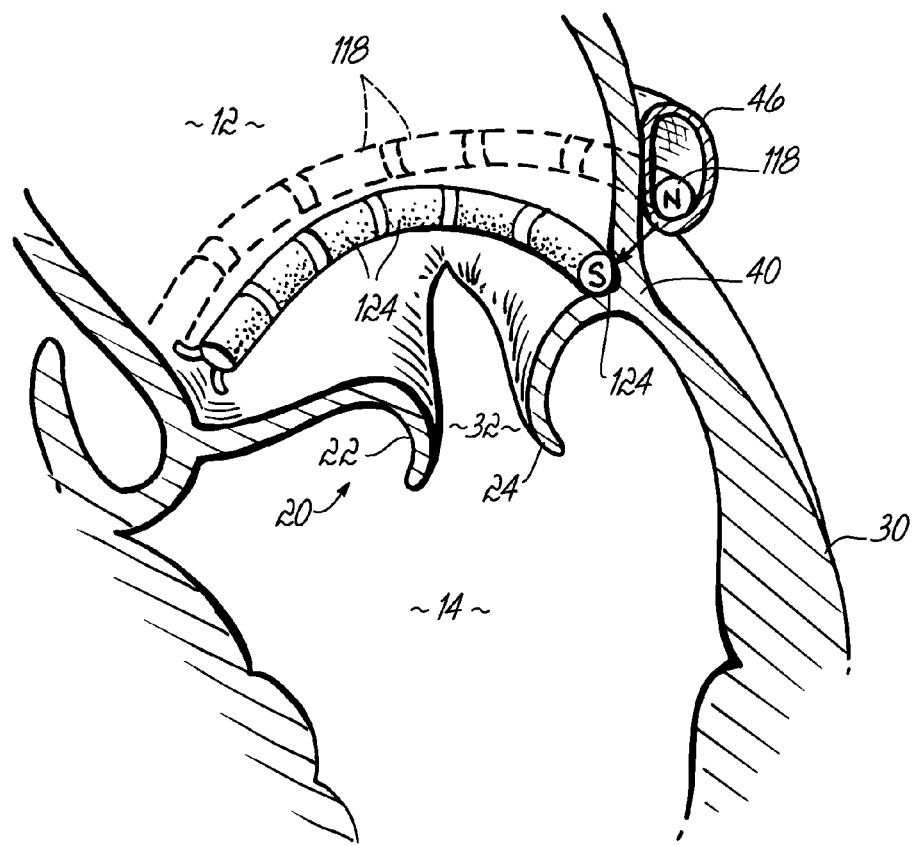
Figure 12B:
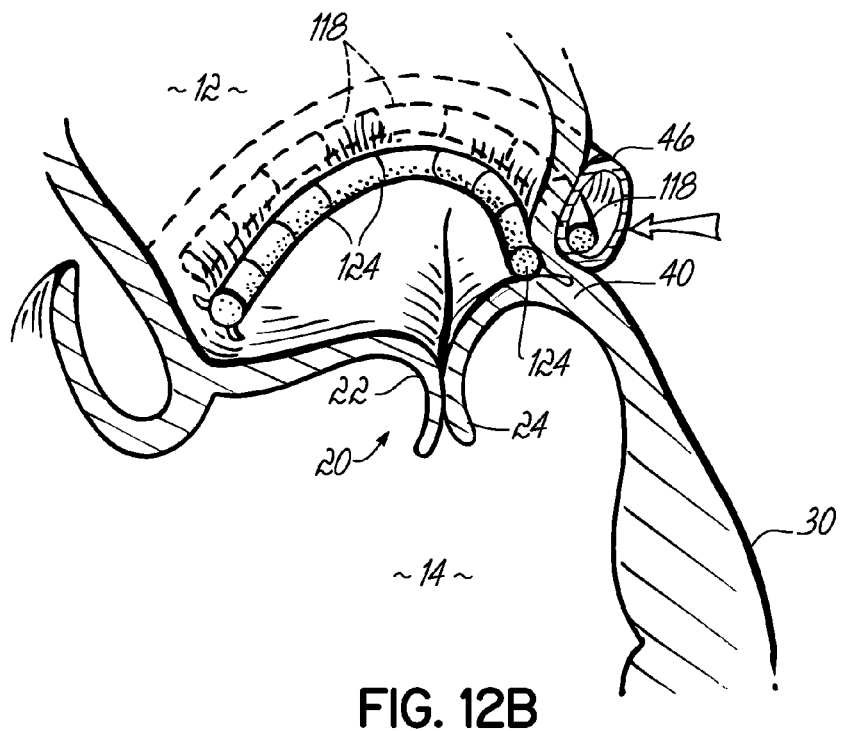

FIGS. 12A and 12B illustrate an alternative in which the magnetic fasteners are placed respectively in the CS and in the left atrium.

Figure 13A:
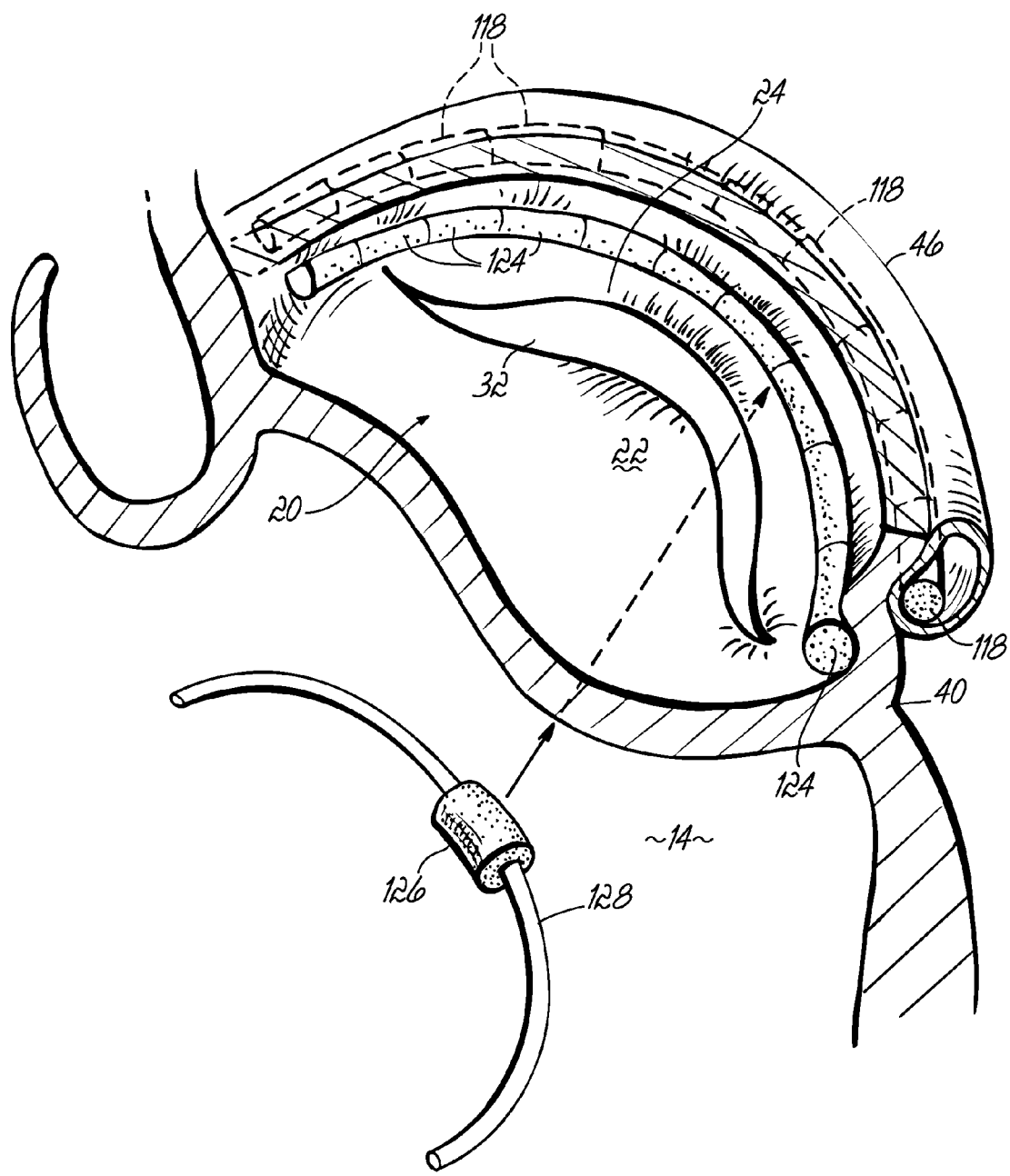
Figure 13B:
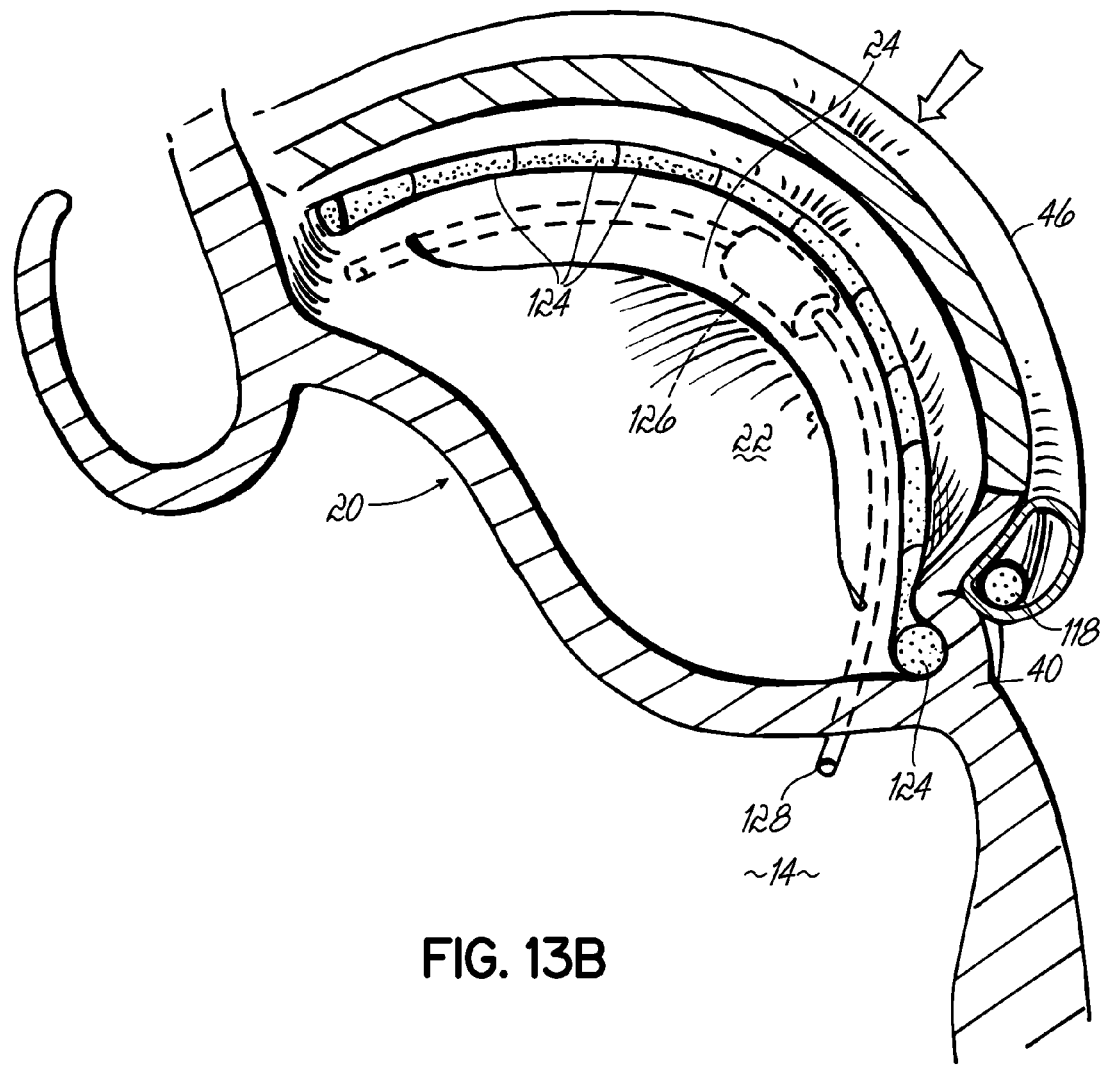

FIGS. 13A and 13B are cross sections of the heart anatomy through the CS and illustrating an additional magnetic fastener placed below the annulus in left ventricle to assist with reducing the mitral valve insufficiency.

Figure 14A:
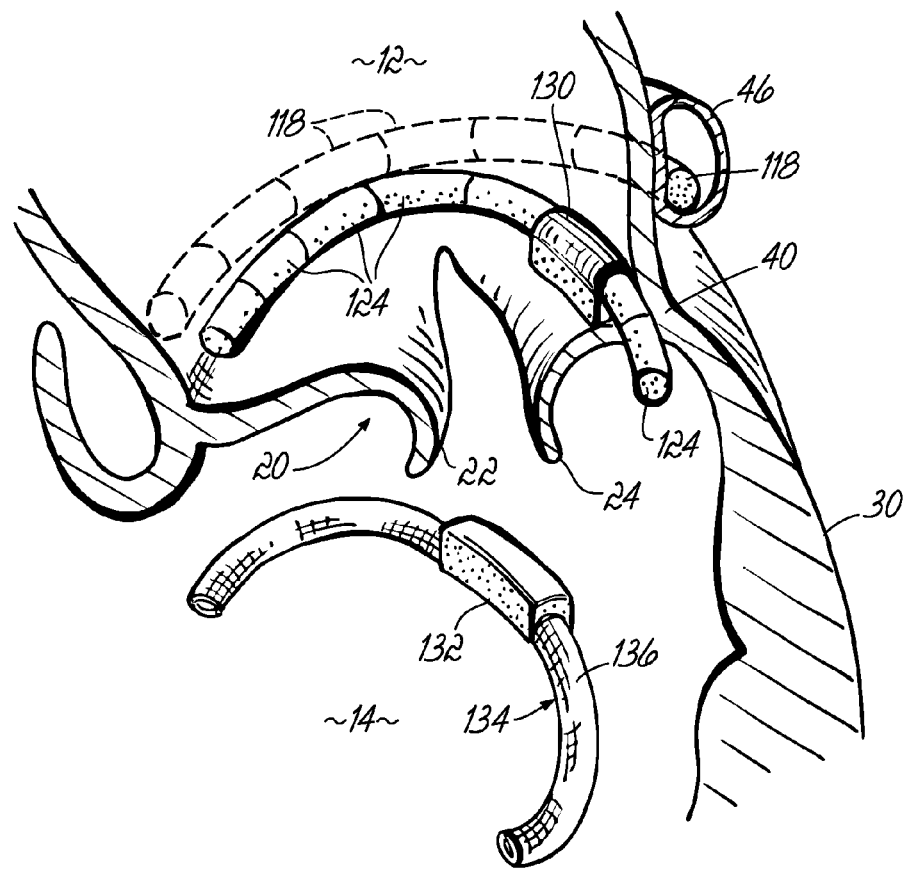
Figure 14B:
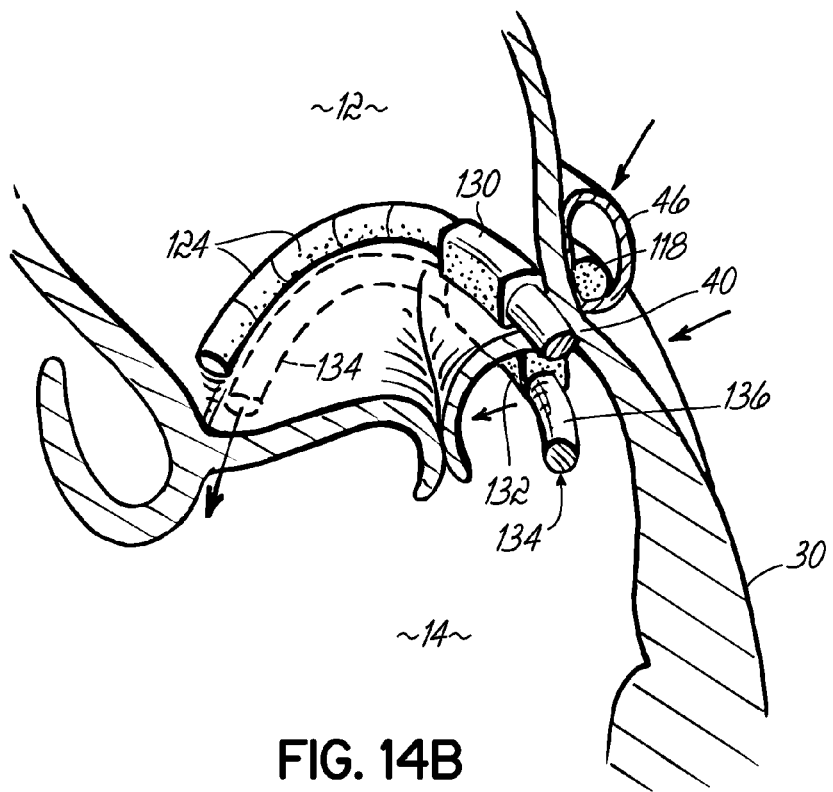

FIGS. 14A and 14B are cross sections through the CS and mitral valve and illustrating another alternative magnetic fastening system.

Figure 14C:
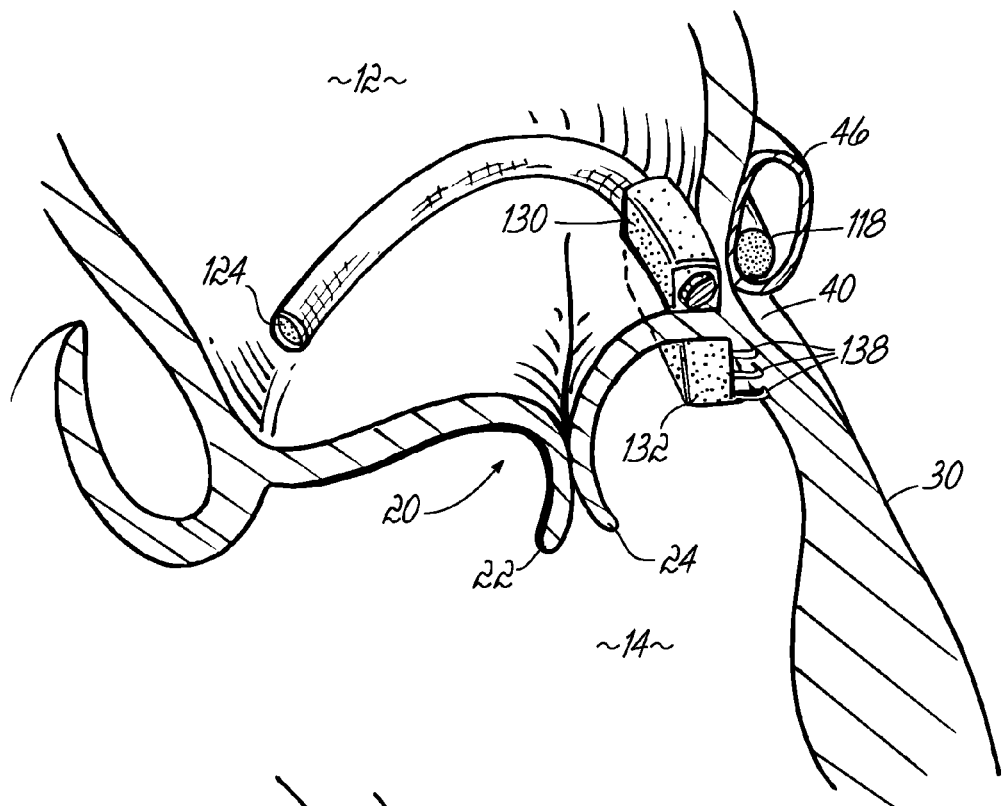

FIG. 14C is similar to FIG. 14B, but illustrates a magnetic fastener with additional mechanical fastening elements in the form of projections which engage and penetrate tissue proximate the valve annulus.

Figure 14D:
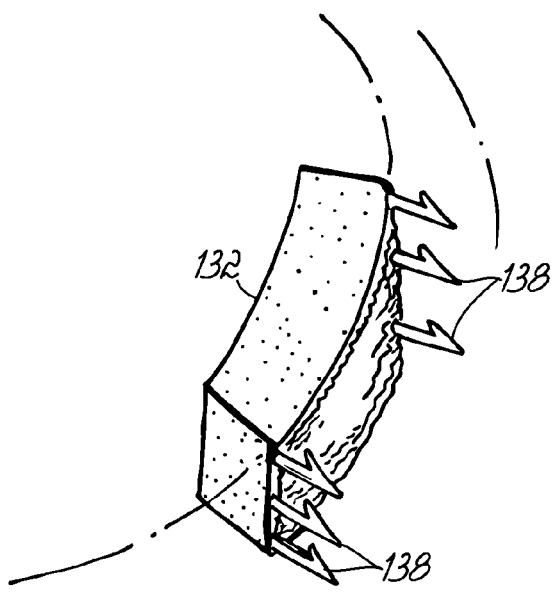
Figure 14E:
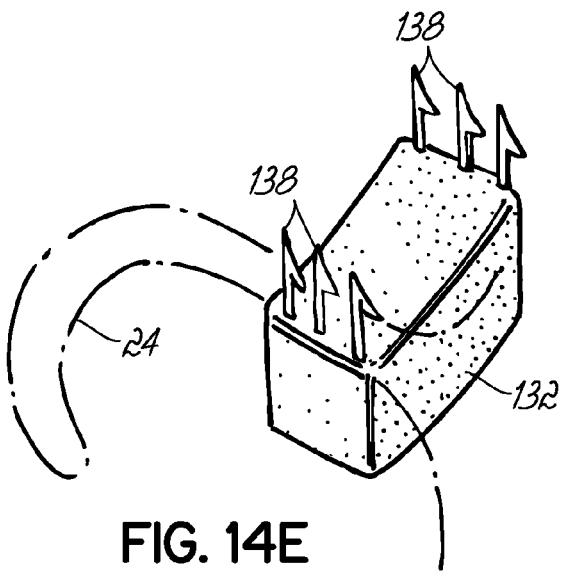

FIGS. 14D and 14E are perspective views illustrating the magnetic fastening elements with mechanical tissue engaging projections.

FIGS. 15A-15C are cross sections through the CS and mitral valve illustrating an alternative fastener delivery mechanism in which a fastener is delivered through a catheter and also through magnetic guiding elements.

Figure 15D:
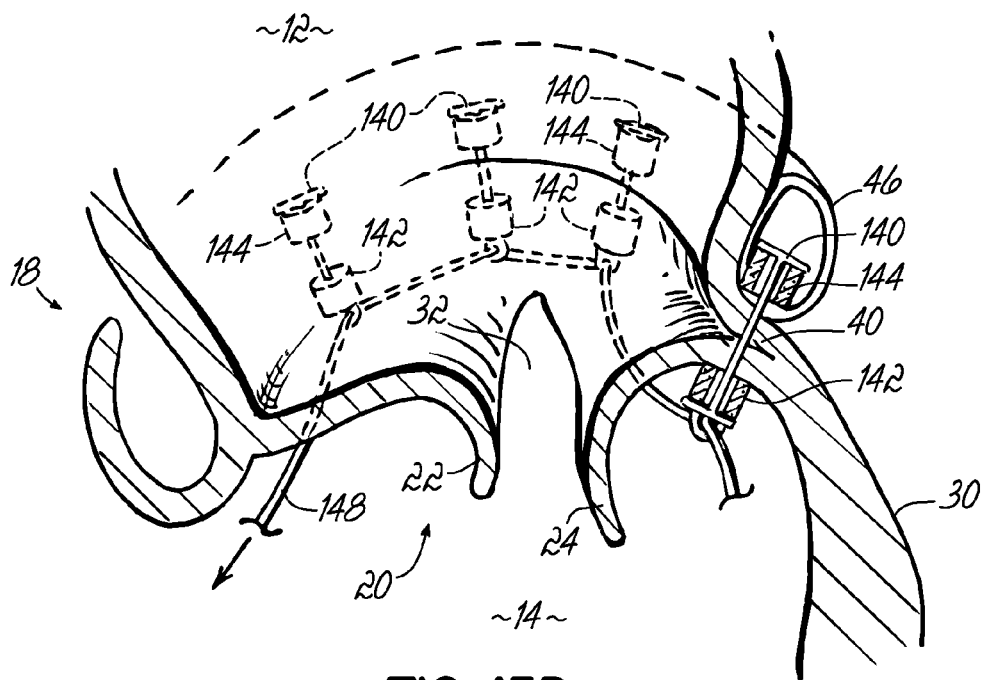
Figure 15E:
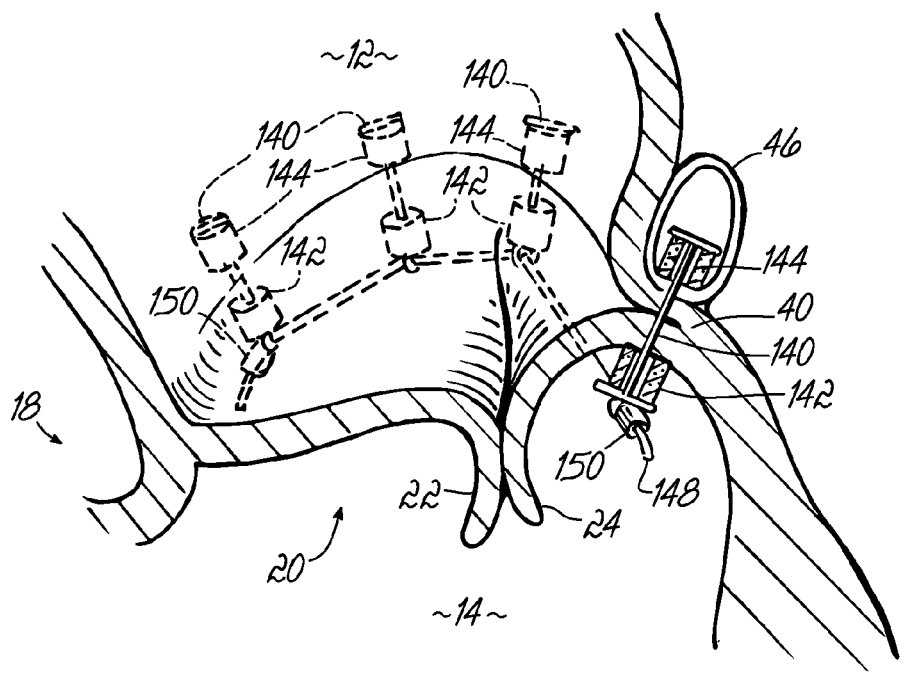

FIGS. 15D and 15E are cross sections similar to FIG. 15A, but illustrating a series of fasteners delivered through magnetic guiding elements and daisy chained together using a flexible tensile member.

Figure 16A:
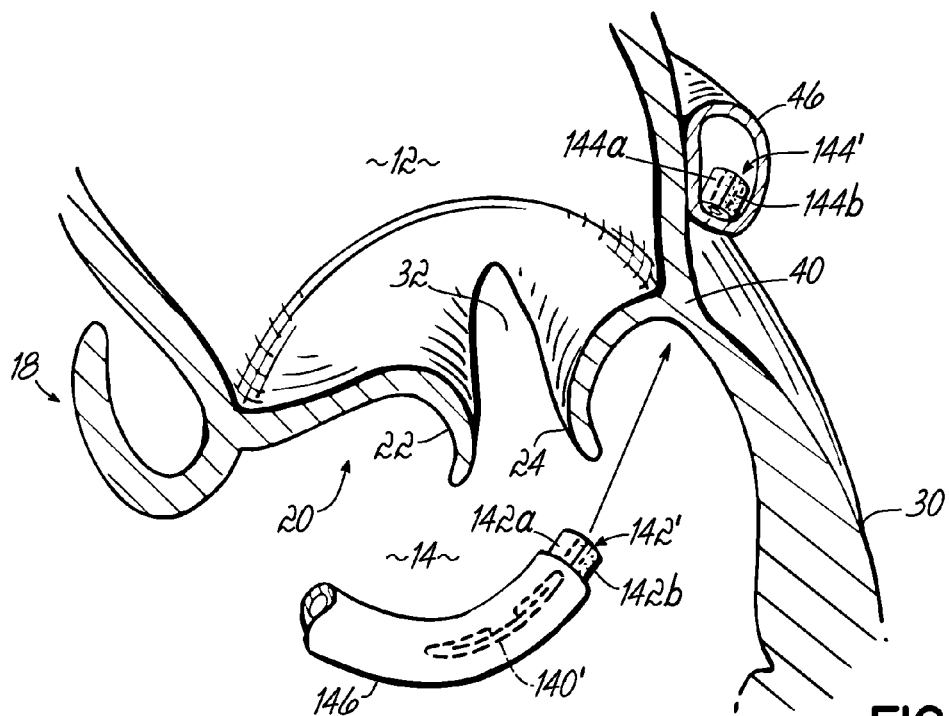
Figures 1, 16A:
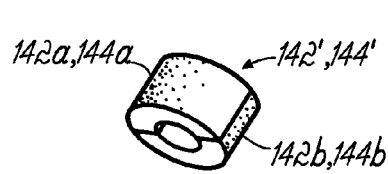
Figures 2, 16A:
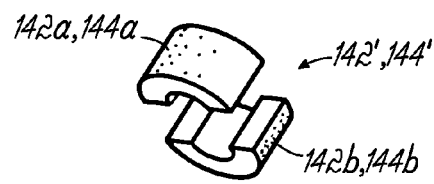
Figure 16B:
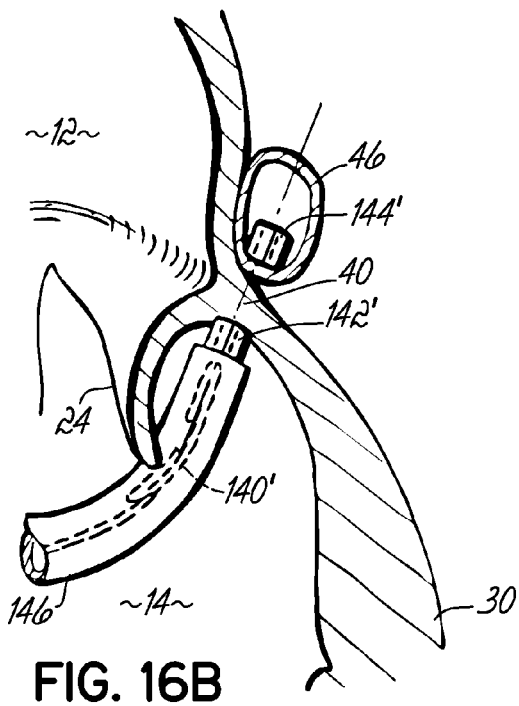
Figure 16C:
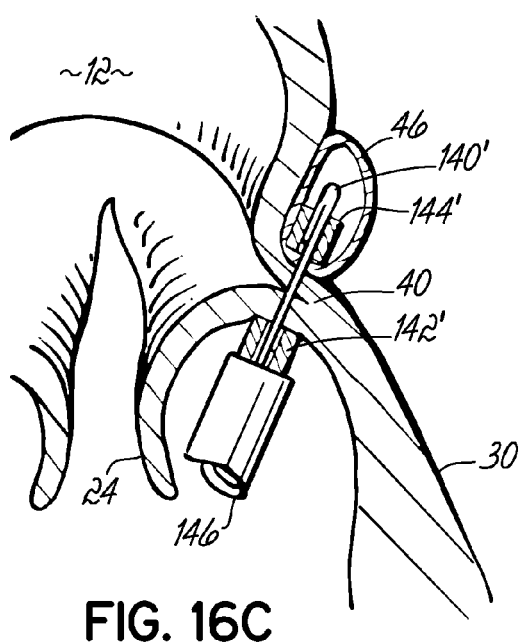

FIGS. 16A-16C are cross sectional views similar to FIGS. 15A-15C, but illustrating the use of magnetic guiding elements which have separable portions.

FIGS. 16A-1 and 16A-2 are perspective views of the magnetic guiding elements respectively shown in nonseparated and separated positions.

Figure 16D:
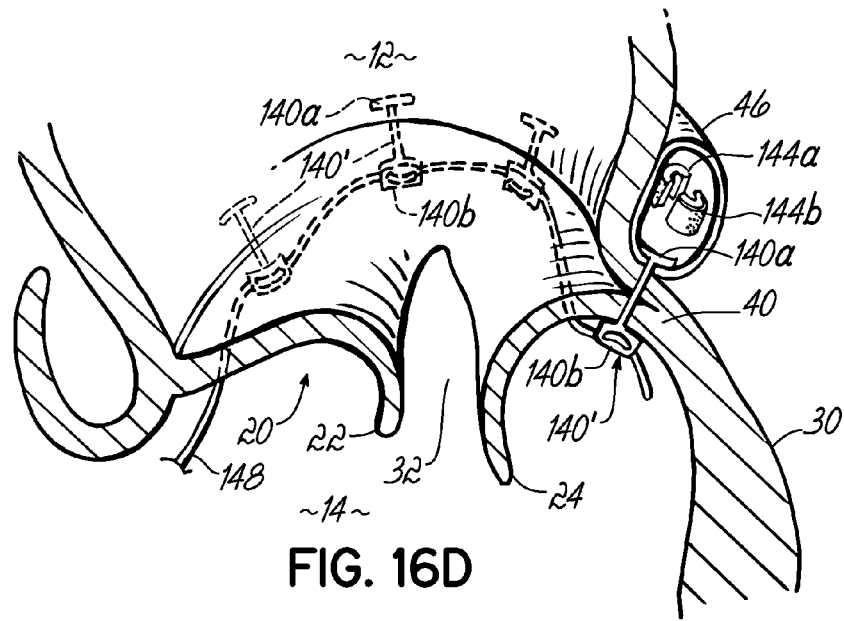
Figure 16E:
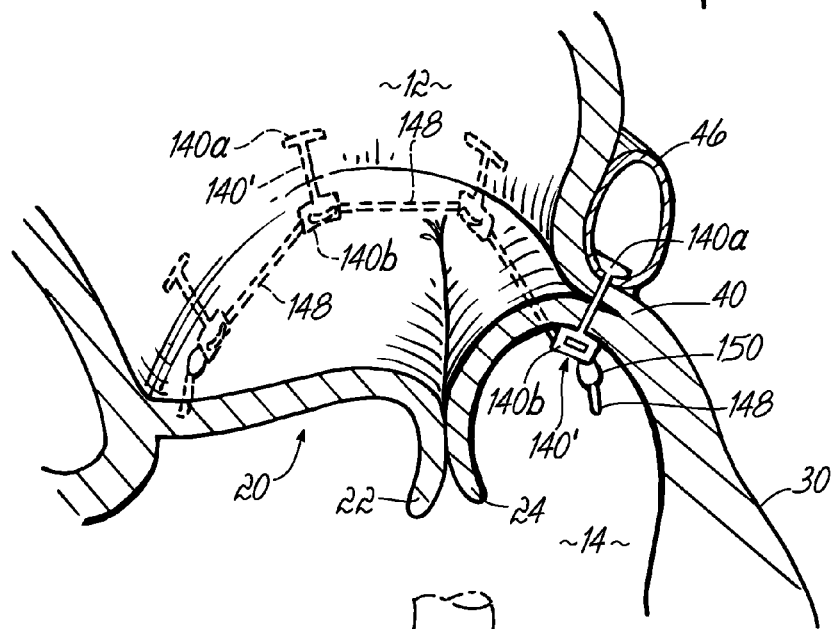

FIGS. 16D and 16E are similar to FIGS. 15D and 15E, and illustrate the daisy chained connection of the fasteners with the magnetic guiding elements removed.

Figure 17:
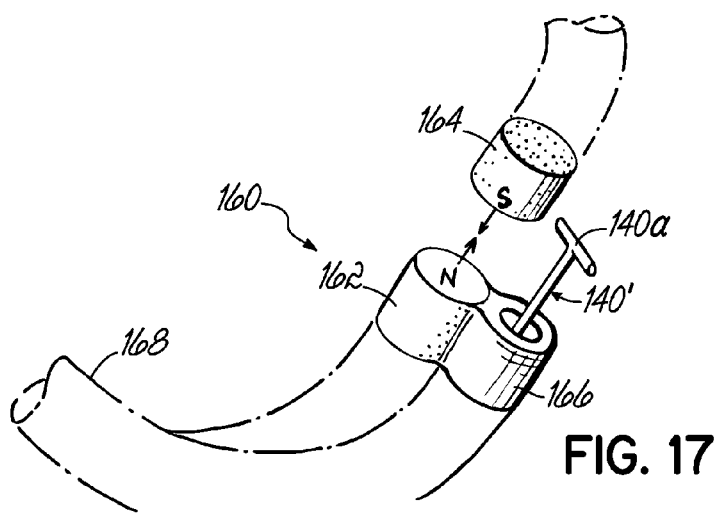

FIG. 17 is a perspective view showing a fastener delivery mechanism on a catheter which includes a magnetic guiding element magnetically coupled to a second magnetic guiding element of a second catheter.

Figure 18A:
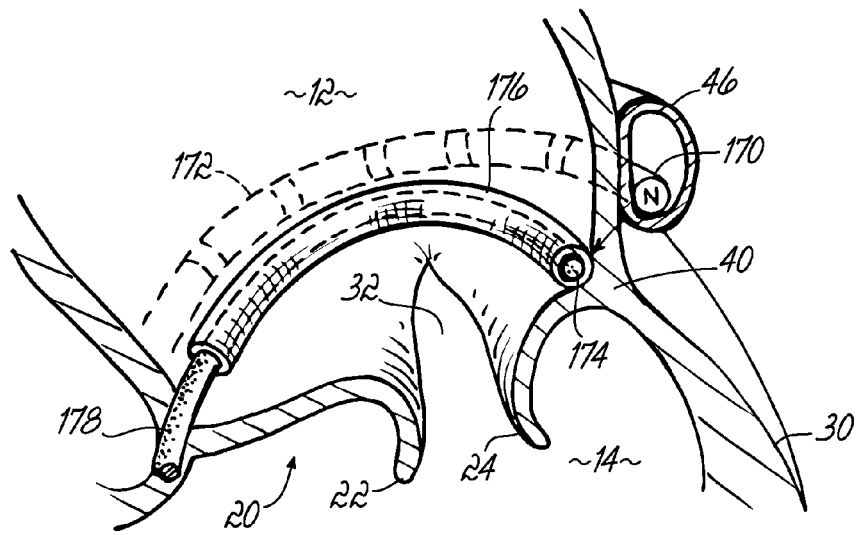
Figure 18B:
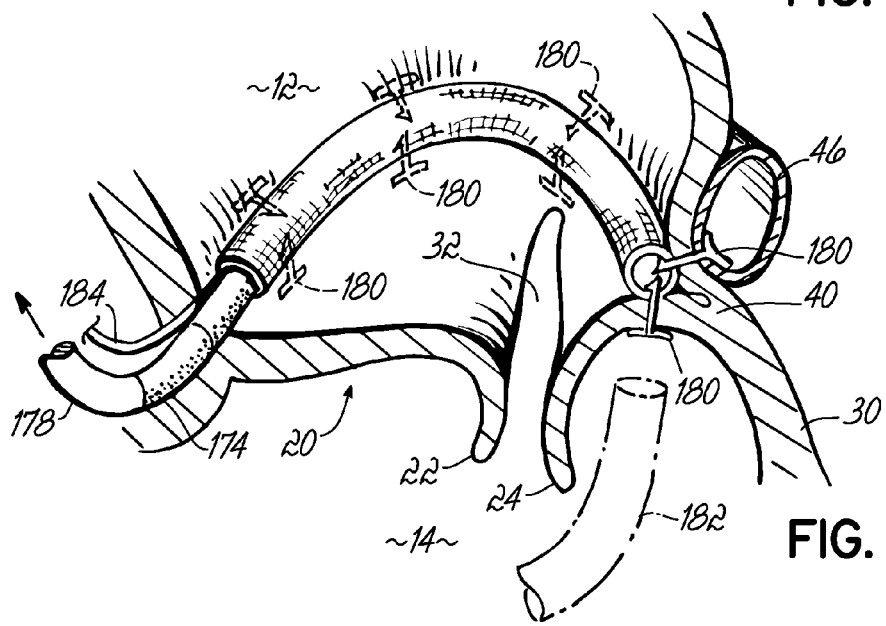
Figure 18C:
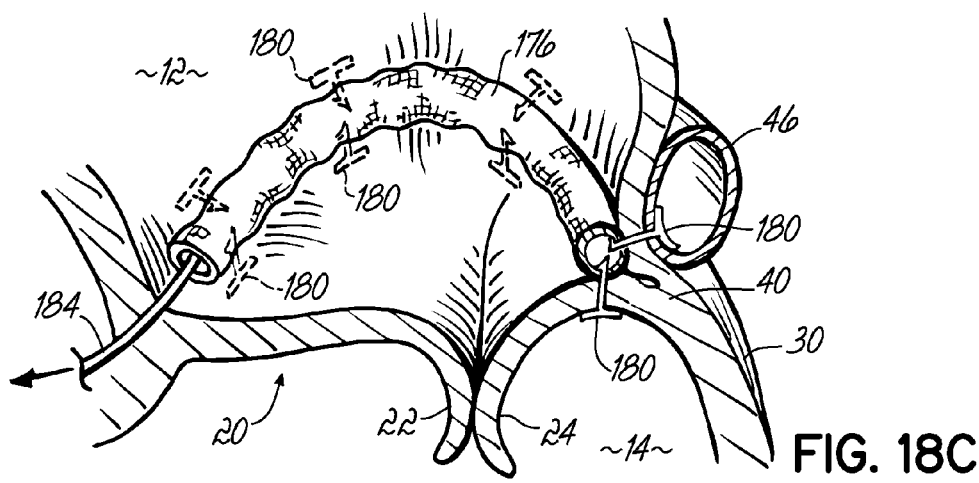

FIGS. 18A-18C respectively illustrate cross sectional views of the heart anatomy through the CS and the mitral valve and the placement of an alternative catheter delivered fastening system.

Figure 19A:
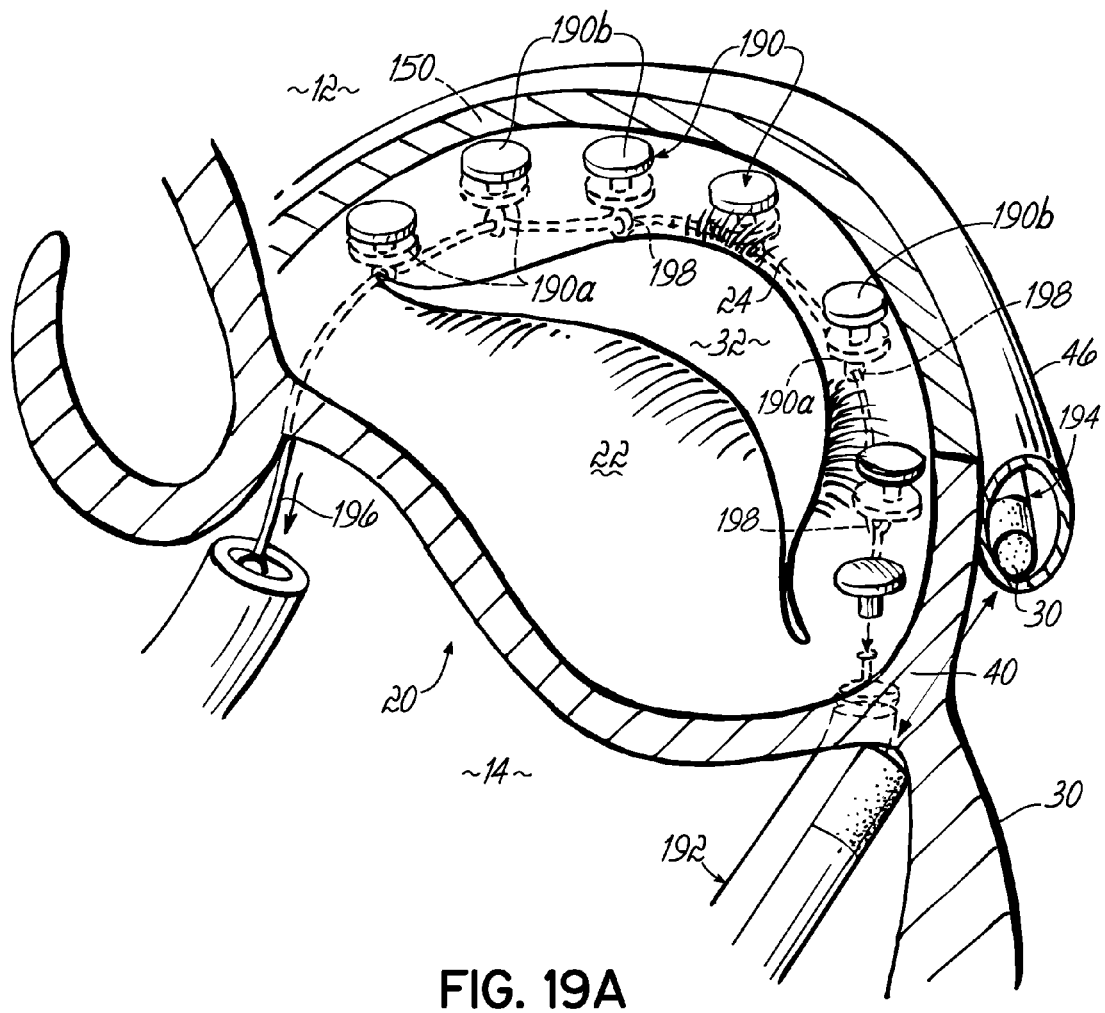

FIG. 19A is a cross sectional view of the heart anatomy through the CS and the placement of another alternative catheter delivered fastening system.

Figure 19B:
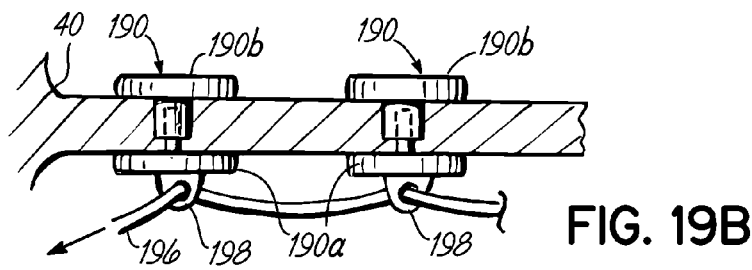
Figure 19C:
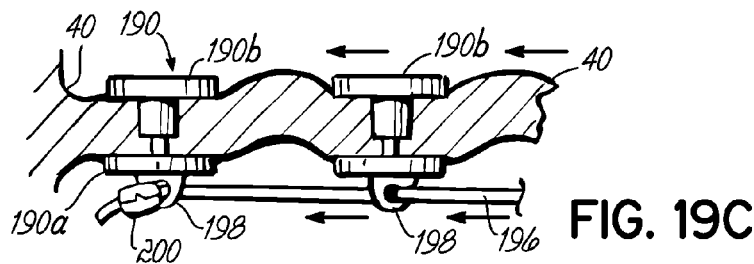

FIGS. 19B and 19C illustrate the daisy chained fasteners of FIG. 19A respectively before and after cinching of the fasteners to shorten the valve annulus.

Figure 20A:
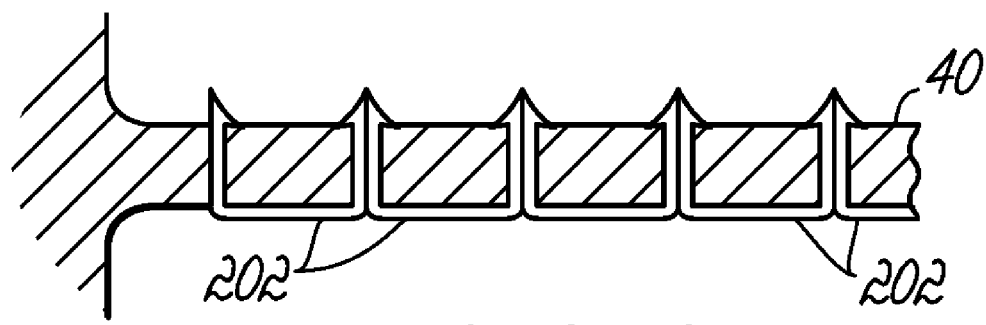
Figure 20B:
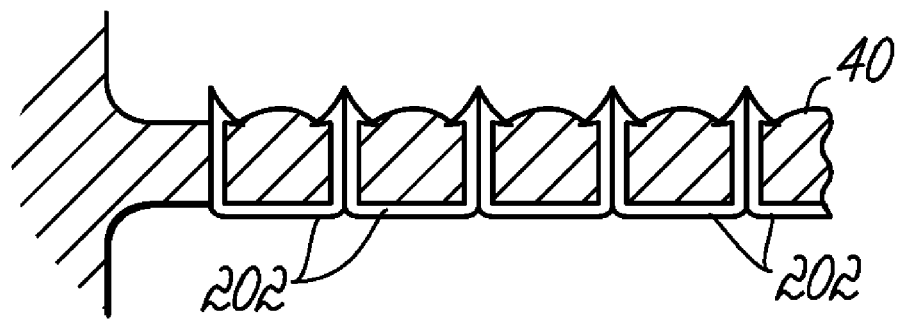

FIGS. 20A and 20B illustrate a cross sectional view of tissue receiving fasteners formed from shape memory alloy both before and after activation of the shape memory effect to shorten the overall length of the tissue engaged with the fasteners.

Figure 21A:
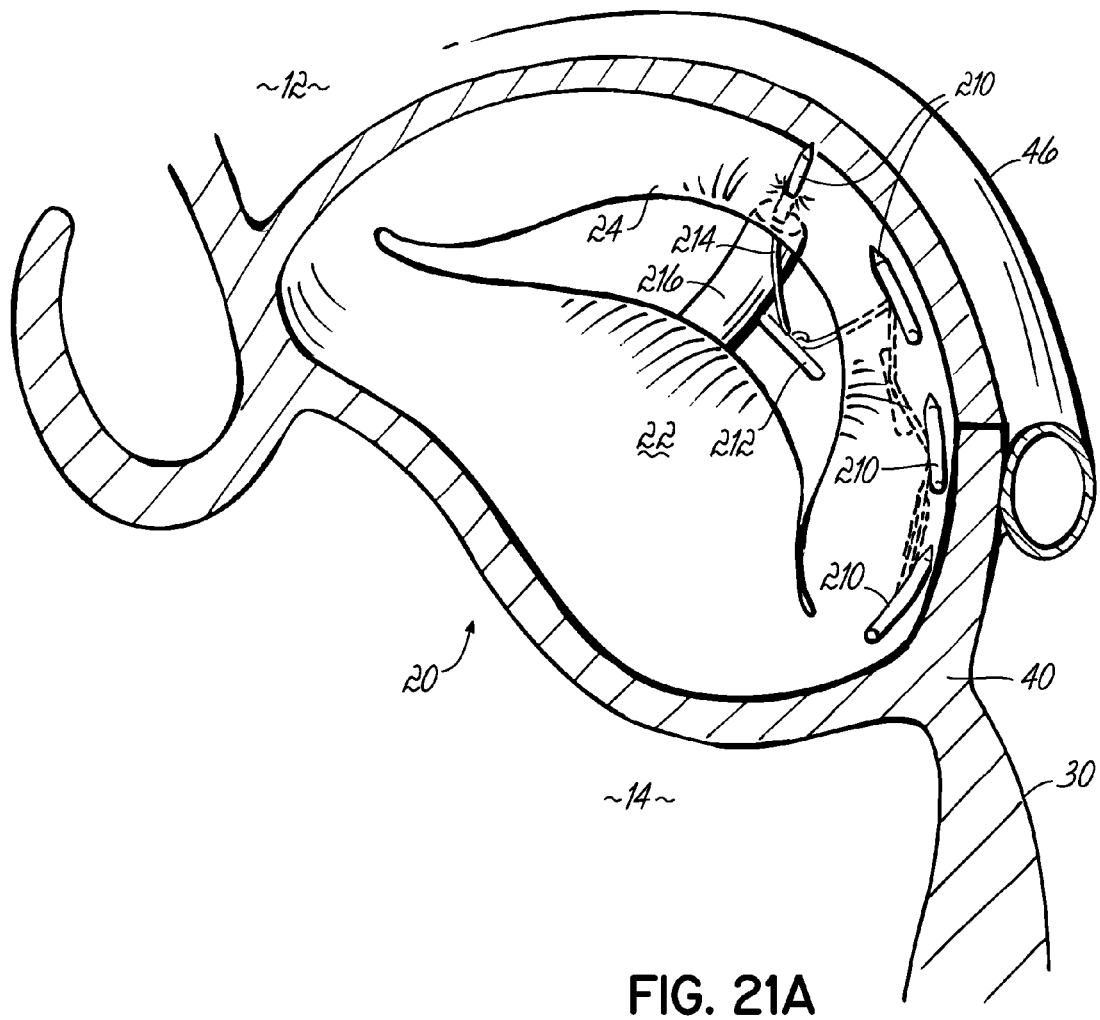

FIG. 21A is a cross sectional view of the heart anatomy through the CS and illustrating the use of a catheter to delivery a series of fasteners in the form of tissue penetrating fasteners separated by pledgets along a flexible tensile member.

Figure 21B:
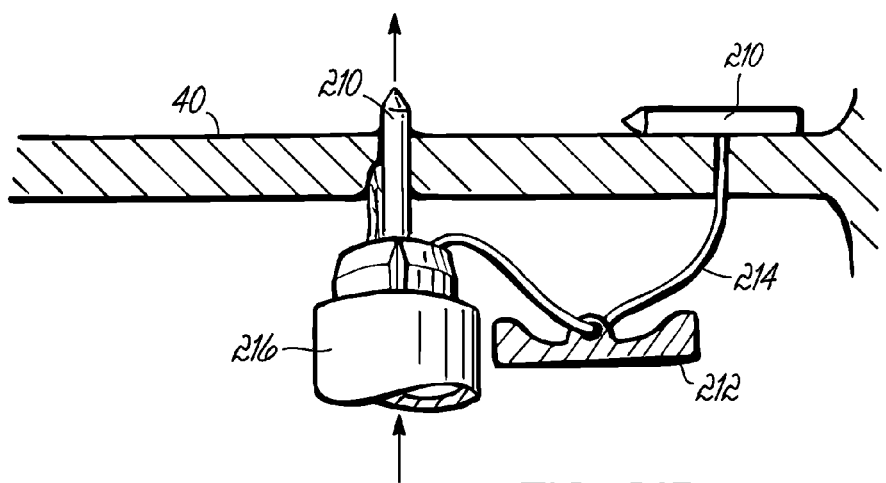
Figure 21C:
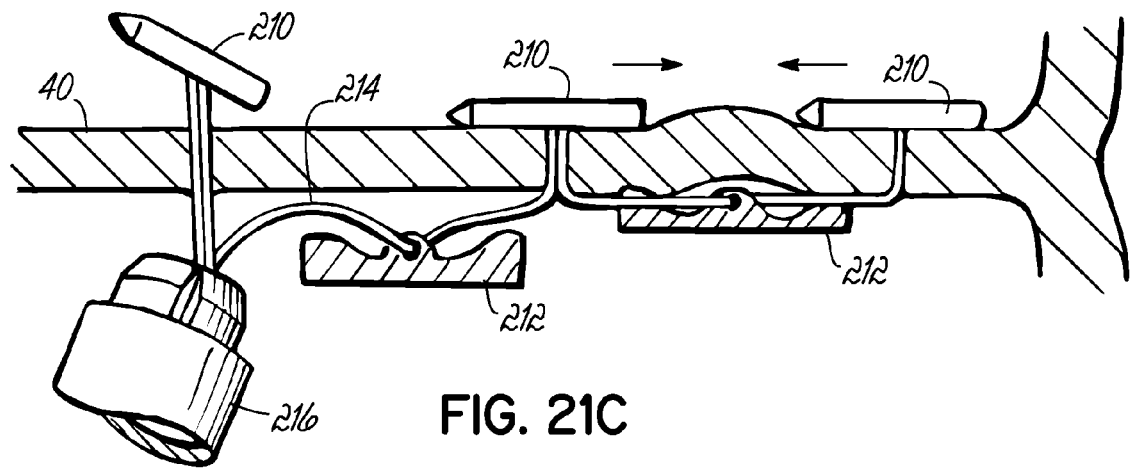
Figure 21D:
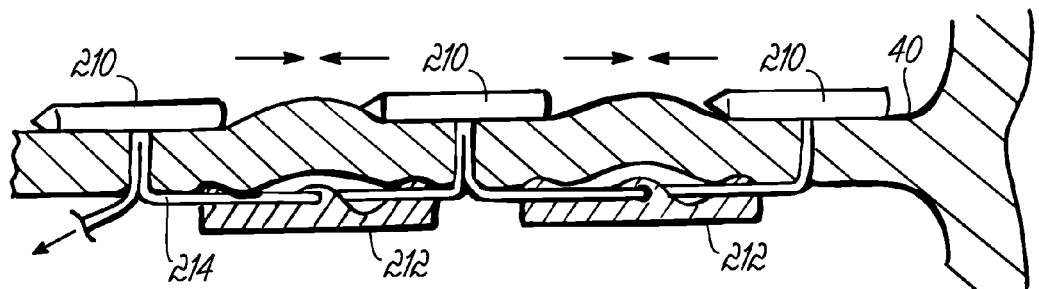

FIGS. 21B-21D respectively illustrate enlarged views of the fastener delivery system shown in FIG. 21A as well as the final cinching thereof.

Figure 22:
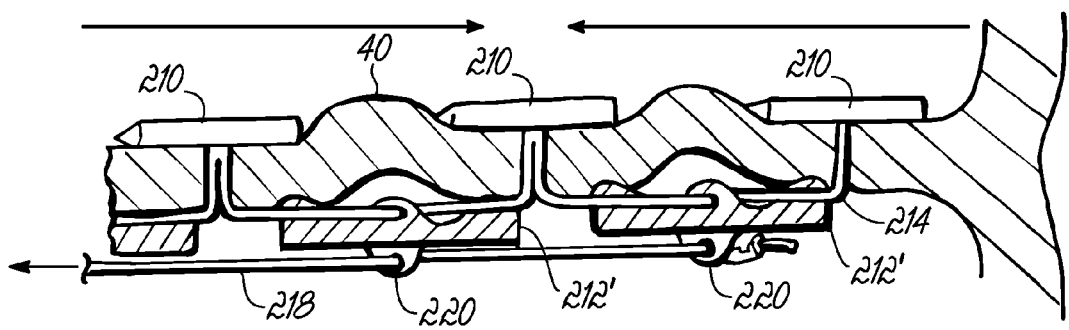
Figure 23A:
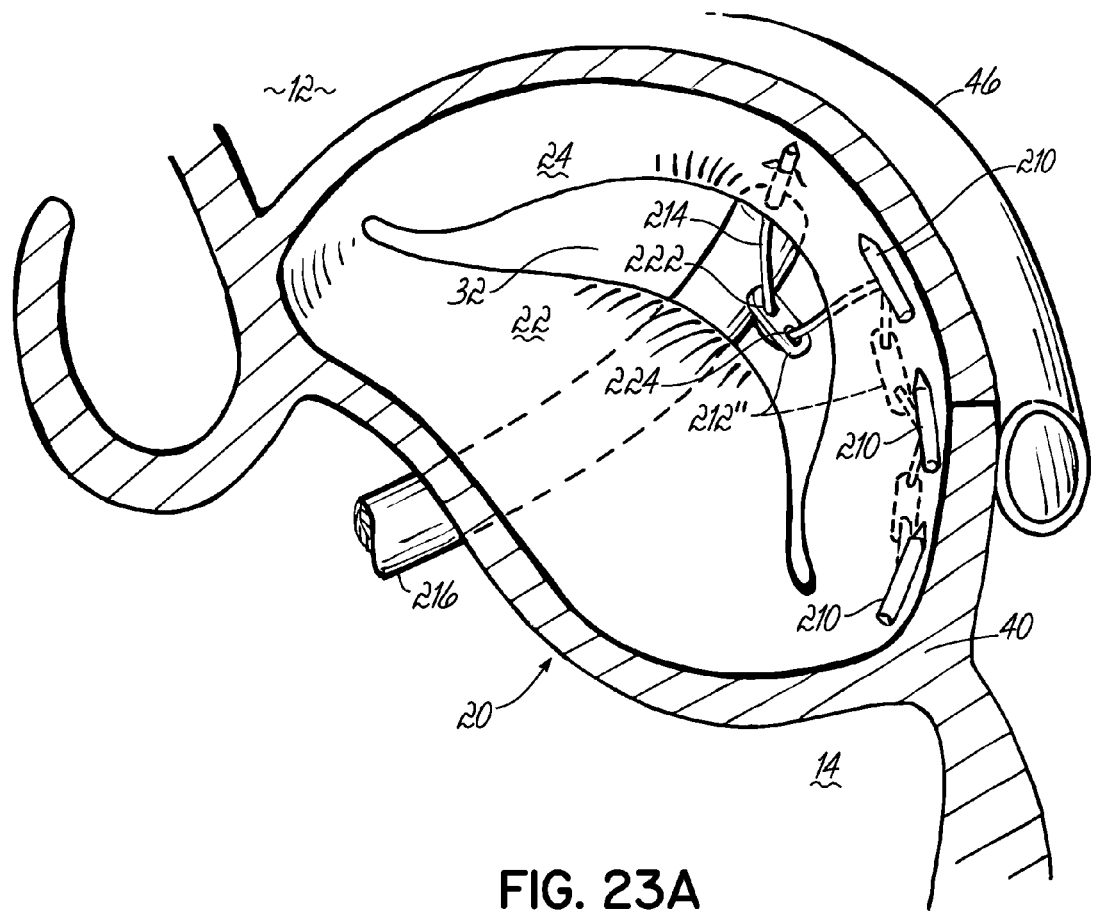
Figure 23B:
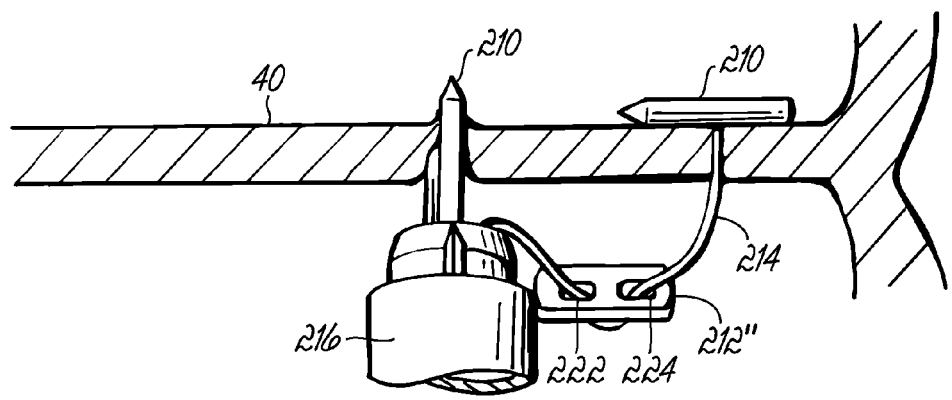
Figure 23C:
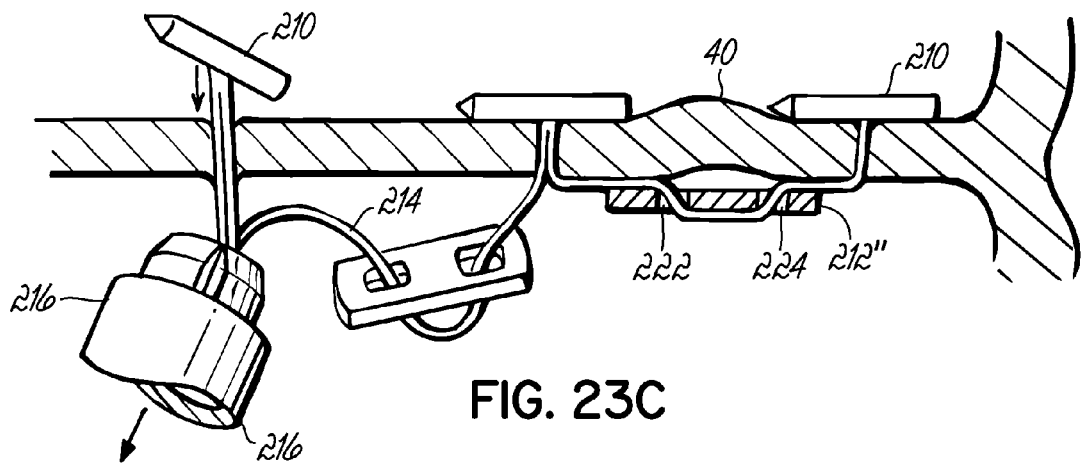
Figure 23D:
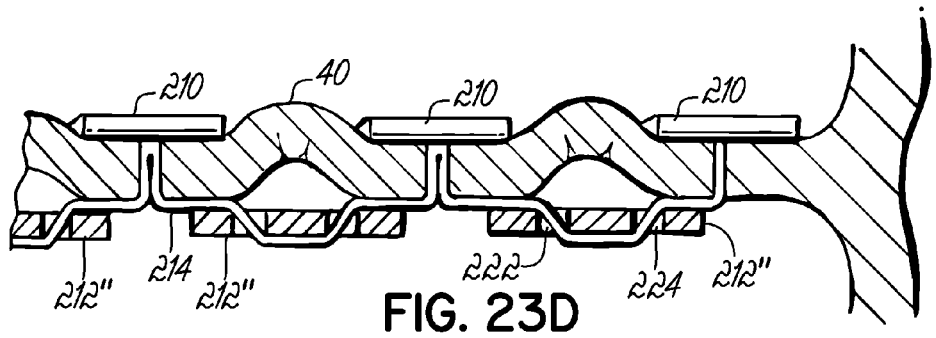
Figure 23E:
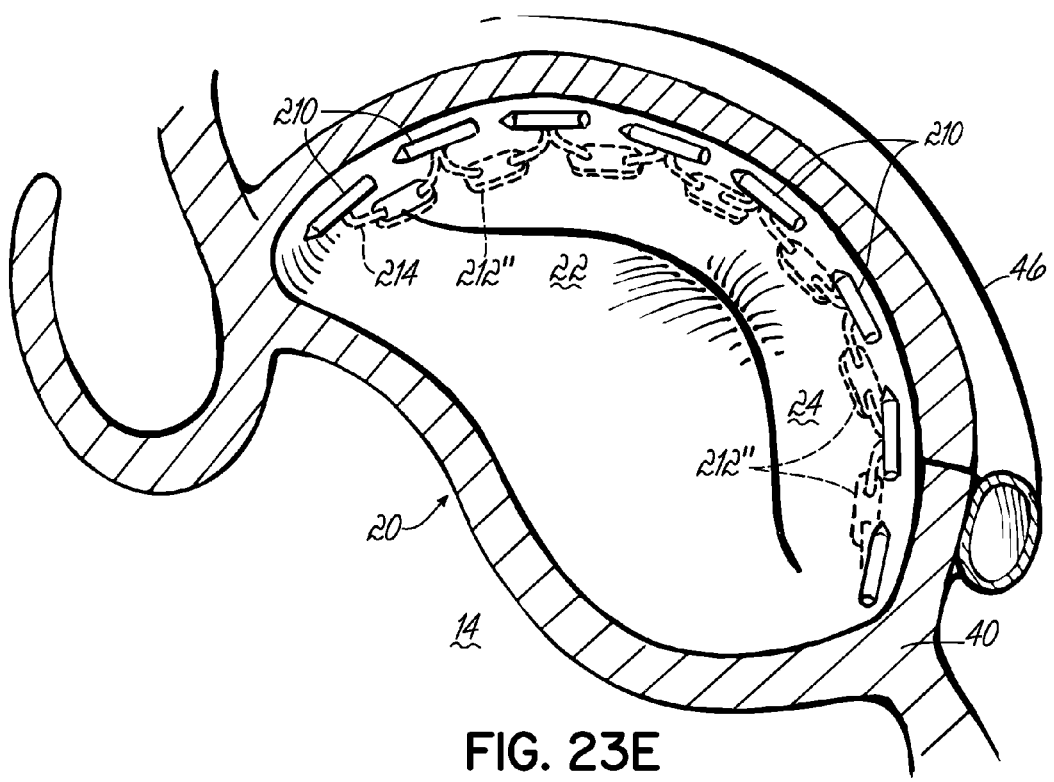

FIG. 22 illustrates an alternative system to FIGS. 21A-21D in which a secondary cinching mechanism is provided in the form of a second flexible tensile member.

FIGS. 23A-23E illustrate respective cross sections of the heart anatomy through the CS and the use of another alternative catheter based system for serially delivering fasteners coupled with a flexible tensile member used to cinch valve tissue and correct a mitral valve insufficiency.

Figure 24A:
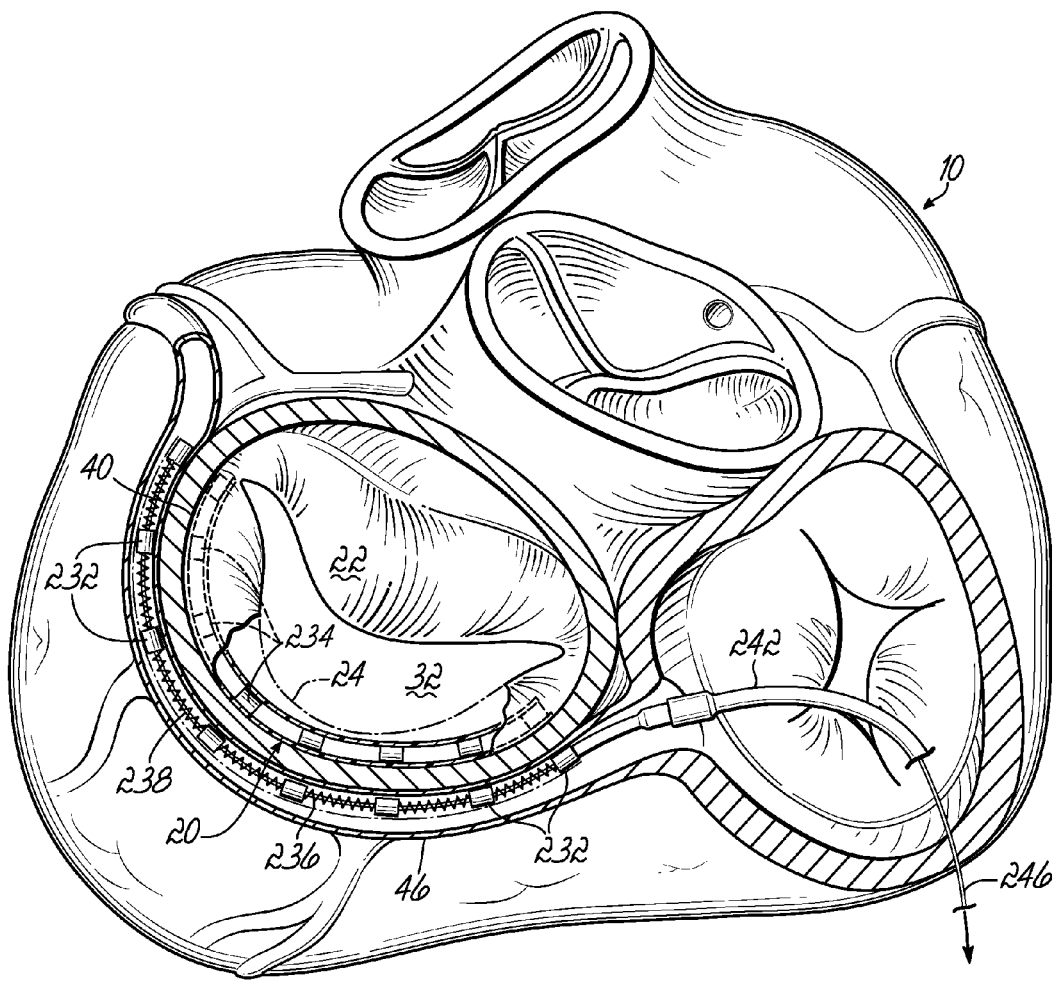
Figure 24B:
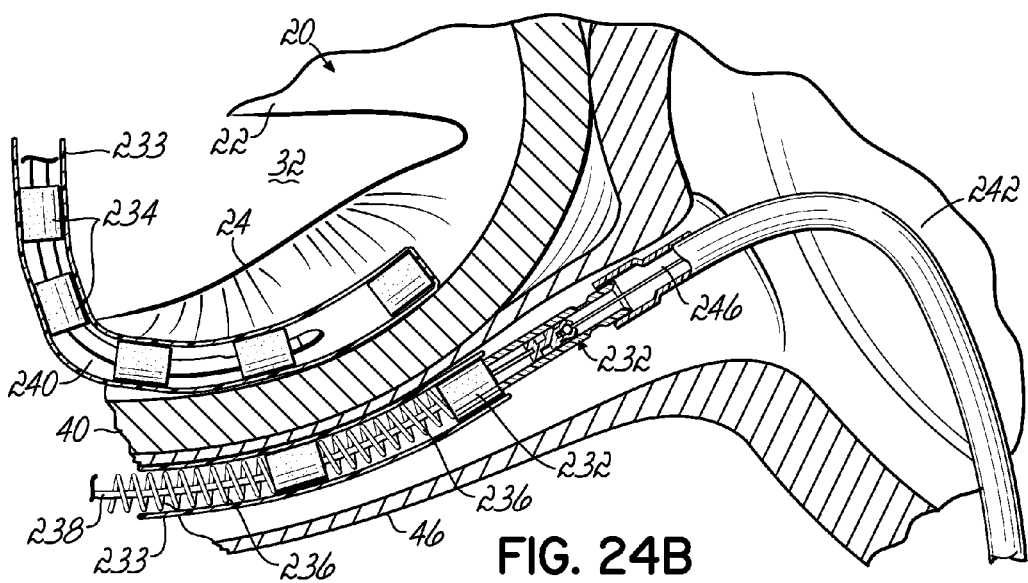
Figure 24C:
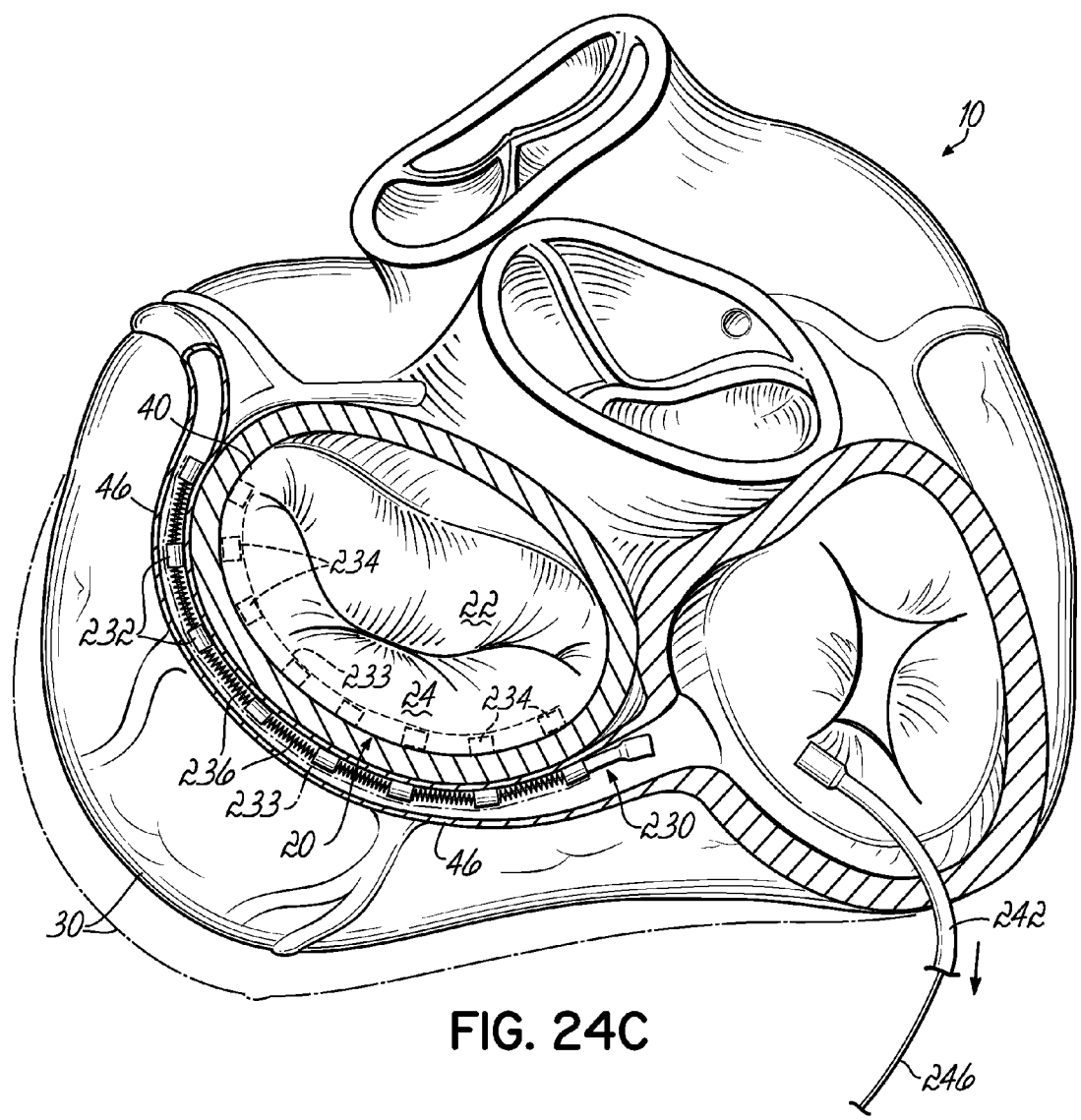

FIGS. 24A-24C are respective cross sections through the heart anatomy including the CS above the mitral valve and illustrating another alternative catheter based fastener system.

FIGS. 25A-25D illustrate an enlarged cross section of the catheter based system of FIGS. 24A-24C, and showing the cinching and locking thereof.

FIGS. 26A-26B illustrate another alternative cinching and locking system for a catheter based fastener system similar to FIGS. 25A-25D.

FIG. 26C is a cross section taken along line 26C-26C of FIG. 26A.

FIGS. 27A and 27B illustrate yet another alternative cinching and locking mechanism associated with a catheter based fastener system similar to FIGS. 26A and 26B.

Figure 28A:
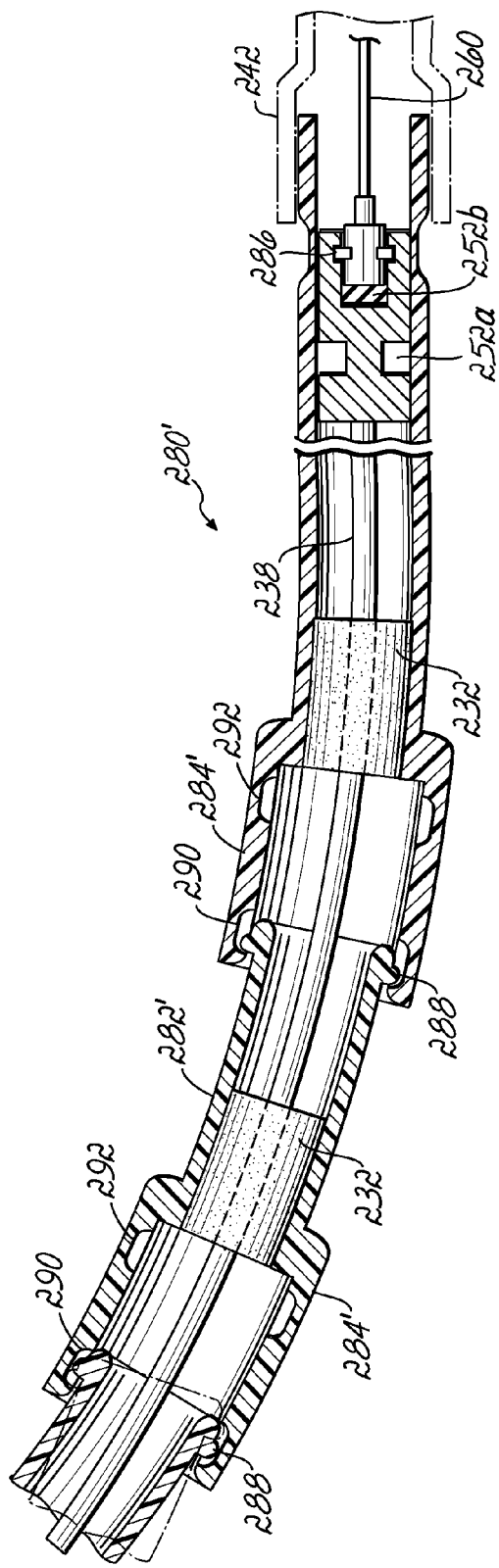
Figure 28B:
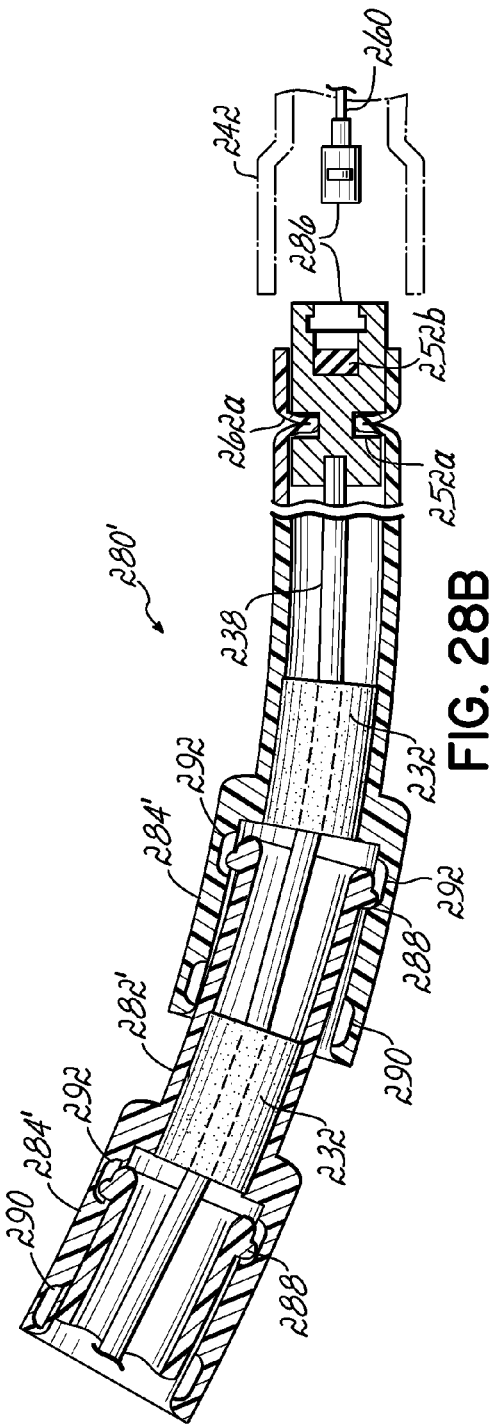

FIGS. 28A and 28B are respective cross sections similar to FIGS. 27A and 27B, but illustrating another alternative fastening system.

FIGS. 29A and 29B illustrate respective cross sections of yet another catheter based fastening system.

FIG. 30 illustrates a cross section of yet another catheter based fastener system.

FIG. 31A is a cross section taken along line 31A-31A of FIG. 30.

FIG. 31B is a cross section taken along line 31B-31B of FIG. 30.

FIGS. 32A and 32B illustrate another alternative fastening system in its nonactivated and activated states.

FIG. 32C is a cross section taken along line 32C-32C of FIG. 32A.

FIG. 33 is a cross section of another alternative fastening system.

FIGS. 33A and 33B are enlarged cross sectional views of portions of FIG. 33 respectively shown in nonactivated and activated states.

FIGS. 34A-34I are respective cross sections of the heart anatomy successively showing the use of another alternative catheter based fastening system.

Figure 35A:
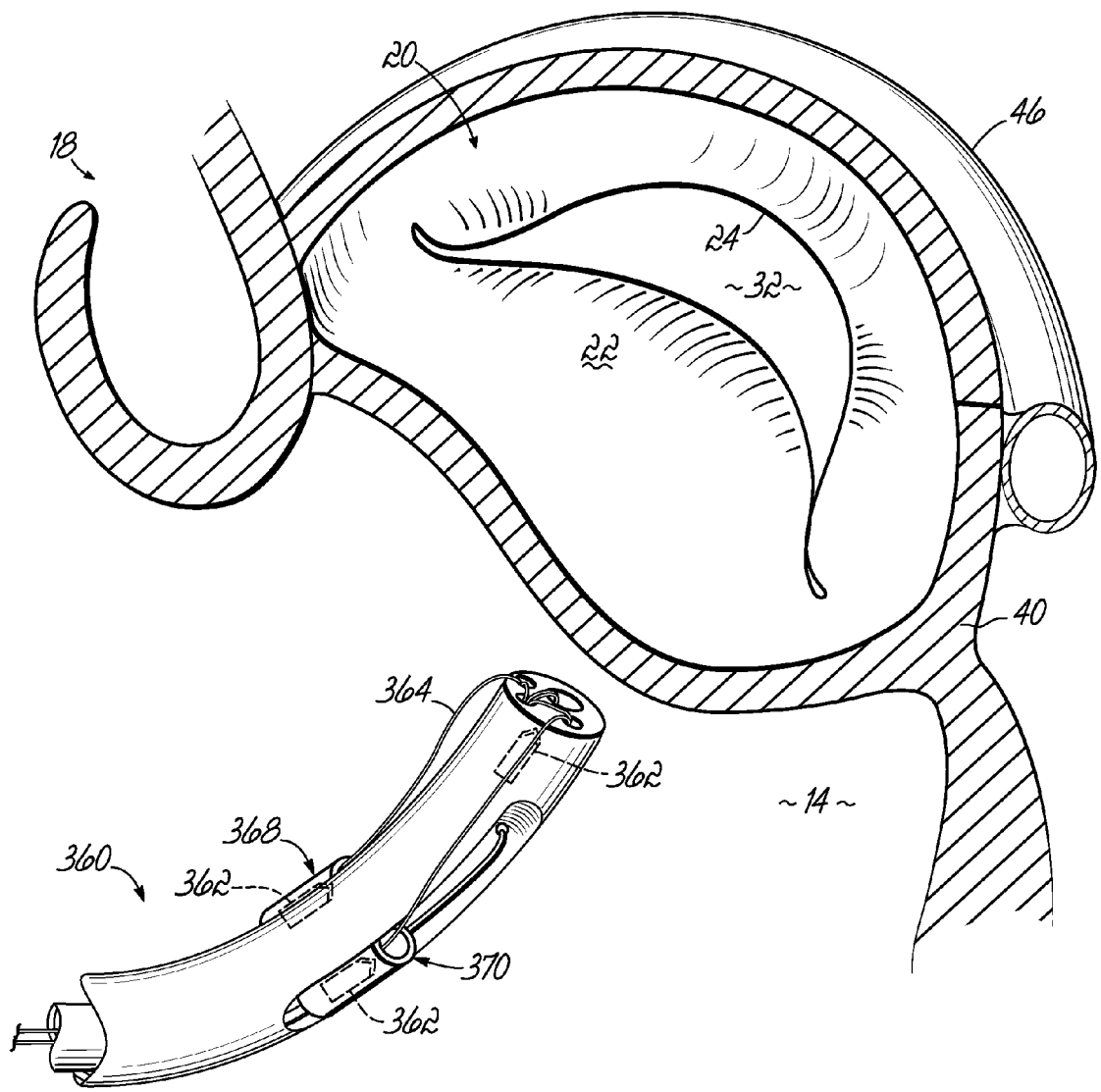

FIG. 35A is a cross section taken through the CS and illustrating a perspective view of another alternative catheter based fastener delivery device.

FIGS. 35B-35E are respective cross sections of the fastener delivery device shown in FIG. 35A and used to deliver multiple fasteners coupled to a flexible tensile member.

Figure 35B:
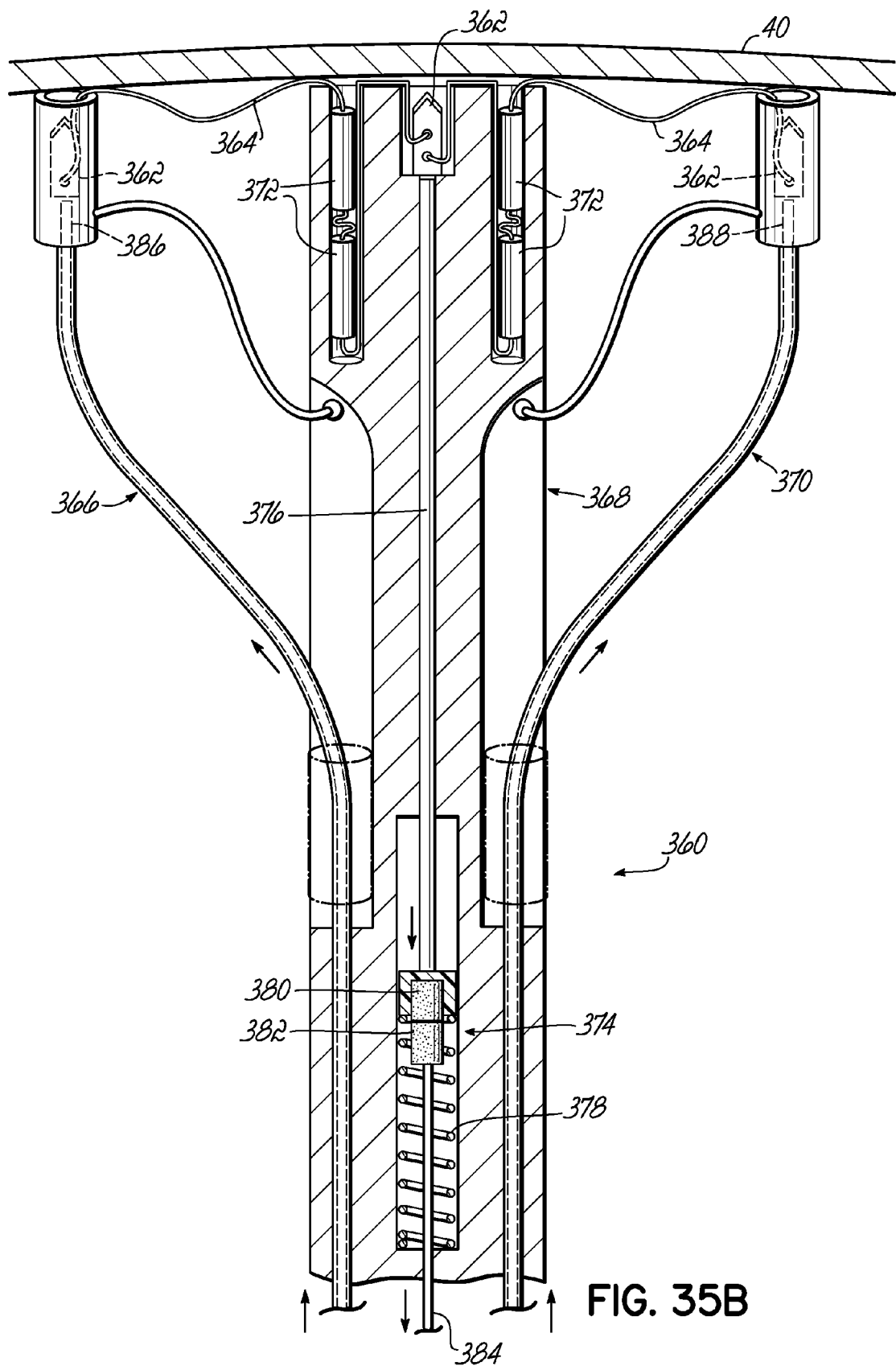
Figure 35C:
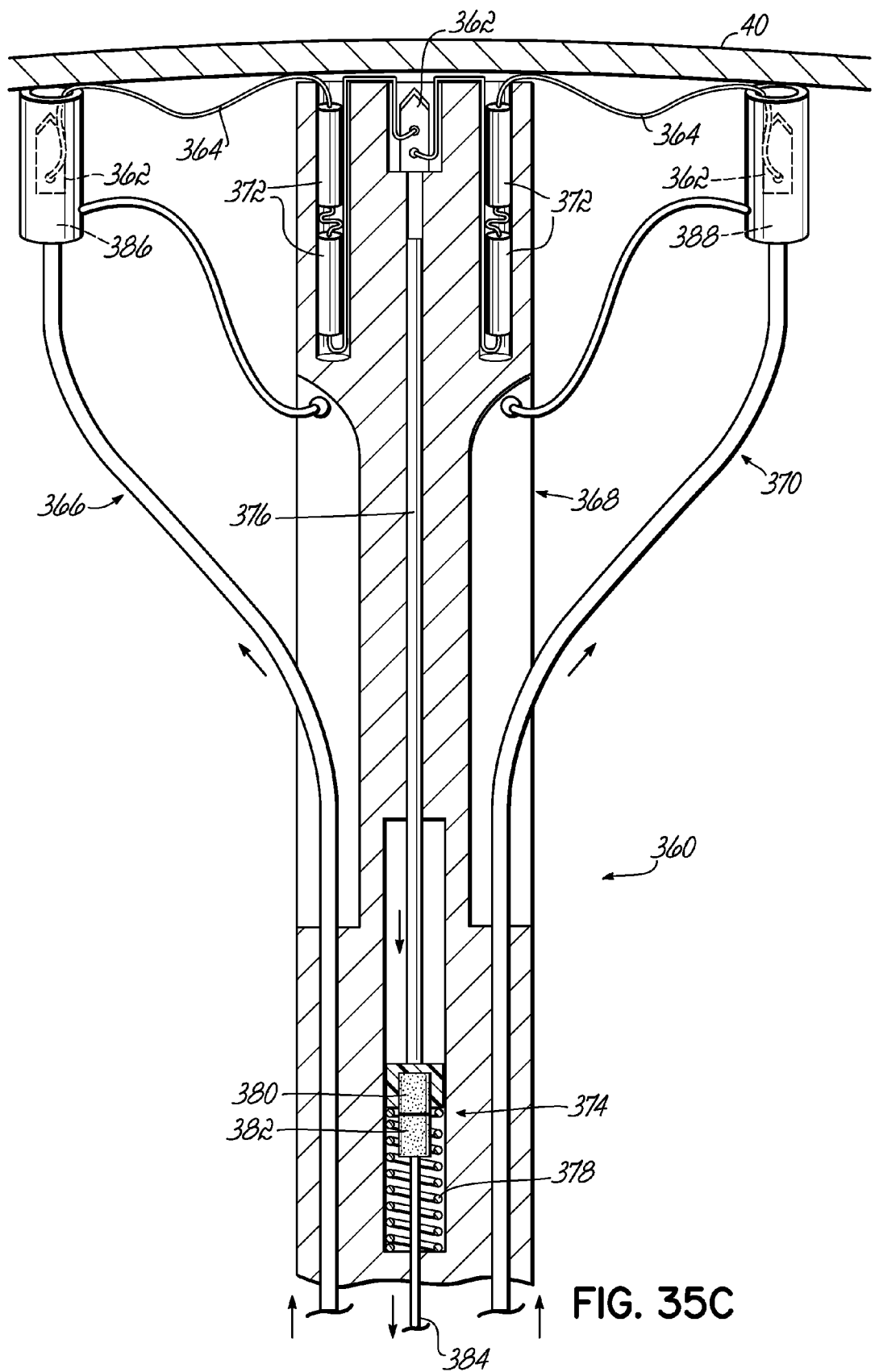
Figure 35D:
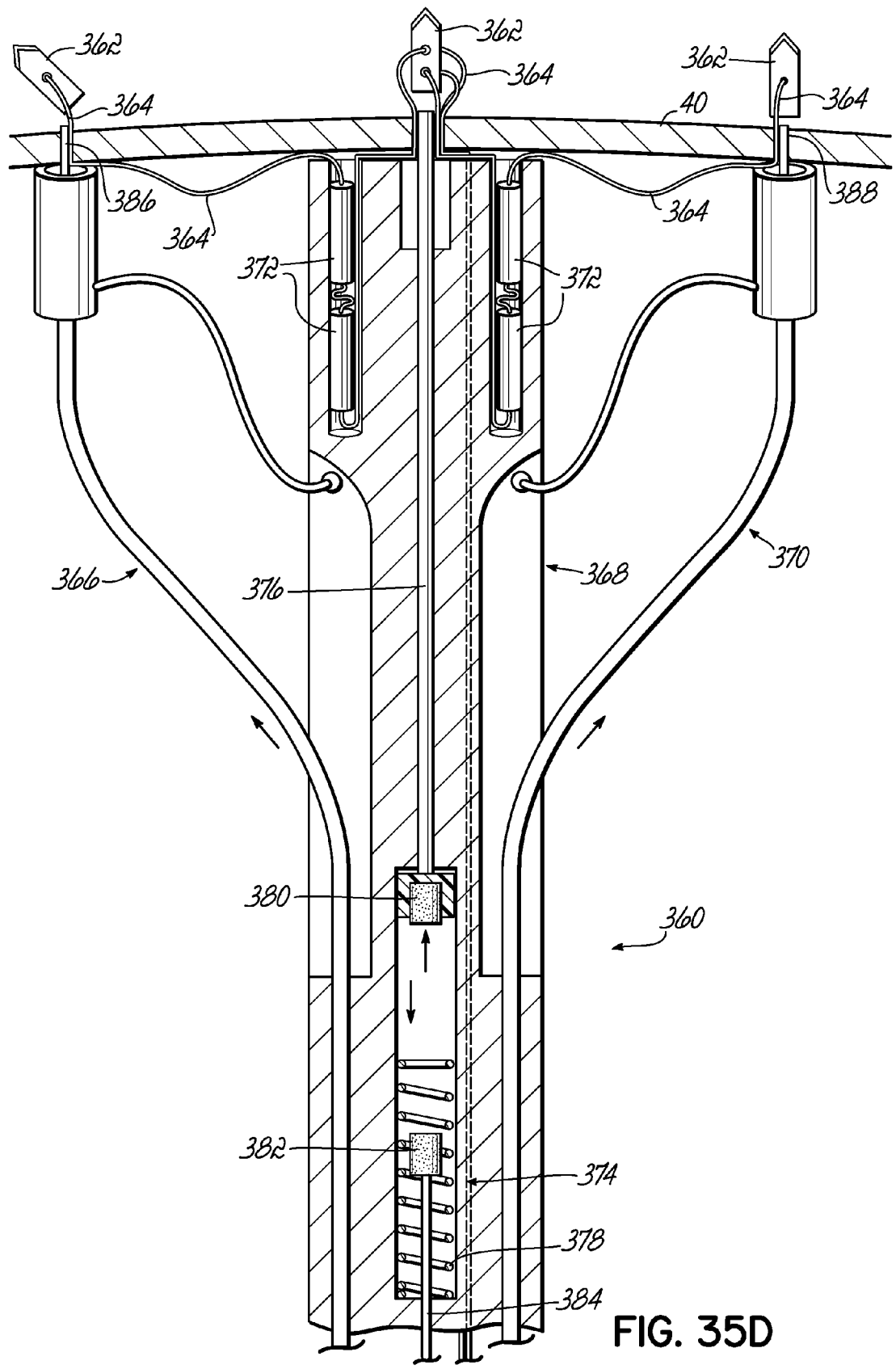
Figure 35E:
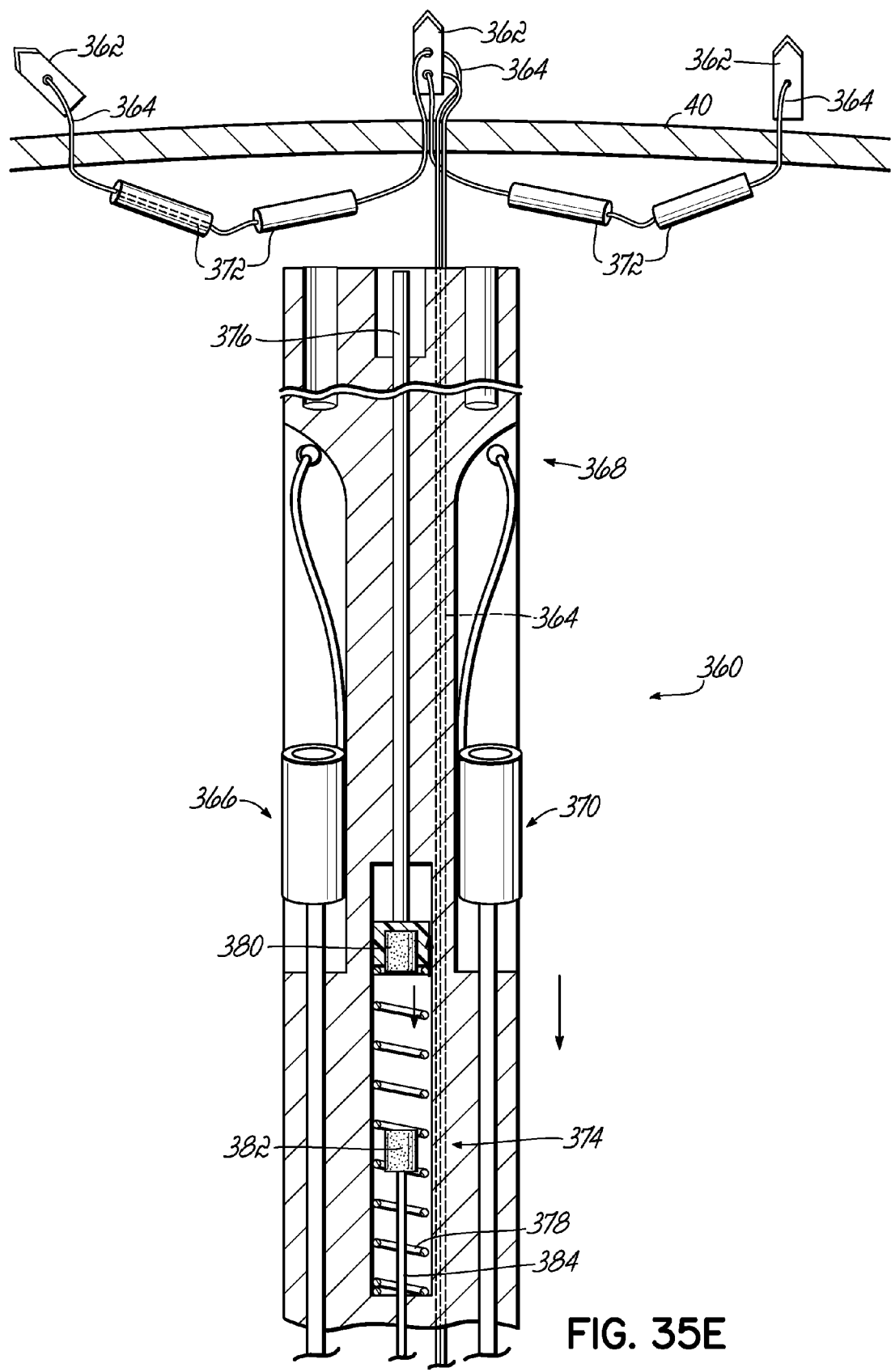
Figure 35F:
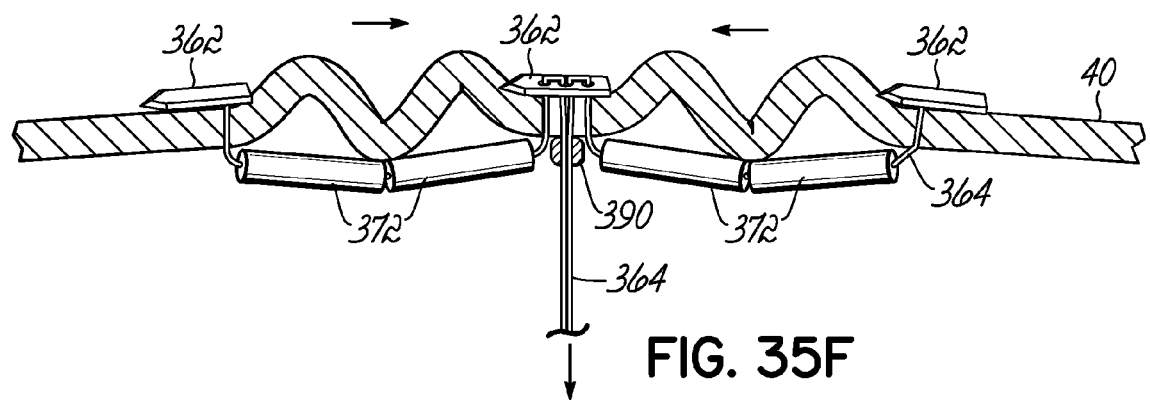

FIG. 35F is a cross sectional view of the fastening system delivered, cinched and locked to shorten the length of tissue engaged with the system.

Figure 36:
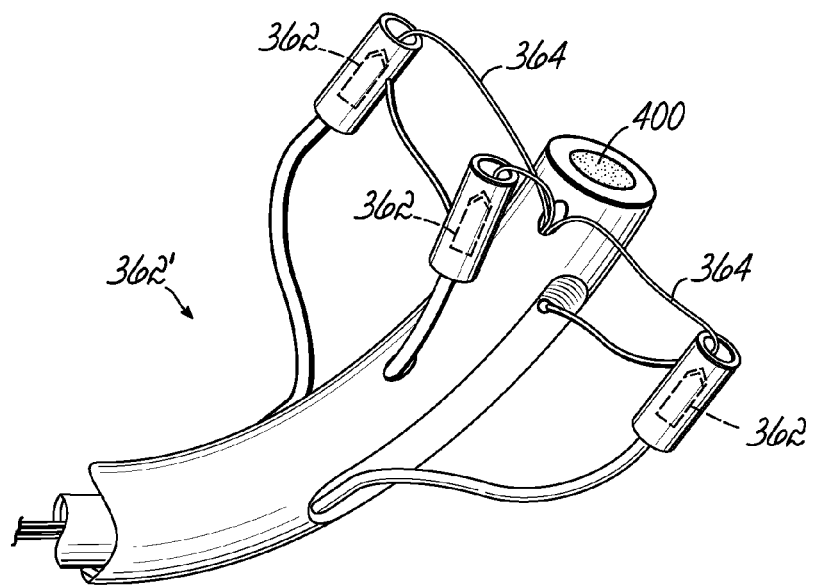

FIG. 36 is a perspective view of the distal end of another alternative catheter based fastener delivery system.

Figure 37A:
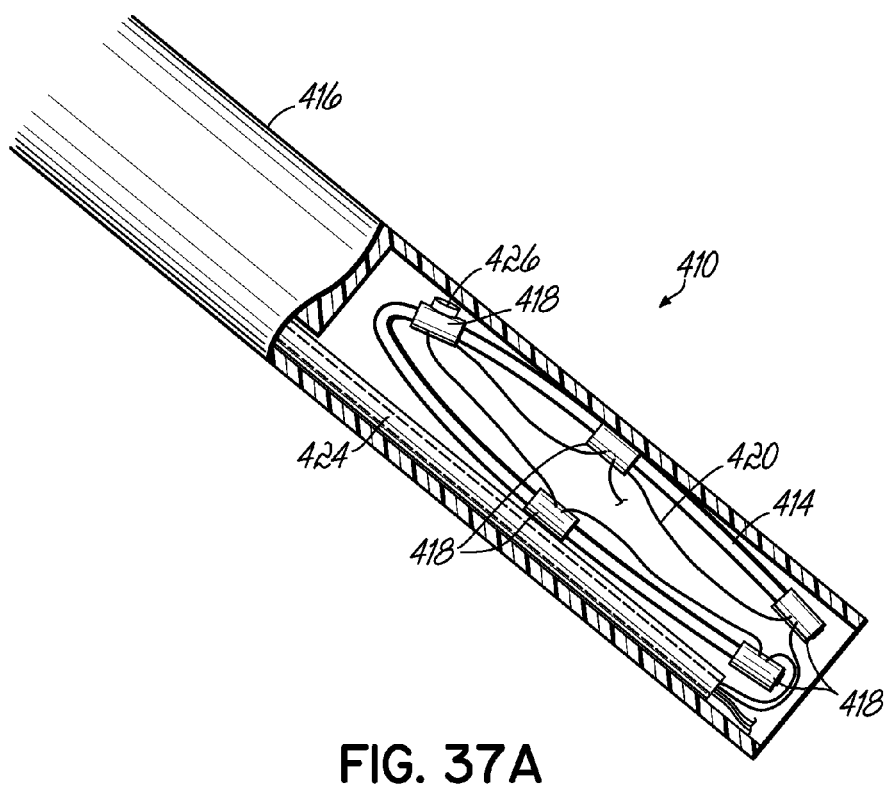

FIG. 37A is a fragmented view of the distal end of another catheter based system for delivering a fastener and valve support member of the invention.

Figure 37B:
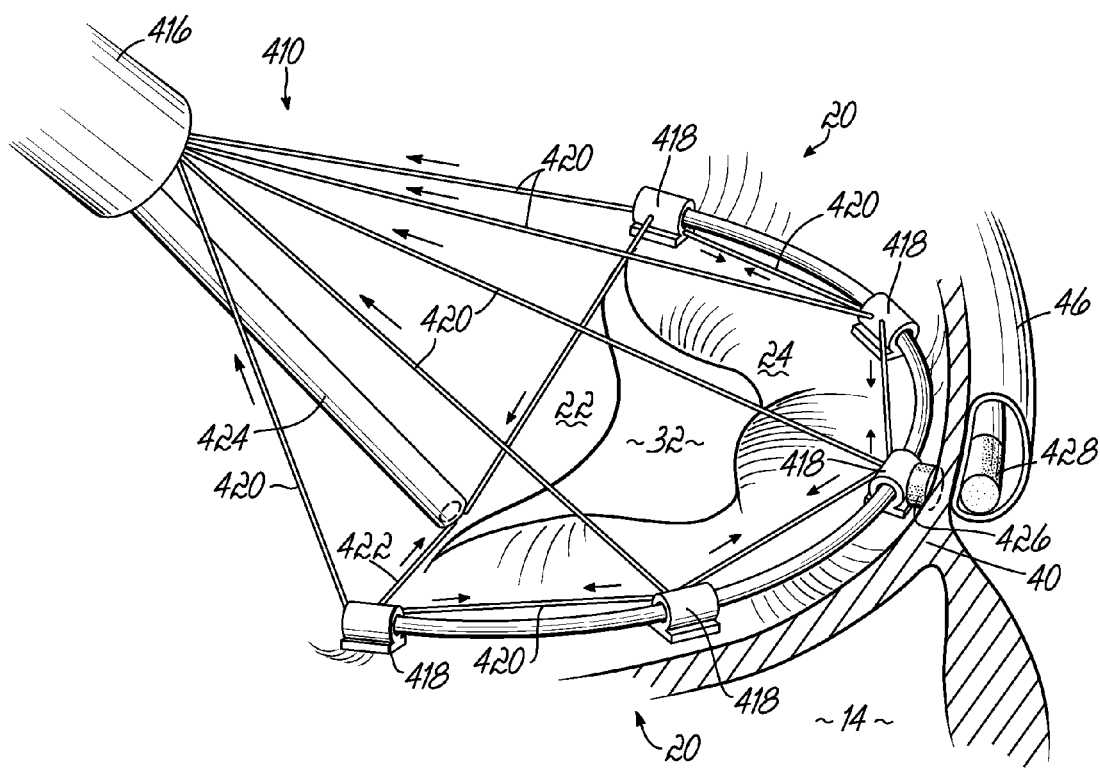
Figure 37C:
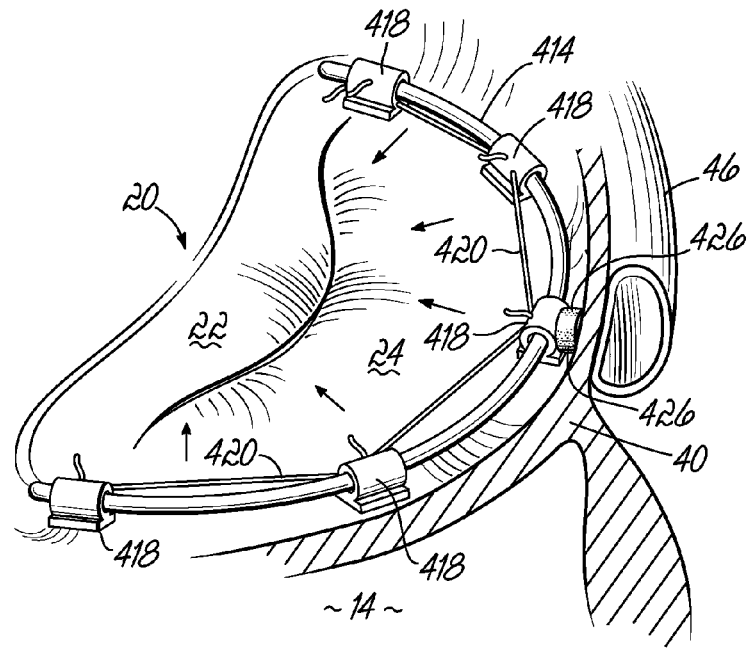

FIGS. 37B and 37C respectively illustrate the deployed valve support and fastener system on the mitral valve.

FIGS. 38A-38I respectively illustrate cross sections of the mitral valve and CS and the progression of using another catheter based fastener delivery system.

Figure 39A:
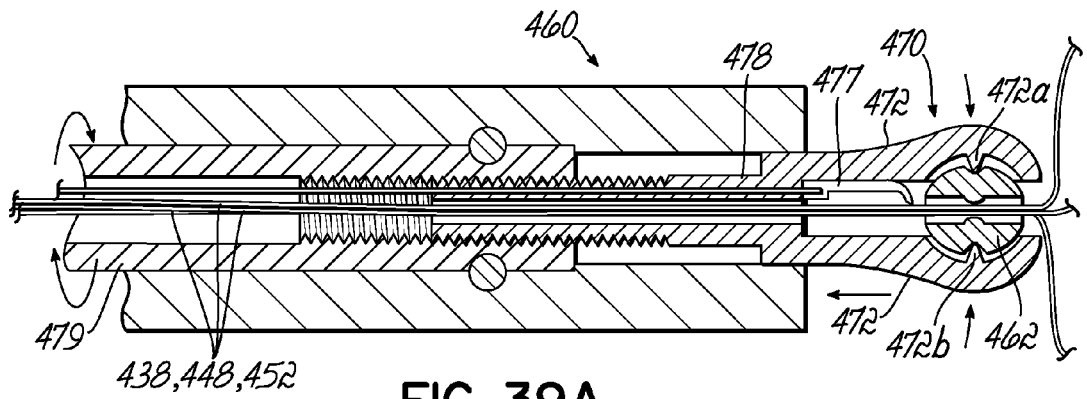
Figure 39B:
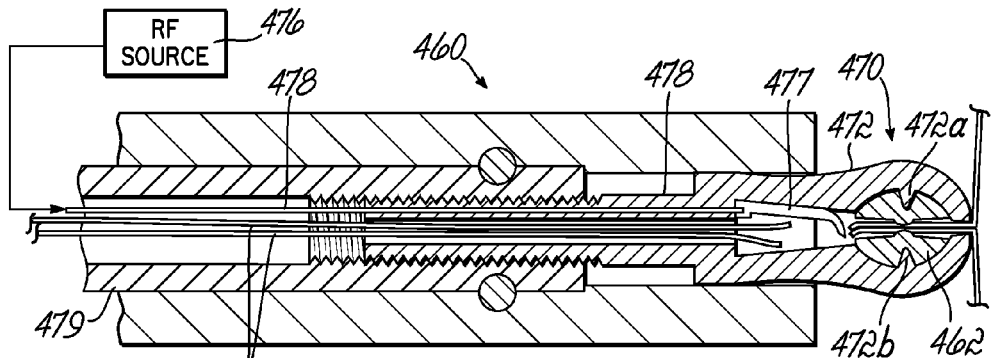
Figure 40A:
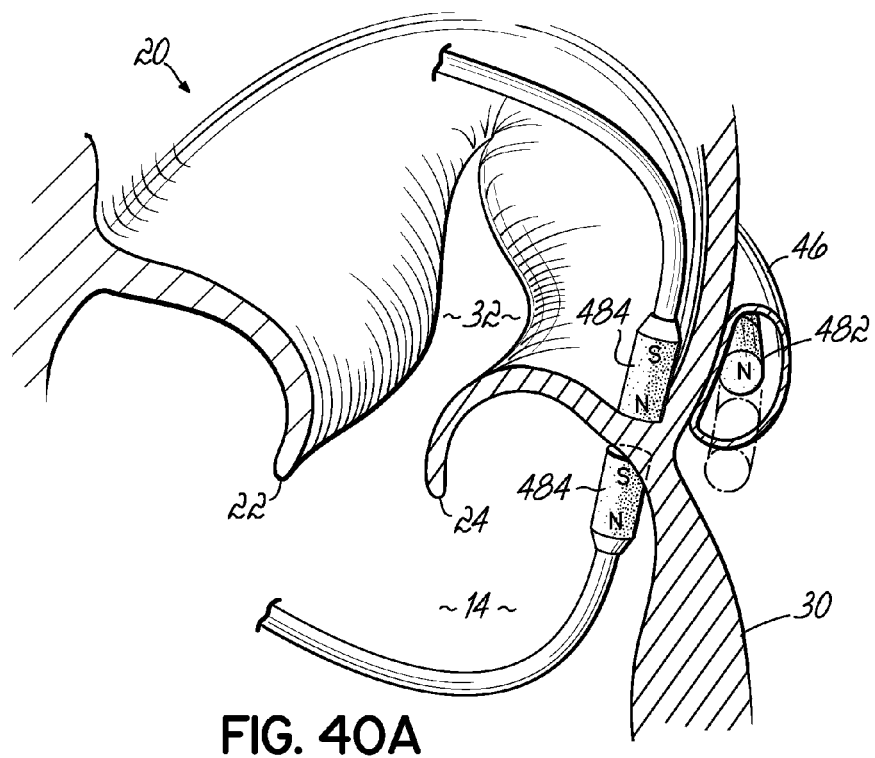
Figure 40B:
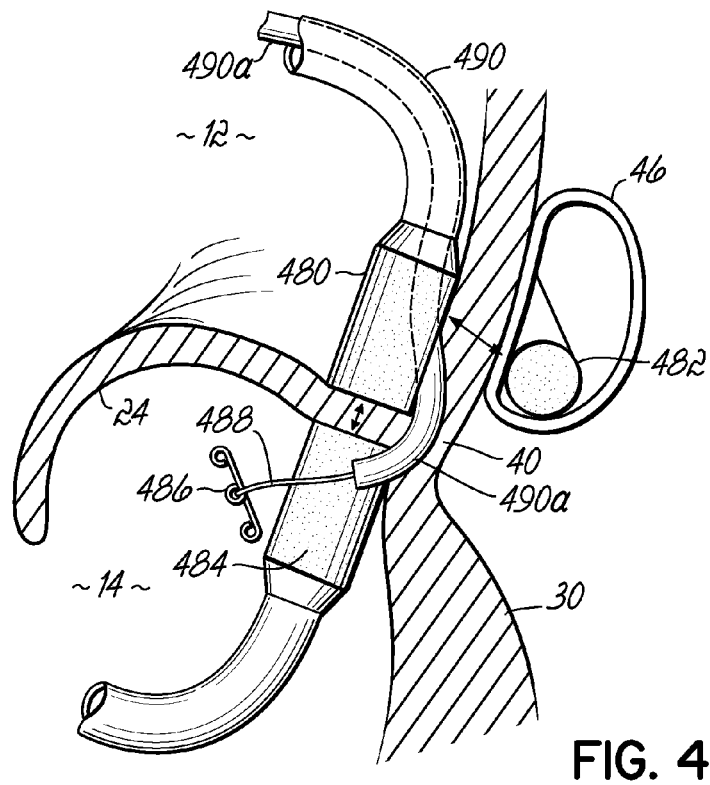
Figure 40C:
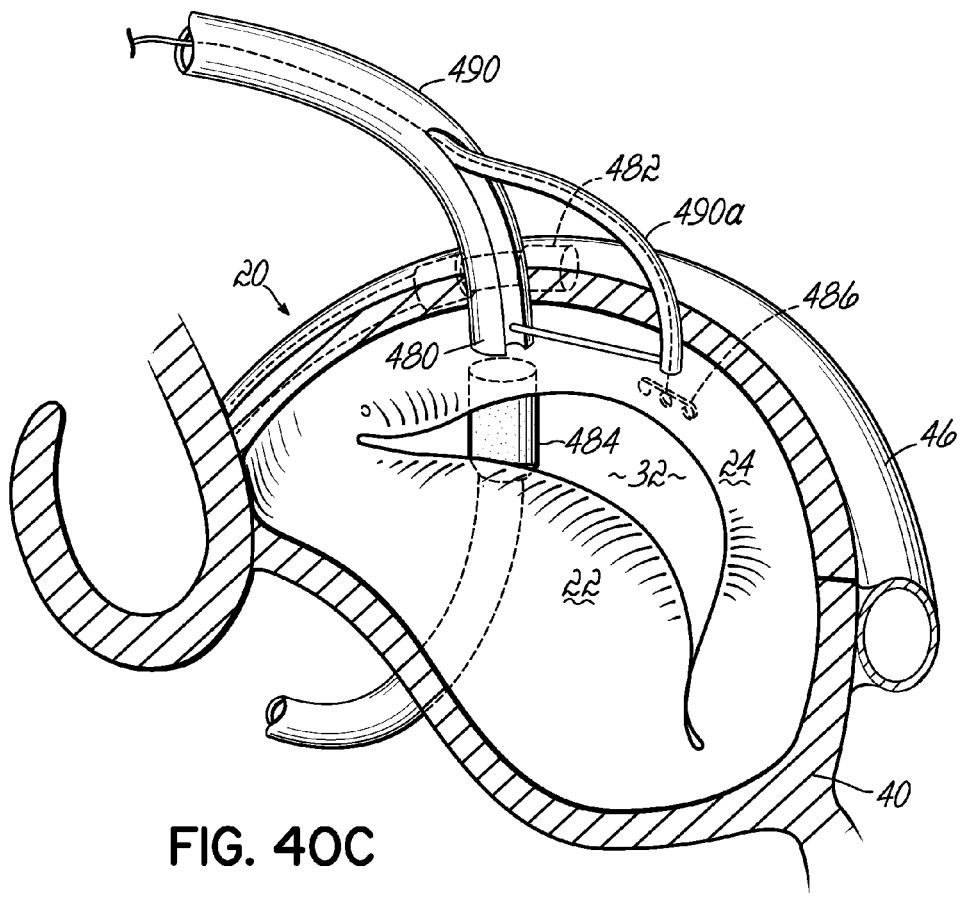
Figure 40D:
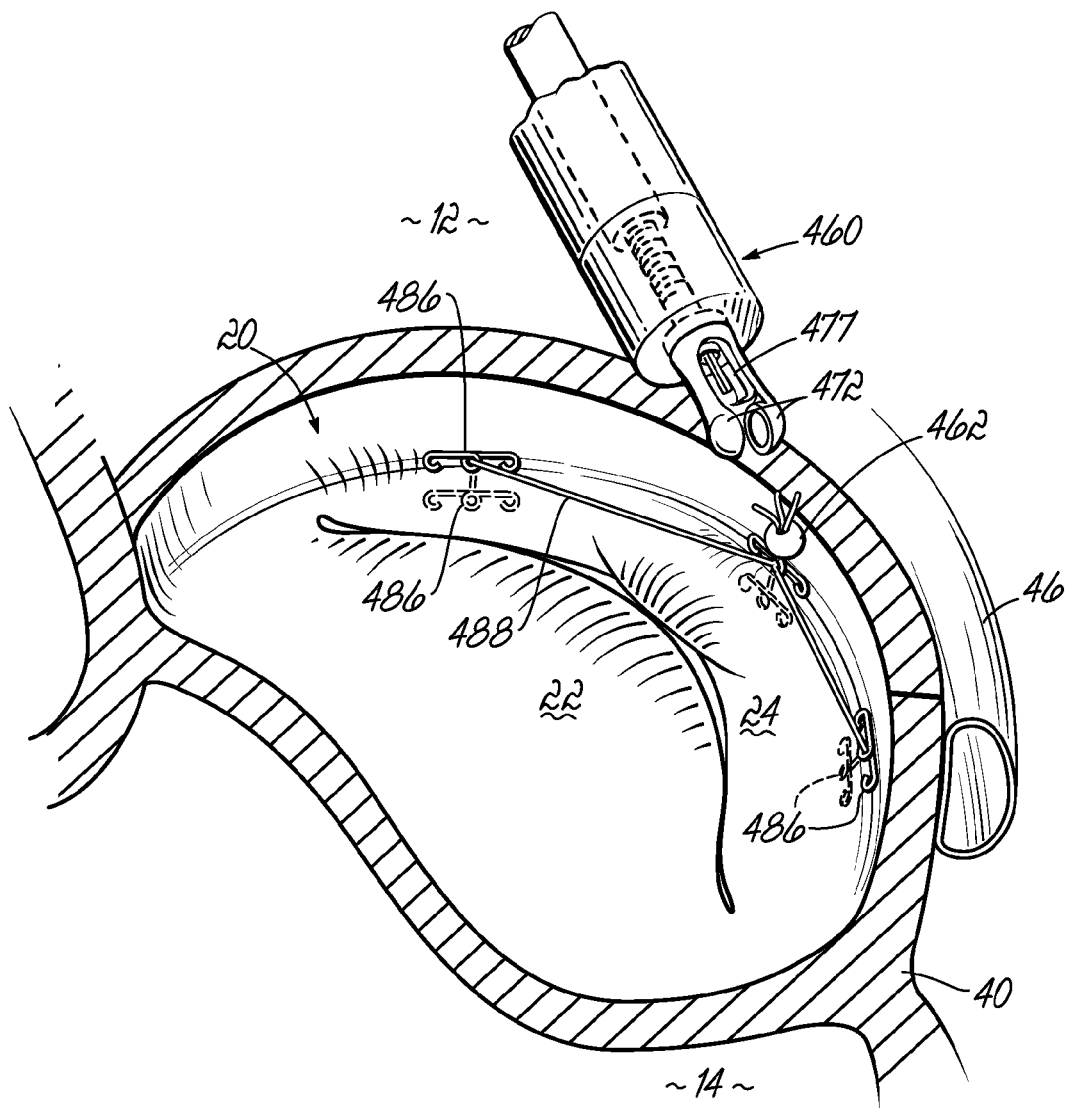

FIGS. 39A and 39B respectively illustrate cross sections of the distal end of a crimping and cutting device which may be used with various catheter based systems of this invention.

FIGS. 40A-40D respectively illustrate cross sections through the heart anatomy including the mitral valve and CS, and illustrating another alternative catheter based fastener delivery system.

Figure 41A:
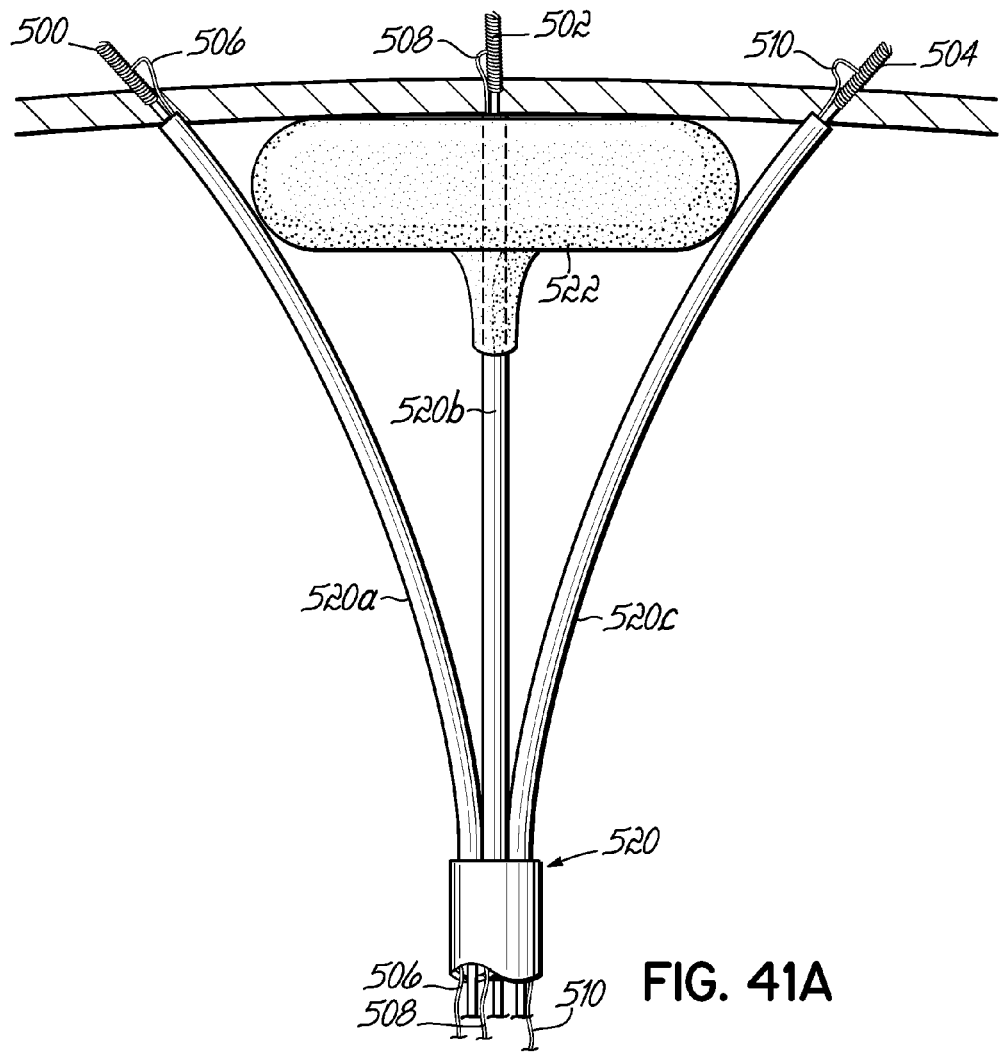
Figure 41C:
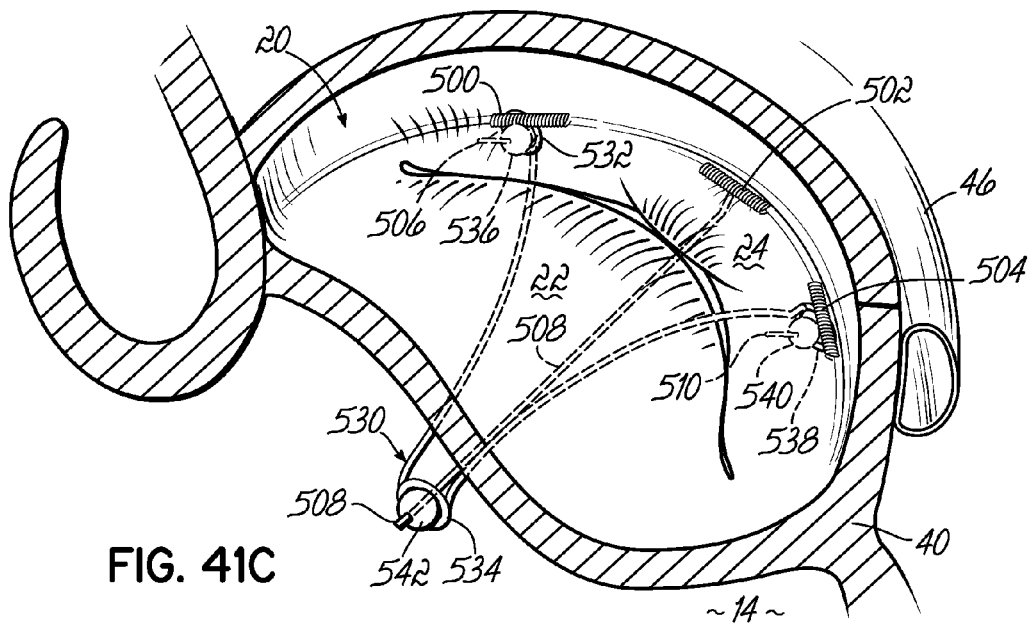
Figure 41B:
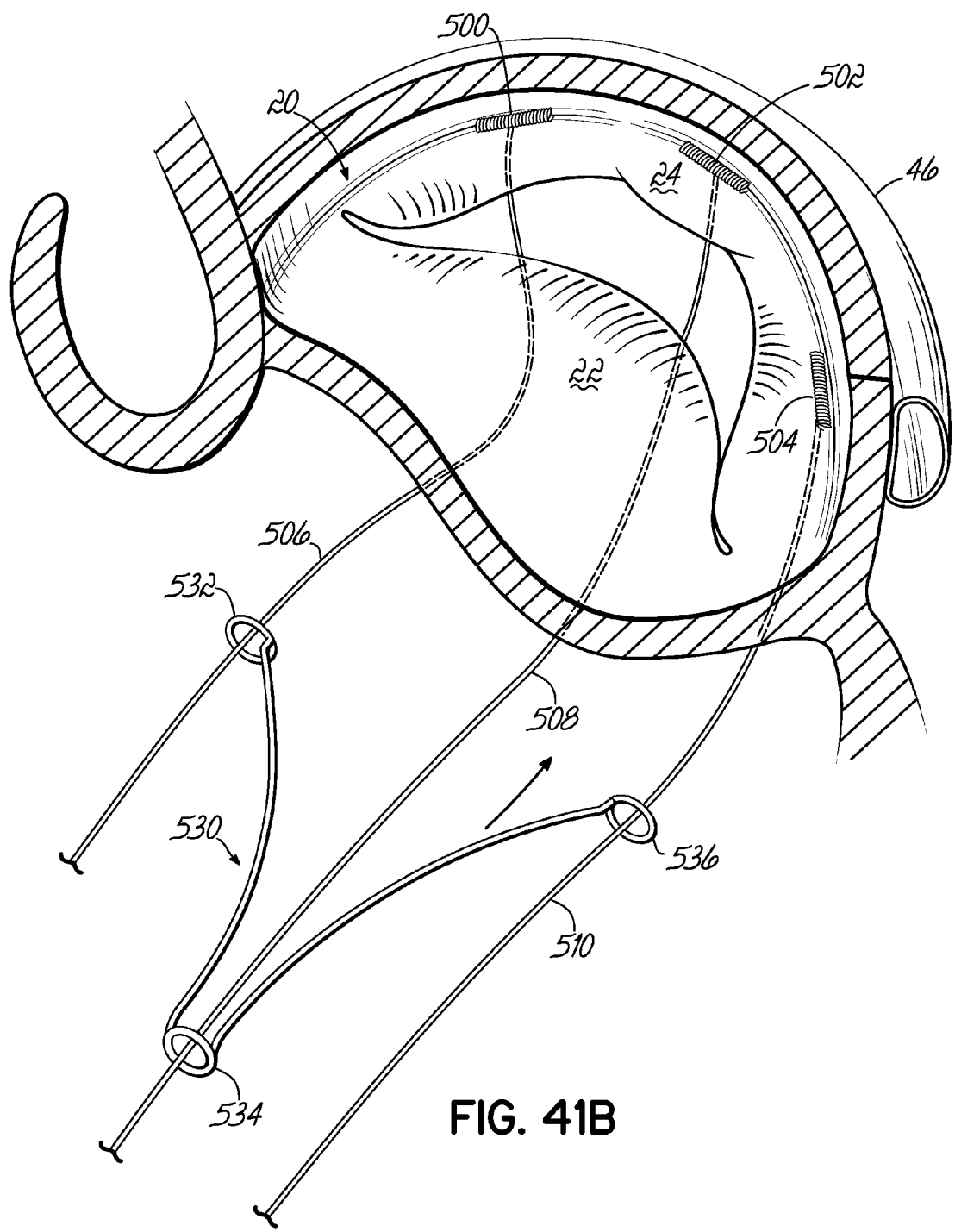

FIGS. 41A-41C illustrate another catheter based fastener delivery system.

FIG. 42A illustrates an elevational view of one exemplary fastener usable in the systems described herein.

FIG. 42B is a cross sectional view taken along line 42B-42B of FIG. 42A.

FIG. 43 is a side elevational view of another alternative fastener having a curved shape.

FIGS. 44A-44C respectively illustrate the use of another alternative fastener suitable for the systems of the present invention.

DETAILED DESCRIPTION

In this description of illustrative examples, like reference numerals refer to like element throughout the drawings. Like reference numerals with prime (') marks or double prime (") marks refer to like structure except for minor differences which will be apparent. FIGS. 1A and 1B illustrate an improved catheter delivered fastener system 50' which involves placing a permanent fastener or anchor 60 from the CS 46 through the wall of the left atrium 12 proximate annulus 40 for anchoring purposes. This improvement may be applied to the prior cinching method illustrated in Fig. I discussed above. The fastener 60 may be deployed and anchored in various manners, including those discussed further below. Because the fastener 60 extends not only through the delicate CS tissue, but also through the thicker tissue of the left atrium 12, secured anchoring takes place and, upon cinching using a flexible tensile member 54, the annulus 40 may be reduced to correct for a prolapsed valve or other mitral valve insufficiency with less risk of tearing tissue. FIGS. 2A and 2B illustrate the anatomical relationship between the CS 46 and the mitral annulus 40. In particular, the CS 46 can be noncoplanar with the mitral annulus 40, causing CS based cinching approaches to the inefficient to effectively modify the shape of the annulus 40. In many cases, the CS 46 extends above the mitral annulus 40 along the left atrial wall and, instead of pulling the annulus 40 toward the valve opening or gap 32, the left atrial wall is instead pulled inwardly as shown in FIG. 2B. This causes more of a restriction of the atrium 12 above the valve 20, rather than a reduction of the annulus 40 itself and, therefore, prevents a complete correction of the valve insufficiency in this case. In an approach which is similar to the approach shown in FIGS. 1A and 1B, but having additional benefits, a fastener or anchor 62 extends from the CS 46 into the left ventricle side of the annulus 40. This plicates the tissue between the CS 46 and the left ventricle 14 thereby bringing the CS 46 closer to and/or more in line with the annulus 40. Once this plication has taken place as shown in FIG. 2C, a CS cinching device can more efficiently and effectively reduce the mitral annulus 40. That is, when cinched toward the valve opening or gap 32, the cinching device, which is more in line with the valve annulus 40, can better pull the posterior leaflet 24 toward the anterior leaflet 22 thereby closing the gap 32 between the leaflets.

Figure 3A:
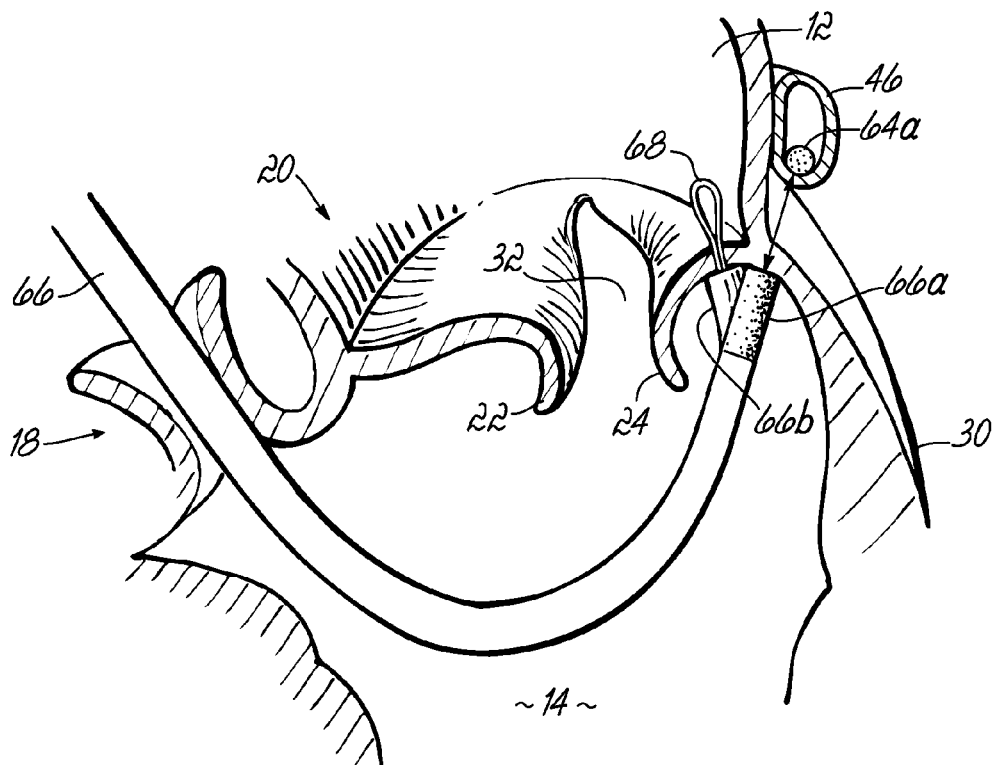
Figure 3B:
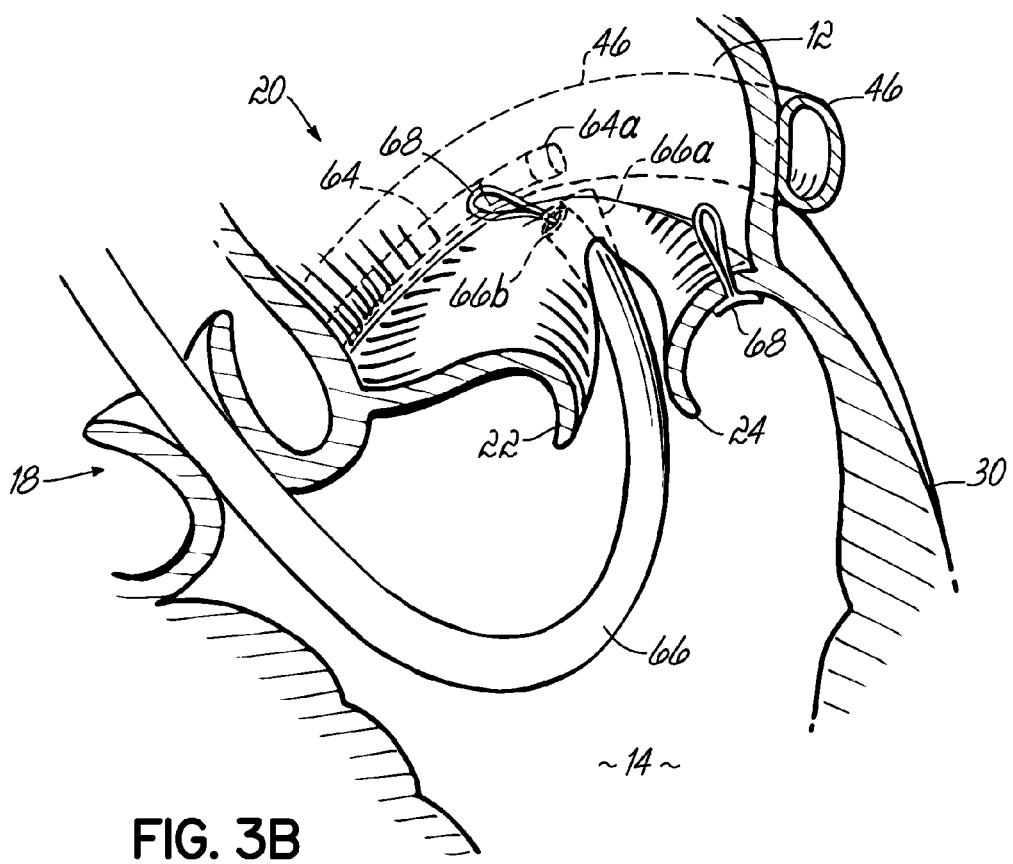
Figure 3C:
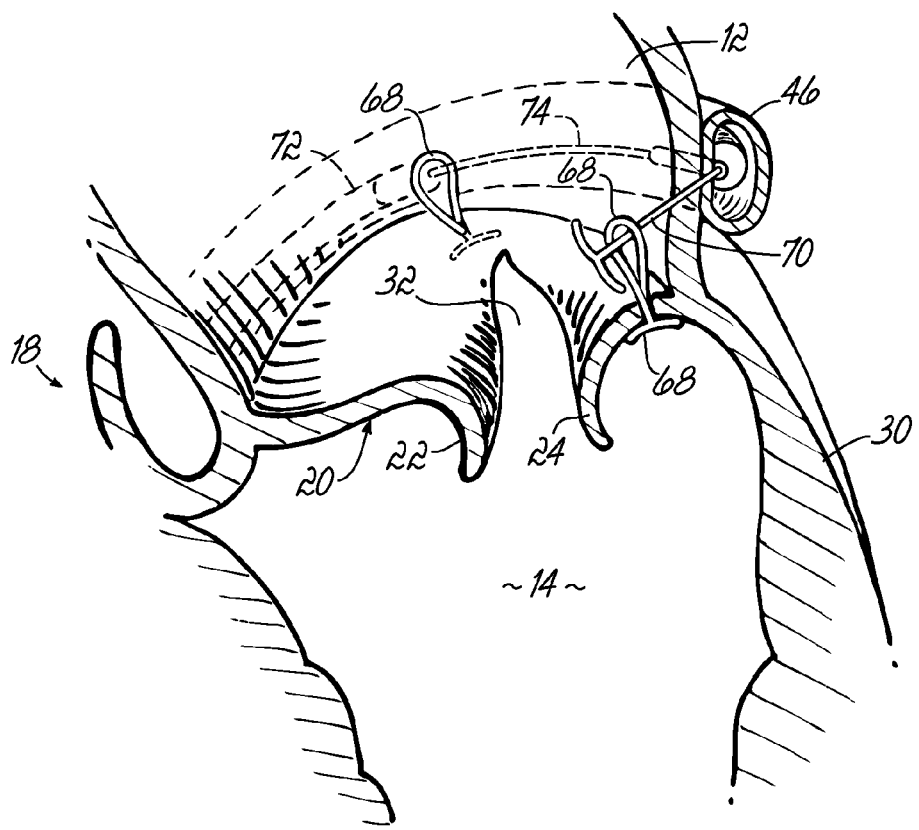
Figure 3D:
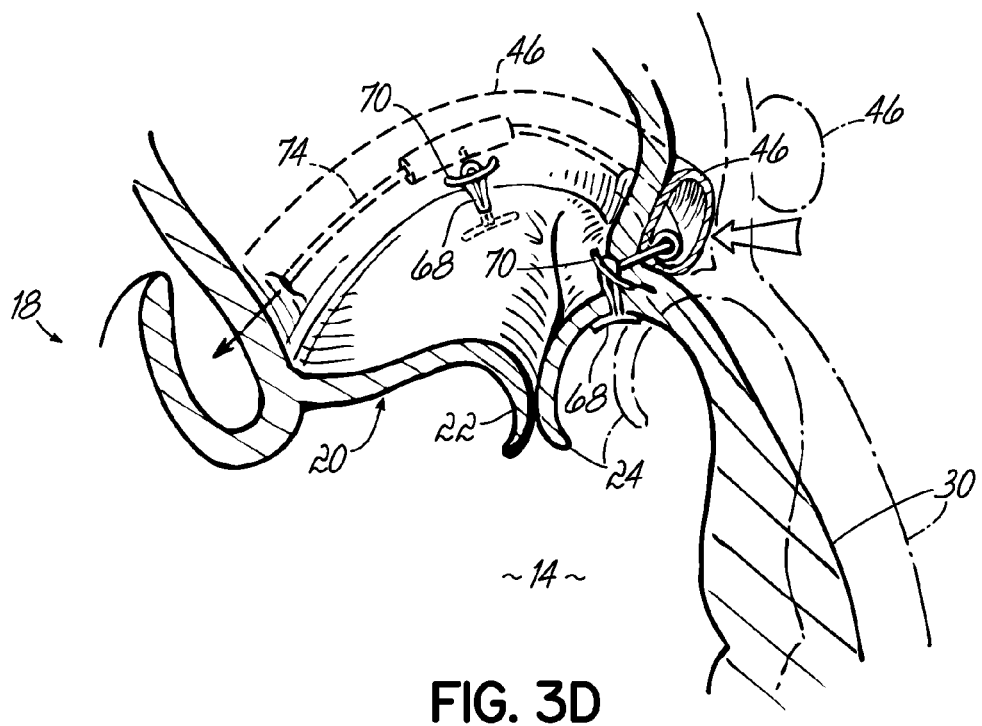

As shown in FIGS. 3, 3A and 3B, a pair of magnetically attractive catheters 64, 66 can be used in concert with each other using the CS 46 as an approximate guide to locate and position the tip of another catheter or catheter portion at the mitral annulus 40. More specifically, as one example, one catheter 66 includes both a magnetic guiding portion 66a and an anchor delivery portion 66b positioned in a predetermined manner, such as at a predetermined acute angle relative to the magnetic portion 66a. Another catheter 64 is placed in the CS 46 and includes a magnetic guiding portion 64a. The two magnetic guiding portions 64a, 66a magnetically couple with one another to lock up the position of the anchor delivery catheter portion 66b at a predetermined angle which will properly deliver a fastener or anchor 68 into a desired portion of the tissue. As shown in FIG. 3A, the magnetically locked catheters 64, 66 can deliver a first loop type anchor or fastener 68 through the valve annulus 40 on a skewed or otherwise known trajectory from the axis of magnetic attraction, such that the loop type anchor or fastener 68 is accurately placed, for example, through the annulus 40 from the left ventricle side to the left atrium side of the mitral valve 20. As shown in FIG. 3B, the CS catheter 64 can be translated to a different position within the CS 46 causing the magnetic tip 66a of the left ventricle catheter 66 to follow along the annulus 40 where subsequent loop type anchors or fasteners 68 may be placed in a similar fashion to the first applied anchor or fastener 68. FIG. 3C illustrates that a loop type fastener or anchor 68 may capture a T-bar type anchor or fastener 70 passing from the CS 46 through the left atrial wall using a catheter delivery system 72 guided within the CS 46. In this embodiment, fasteners 68 are therefore placed from the left ventricle 14 into the left atrium 12, and additional connecting fasteners 70 are placed from the CS 46 into the left atrium 12 for engagement with the other fasteners 68. As shown in FIG. 3D, multiple loop and T-bar anchors or fasteners 68, 70 may be cinched together with a flexible tensile member 74 similar to a drawstring-type configuration, resulting in alignment of the CS 46 and the annulus 40 into a more coplanar relationship at several locations. The cinching or drawstring action therefore closes the gap 32 between the posterior leaflet 24 and the anterior leaflet 22 in a more even and effective manner.

FIG. 4 illustrates magnetically attractive catheter portions 64a, 66a respectively in the CS 46 and under the mitral annulus 40 used to deliver a series of anchors or fasteners 76 with a T-bar shape from the left ventricle side of the mitral valve 20 to the left atrium side of the mitral valve 20. As also shown in FIG. 4, the T-bar shaped anchor fasteners 76 are delivered in a daisy chained fashion from catheter portion 66b such that a second catheter 78 may be used to cinch a drawstring or flexible tensile member 80 to shorten or reduce the valve annulus 40. As shown in FIG. 5, the anchors or fasteners 76 may be cinched together using the drawstring or flexible tensile member 80 within catheter 78 to pull the posterior leaflet 24 toward the anterior leaflet 22. The flexible tensile member 80 is then locked in place or otherwise secured to retain the fasteners 76 in their new positions, such as in one of the manners described below.

FIGS. 6A-6F respectively illustrate catheters 82, 84 being placed into the heart 10 through the aortic valve into the left ventricle 14 and through the CS 46 generally adjacent the valve annulus 40. This top view of the heart 10 shows how a first T-bar type anchor or fastener 86 having a tail, forming a flexible tensile member 88, is loaded into the CS catheter 84 at the proximal end 84a so that it may be pushed down to the distal tip 84b to be in position for delivery. The position of the left ventrical catheter 82 with a magnetic tip 82a is also shown generally opposite to the distal tip 84b of the CS catheter 84. As shown in FIG. 6B, a second anchor or fastener 90 is delivered in a daisy chain fashion by running an eyelet 90a on the second anchor 90 over the tail or flexible tensile member 88 associated with the first anchor 86. FIG. 6C illustrates the second anchor 90 of the daisy chain delivered through the valve annulus 40 at a spaced apart location from the first anchor 86. FIG. 6D illustrates a third anchor 92 at the annulus 40 similarly delivered along flexible tensile member 88 using an eyelet portion 92a. Anchor 92 is threaded through the CS catheter 84 and driven through the tissue generally at the valve annulus 40. In the case of this type of anchor, respective transverse bar portions 86b, 90b, 92b of the anchors or fasteners extend into the left ventricle 14. FIG. 6E illustrates a locking member 94, including a crimp 96 delivered over the daisy chain tail or flexible tensile member 88 within the proximal CS 46. Locking member 94 is shaped or otherwise configured to hold its position within the CS 46. FIG. 6E-1 illustrates the crimp 96 before crimping onto the flexible tensile member or tail 88. As shown in FIGS. 6F and 6F-1 a catheter device 98, which may be deployed through a suitable delivery catheter (not shown) may be used to pull the flexible tensile member 88 thereby cinching the assembly and pulling the posterior leaflet 24 toward to the anterior leaflet 22. Once this cinching is accomplished, the crimp is crimped against the flexible tensile member 88 adjacent to the lock member 94 to keep the assembly at the desired position.

FIG. 7A illustrates how magnetically attractive portions 82a, 84b of the LV and CS catheters 82, 84 should be strongly attracted when the gap distance ($d_1$) is relatively short. If this gap distance $d_1$ is not relatively short, then other methods of increasing the lock up force may be necessary as further described herein below.

Figure 7G:
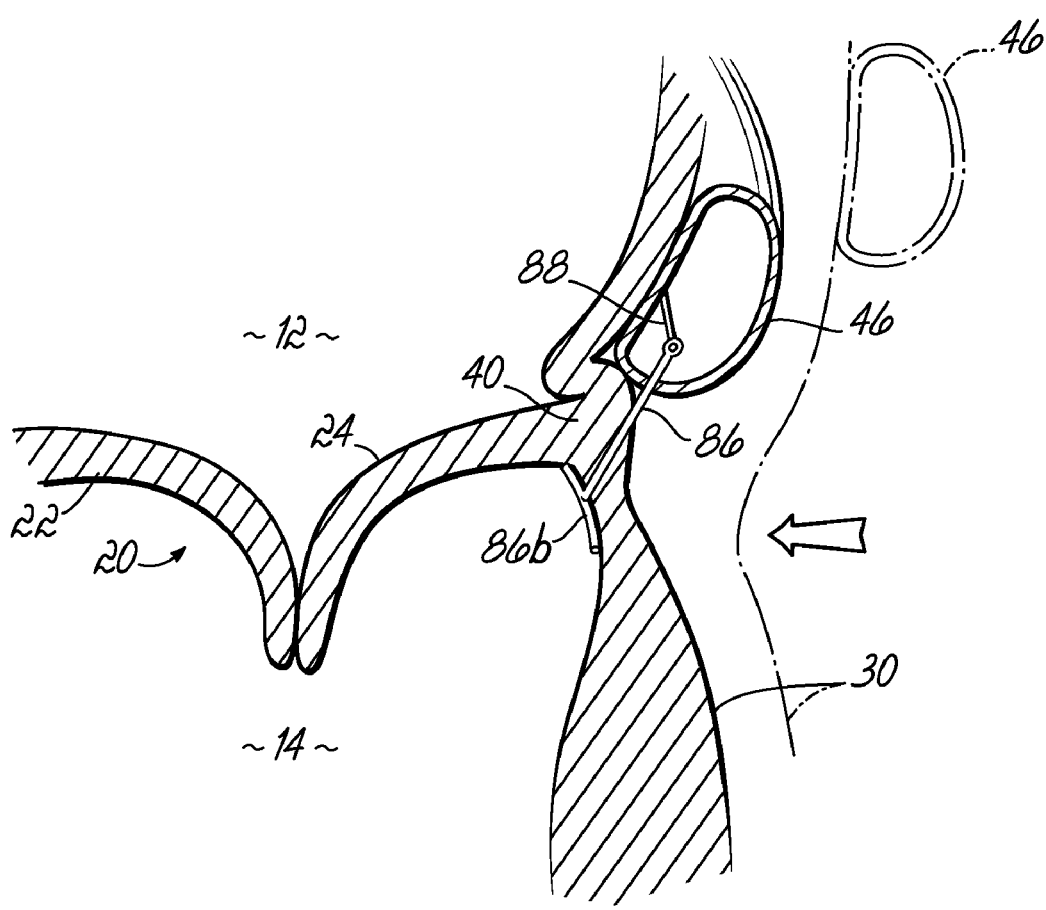

FIGS. 7B and 7C illustrate how a T-bar type anchor or fastener 86 would be pushed from an opening 84c in the CS catheter through the tissue from the CS 46 into the left ventricle 14 until it is fully deployed across the tissue. FIG. 7D illustrates a larger gap $d_2$, through which two magnetic portions 82a, 84b of the respective LV and CS catheters may magnetically couple, depending on the magnetic attractive forces developed. In FIGS. 7E and 7F, the magnetic catheter in the LV 14 has not been illustrated (only for purposes of clarity), such that the delivery of a T-bar type fastener or anchor 86 may be shown in its fully deployed state across the tissue. As shown in FIG. 7F, the T-bar portion or transverse portion 86b of the fastener 86 self-rotates in order to fit snugly along the annulus 40 under the posterior leaflet 24. In FIG. 7G, the relative position of the CS 46 to the annulus 40 is improved after cinching of the anchor 86 plicates the tissue between the annulus 40 and the CS 46 as previously described.

FIGS. 8A-8C illustrate that multiple magnets 102a, 102b may be used in the CS, such as on a CS catheter 102, to attract an opposite magnet pole at the tip 100a of the LV catheter 100. This allows the LV catheter 100 to be steered in three axes to deliver a fastener through a second catheter portion 100b into the annulus 40. It will be appreciated that multiple magnets may also or alternatively be used in the LV 14 and/or in the LA for steering purposes and/or additional magnetic force. FIG. 8C illustrates in detail how a pair of magnets 102a, 102b in the CS 46 mounted such that like poles are facing each other results in a 360° magnetic field which attracts the opposite pole of a magnetic catheter tip 100a within the LV 14. This can eliminate the need to rotationally orient the CS catheter 102 so that its pole is facing an opposite pole in the LV 14.

FIG. 9 illustrates the use of electromagnets 104 in a CS catheter 106 which may be used in conjunction with or as replacements for permanent magnets as described in the above embodiments. It will also be appreciated that one element which generates magnetic forces may be used in conjunction with another element which is magnetically attracted to the magnetic force generating element, but not necessarily a magnetic force generating element itself. For example, an electromagnet or permanent magnet may be positioned on one side of the tissue to be anchored, and another element formed from ferrous metal may be positioned on the opposite side of the tissue for magnetic coupling purposes while a fastener or anchor is driven into the tissue.

FIG. 10 illustrates a CS catheter 108 configured with multiple opposite pole magnetic pairs 110, 112 along its length and a steerable LV catheter that may be directed to each discrete pair of magnets 110, 112 to delivery anchors or fasteners (not shown), such as in one of the manners previously described.

Now referring to FIGS. 11A, 11A-1, 11B and 11B-1, a CS catheter 116 may be configured with multiple discrete magnets 118 along its length, wherein the poles of the magnets 118 are arranged such that they are magnetically attracted to each other, yet kept apart by a restraining force, such as pressurized air directed to a bladder-like structure 120 between the magnets 118. In this case, the magnets 118 are being used as fasteners to fasten or trap tissue therebetween. A similar catheter 122 delivers magnets 124 on an opposite side of the tissue, such as within the LV 14. When the restraining force is removed, such as by reducing the air pressure as shown in FIGS. 11B and 11B-1, the magnets 118 are attracted to each other and thereby modify the valve annulus 40 such that the posterior leaflet 24 is pulled toward the anterior leaflet 22. As shown best in FIGS. 11B and 11C, each strip of magnets 118, 124 has opposing poles along its length and thereby plicates the tissue by removing a restraining force between the magnets 118 in the CS 46, thereby allowing the attracted magnets 118 to move toward each other and plicate the annulus tissue therebetween. The magnets 124 in the LV catheter 122 may be configured in the same manner as magnets 118.

FIGS. 12A and 12B illustrate respective strips of magnets 118, 124, as described in connection with FIGS. 11A-11C in the CS 46 and the LA 12 instead of the LV 14. The two strips of respective magnets 118, 124 align with each other such that the magnets 118, 124 are anchored to each other across the left atrial wall. In this case, once again, the stronger atrial wall is used as the anchoring tissue, as opposed to the CS tissue only. When the magnets 118 in the CS 46 are brought together, as discussed above, an annular reduction of the mitral annulus 40 is achieved similar to the manner discussed above.

FIGS. 13A and 13B illustrate strips of magnets 118, 124 in the CS 46 and LA 12 as discussed previously. However, cinching via the CS 46 alone may not have sufficiently precise pull on the mitral annulus 40 since these two anatomical structures typically do not lie at the same level. Even the two strips of magnets 118, 124 shown in FIG. 12B are only coupled across the left atrial wall, and this may not be in line with the annulus 40 at all locations. Therefore, an additional magnet 126 shown in FIGS. 13A and 13B, fixed to a metal or otherwise substantially rigid curved bar 128, is placed under the mitral valve 20 in the LV 14, such that magnet 126 locks up with the strip of magnets 118 in the CS 46. This pulls the exterior annulus 40 toward the CS 46 and establishes a more coplanar relationship.

FIG. 14A illustrates a modification of the strip of magnets 124 positioned in the LA 12 such that there is an extension magnet 130 which is positioned at the midpoint of the strip of magnets 124. This extension magnet 130 extends down to the mitral valve annulus 40 bridging the gap between the CS 46 and the valve annulus 40. This may pull a magnet 132 and curved support bar 134 under the valve 20 tighter to the CS 46, as shown in FIG. 14B. It will be appreciated that magnet 132 and support bar 134 are similar to magnet 126 and support bar 128, except that bar 134 has a fabric covering 136 as may be desired for tissue ingrowth purposes. FIGS. 14C-14E illustrate the use of additional mechanical fasteners such as projections 138 on one or more of the magnets 132 used in the embodiments described above. This can apply additional traction or fastening to the tissue than could otherwise be supplied by the use of magnets alone.

FIGS. 15A-15E comprise a series of illustrations showing another alternative catheter based fastener delivery system. In addition to showing the use of a fastener 140 to pull the CS 46 into a more coplanar relationship with the annulus 40 (FIG. 15C), this system utilizes magnets 142, 144 which have orifices 142a, 144a through which the fastener 140 is delivered such that more precise placement of the fastener 140 may be obtained in certain instances while also using a magnetic lock up force for more positively driving the anchor or fastener 140. It will be appreciated that magnet 144 will be coupled to a catheter (not shown) for positioning within the CS 46. Magnet 142 may be releasably coupled to a steerable catheter 146. As shown in FIGS. 15D and 15E, after a plurality of magnets 142, 144 and fasteners 140 have been delivered such that tissue is trapped therebetween, a flexible tensile member 148 and crimps 150 may be used to cinch and lock the fasteners 140 together thereby pulling the posterior leaflet 24 toward the anterior leaflet 22 and closing a gap 32 in the valve 20.

FIGS. 16A-16E, as well as FIGS. 16A-1 and 16A-2 illustrate a system which is the same as the system shown in FIGS. 15A-15E, except that the magnets 142', 144' are formed of separable portions, such as halves 142a, 142b, 144a, 144b, so that the magnets 142', 144' may be removed after the fasteners 140' have been properly delivered. Thus, the anchors or fasteners 140' themselves have portions 140a, 140b which retain the fasteners 140' in place across the tissue proximate the annulus 40, and portions 140b accept a flexible tensile member 148 and crimps 150 for cinching and locking purposes as shown in FIGS. 16D and 16E generally in the manner or manners described herein. The separable magnet portions 142a, 142b and 144a, 144b may be coupled to suitable catheter devices allowing their release from fasteners 140' and withdrawal from the patient.

FIG. 17A illustrates an alternative fastener delivery system 160 using magnetic guidance in which the fastener 140' is not delivered through the magnets 162, 164, but is delivered adjacent to the magnets 162, 164 in a fastener driving portion 166 of a catheter 168. This is another manner of using magnetic guidance and temporary lock up without the necessity of leaving the magnets 162, 164 in place after completion of the procedure.

FIGS. 18A-18C illustrate a more conventional annuloplasty that may be accomplished using magnetic guidance and lock up in a temporary manner to facilitate fastener placement and driving. More specifically, a magnetic strip 170 is placed into the CS 46 using a catheter 172. A second magnetic strip 174 with a fabric covering 176 is placed in the left atrium 12 also via a catheter 178. Fasteners 180 are placed into the fabric 176 on the strip 174 in the left atrium 12 from the undersurface of the mitral valve 20 again using a catheter 82. Likewise, fasteners 180 are driven through the CS 46 and left atrium wall into the fabric 176 in a manner similar to that described with respect to, for example, FIGS. 3C and 3D through a catheter with a sideward firing fastener driving portion (see also FIGS. 7D-7F). The magnetic strips 170, 174 are removed from the fabric covering 176 and from the CS 46 and the fabric 176 is then drawstringed or cinched with a suitable flexible tensile member 184 coupled therewith to produce annuloplasty or pulling of the posterior leaflet 24 toward the anterior leaflet 22 to eliminate or reduce a gap 32 in the mitral valve 20.

FIGS. 19A-19C illustrate one alternative to a T-bar configuration of fasteners as previously described. In this embodiment, fasteners 190 in the form of anchor buttons 190a are placed below the mitral valve 20 along the annulus 40 using catheters 192, 194 with magnetic guidance and lock up as previously described. Although not shown, another catheter is used in the left atrium to deliver buttons 190b which couple with buttons 190a. Buttons 190a are further coupled to a flexible tensile member 196 which may be secured with crimps 200 (one shown in FIG. 19C) as previously described. This compresses the mitral tissue between respective tissue engaging portions of the buttons 190a, 190b. The buttons 190a, 190b are drawstringed or cinched from below using flexible tensile member 196 threaded through respective eyelet portions 198 of each button 190a.

FIGS. 20A and 20B illustrate another way to plicate the annulus 40 by using memory alloy staples 202 driven into the tissue along the annulus 40. When the memory alloy activates, the staples 202 shorten and plicate the tissue (FIG. 20B) to shorten the annulus 40 of the mitral valve 20 to pull the posterior leaflet toward the anterior leaflet as generally described above.

FIGS. 21A-21D illustrate the placement of fasteners 210 on the left atrial side of the mitral valve 20, daisy chained to pledgets or fasteners 212 in the form of tissue trapping load spreading members underneath the annulus 40. These fasteners 210, 212 are coupled together by a flexible tensile member 214 or drawstring, in this case. FIGS. 21A-21C illustrate a catheter 216 which delivers fasteners 210, 212 in a serial fashion along flexible tensile member 214 such that fasteners 210 are driven through the tissue and fasteners or pledgets 212 are released between each fastener 210. The series of fasteners 210, 212 is then drawn together using the drawstring or flexible tensile member 214 as shown in FIG. 21D. This shortens the distance between each of the fasteners 210, 212 and the entire structure with elements above and below the annulus 40. The tissue becomes trapped between the fasteners 210, 212 spreading loads over larger areas and reducing tear out risks.

FIG. 22 illustrates a modified version of the system illustrated in FIGS. 21A-21D. In this embodiment, after the first drawstring 214 is pulled to tighten the various fasteners 210, 212' and plicate the annulus 40 as generally shown in FIG. 21D, a second drawstring 218 coupled to eyelets 220 each of the pledgets 212' may be pulled for a secondary shortening operation which further reduces the annulus 40, as necessary.

FIGS. 23A-23E illustrate an alternative embodiment which is similar to FIGS. 21A-21D, except that the pledgets 212" have a pair of holes 222, 224 through which the flexible tensile member 214 or drawstring is threaded, as opposed to an eyelet structure.

FIGS. 24A-24C illustrate another embodiment of a catheter based fastener system 230 which employs a series of connected magnets 232, 234 with one series of magnets 232 lying in the CS 46 lying adjacent to the mitral valve annulus 40 and another series 234 lying in the LV 14 adjacent to the annulus 40. The magnets 232 residing in the CS 46 are coupled together by coil springs 236 and by a flexible tensile member 238, while the magnets 234 in the LV 14 are, in one embodiment, positioned individually in the LV adjacent to magnets in the CS 232, after release from the LV magnet delivery catheter 240, as shown in FIG. 24C. In another embodiment, the array of LV magnets 234 is shown in FIG. 24A adjacent to the CS magnets 232 and connected by a member consisting of a sheath 233 upon which the magnets 234 can slide. The array of magnets 234 and the sheath 233 are deposited in the LV 14 as the delivery catheter 240 is withdrawn. The connecting sheath 233 prevents the risk of an embolic accident resulting from a detachment of a single magnet 234. In FIG. 24B, the withdrawal of the LV delivery catheter 240 is shown in more detail. The most distal magnet 234 is shown attached to the sheath 233, whereas the next more proximal magnet 234 is still on the shaft of the delivery catheter 240. Each series of magnets 232, 234 is introduced into the positions shown in FIGS. 24A-24C by respective catheters 242, 240. A coupling 244 is provided and is releasably coupled to a pull wire or cable 246 in the catheter 242 such that the series of magnets 232 may be cinched or drawn together to reduce the circumferential length of the valve annulus 40. The LV magnets 234, owing to their attraction to their CS counterparts 232, are thus pulled together to accomplish plication of the dorsal cusp of the mitral valve 20 adjacent to the annulus 40. Plication may be better facilitated by features on the surface of the CS magnets 232 which grip the endocardial surface, and promote ultimate tissue ingrowth about the magnets 232 to strengthen the plication. Once the reduction has taken place, the magnets 232 are locked in place, and the catheter 242 is removed.

Figure 25A:
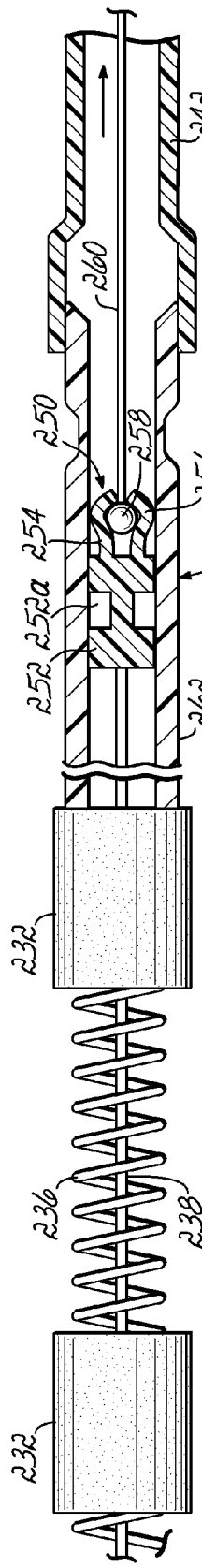
Figure 25B:
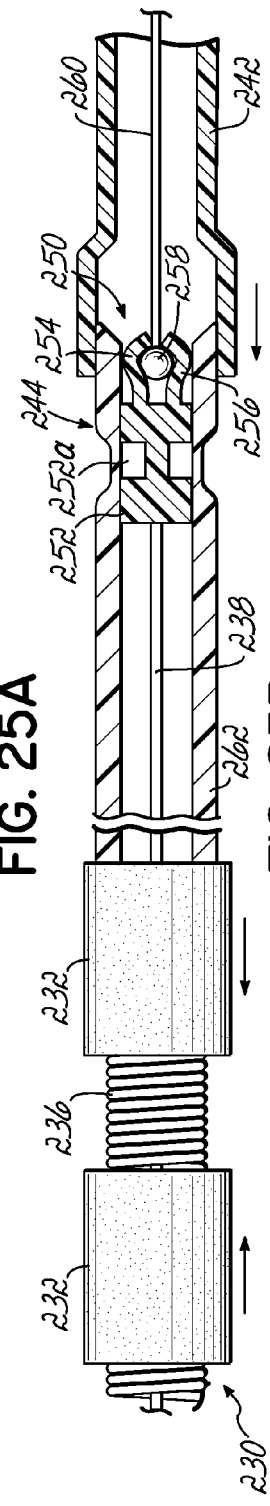
Figure 25C:
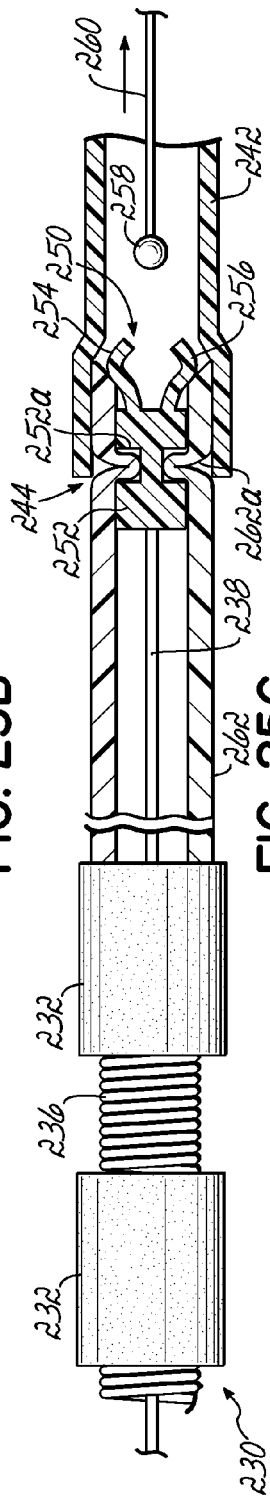
Figure 25D:
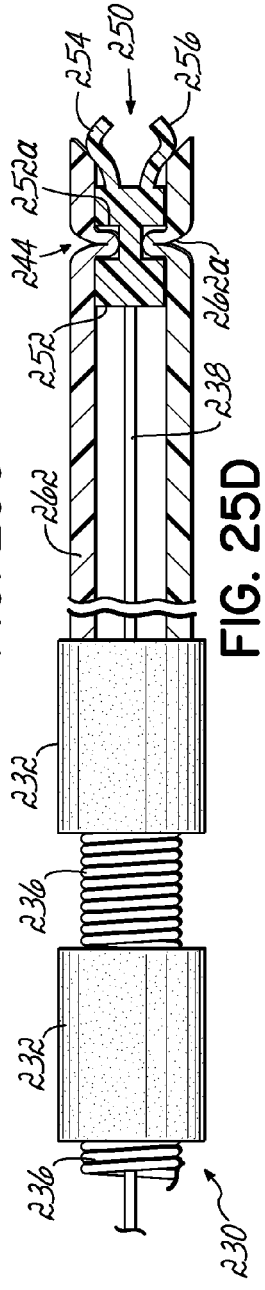

Referring more specifically to FIGS. 25A-25D, the operation of the coupling 244, and a release and locking mechanism 250 is shown. The initial position is shown in FIG. 25A in which the magnets 232 are spaced apart by the uncompressed coil springs 236 and the flexible tensile member 238 which is fixed to a coupling element 252 having at least a pair of arms 254, 256 which releasably grip a complimentary coupling element 258. The complimentary coupling element 258 is fixed to a pull wire or cable 260 extending within the delivery catheter 242. The wire or cable 260 is pulled as shown in FIG. 25B to compress the coil springs 236 and reduce the distance between each adjacent pair of magnets 232, thereby reducing the circumferential length of the annulus 40 (FIG. 24C) as the magnets 234 within the LV 14 passively follow the magnets 232 in the CS 46. At this point, the delivery catheter 242 may be pushed to the left as viewed in FIGS. 25B and 25C causing a crimping action of a tube 262 affixed to the most proximal magnet 232. A crimped portion 262a is then retained within a recessed portion of the coupling element 252. At the same time, the gripping arms 254, 256 release the complimentary coupling element 258 of the pull wire or cable 260 and the delivery catheter 242 and pull wire or cable 260 may then be removed leaving the locked fastener system 230 in place as shown in FIG. 25D.

FIGS. 26A-26C illustrate a fastener system 270 which operates the same as that disclosed in FIGS. 24A-24C and 25A-25D, except that an accordion or bellows type section 272 replaces each coil spring 236, and internally and externally threaded coupling elements 274, 276 replace the gripping arms 254, 256 and coupling element 258. It will be appreciated that the operation of the system shown in FIGS. 26A-26C is the same as that described in the previous embodiment, except that releasing the coupling element 276 will involve rotating the pull wire or cable 260 to decouple the threaded coupling elements 274, 276. It will be appreciated that the recessed portion 252a of coupling element 252 can have an essentially square cross section. The crimped portion 262a of tube 262 will thus engage the recessed portion and plastically deform about it to prevent rotation of coupling element 252 with respect to threaded coupling element 276. The coupling element 276 and cable can thus be effectively unthreaded and released.

FIGS. 27A and 27B illustrate another alternative catheter based fastener system 280 which is the same as those described with respect to the two previous embodiments, except that the coil springs 236 and accordion shaped bellows sections 272 have been replaced by respective telescoping portions 282, 284 which carry the magnets 232 fixed therein. Also, a releasable coupling 286 is formed by a quarter turn bayonet type fastener as opposed to the gripping arms 254, 256 and element 258, or the threaded connection 274, 276 of the two previous embodiments. In the present embodiment, an elastomeric pad 252b is seated distal to the proximal component of the bayonet connector 286. When the bayonet 286 is engaged in the delivery position, the pad 252b creates a load on the proximal component which prevents inadvertent release of the system 280. The recessed segment 252a of the coupling element can have a square cross section to prevent rotation of the coupling during disengagement of the bayonet, in a manner similar to the previous embodiment. The telescoping portions 282, 284 are flexible and also pivot so that they can conform to the curved shape of the CS 46. When the pull wire or cable 260 is pulled to the right as illustrated in FIGS. 27A and 27B, the telescoping portions 282, 284 can move together such that detents 288 move from one recess 290 to an adjacent recess 292 of the respective telescoping portions. The assembly is then locked in place as previously described and the bayonet coupling 286 is released for purposes of withdrawing the delivery catheter 242.

FIGS. 28A and 28B are illustrative of another embodiment which is the same as the system shown in FIGS. 27A and 27B, except that the telescoping portions 282', 284' are fabricated of a flexible, elastomeric polymer material to allow the fastener system 280' to conform to the curve of the CS 46 (FIG. 24C). This is to be contrasted with the fastener system 280 shown in FIGS. 27A and 27B, in which the telescoping elements 284 are fabricated of a relatively more rigid material. In this previous embodiment, flexibility is gained primarily from the length of the detents 290 and 292, which allow angled positioning of one telescoping element relative to an adjacent one. In the current embodiment, additional flexibility of the fastener is achieved with the length of the detents 290 and 292.

FIGS. 29A and 29B illustrate another system 280" which is similar to those described in the previous embodiment, except that the telescoping portions 282", 284" only have one recess location 290' for initially retaining the relative positions of the telescoping portions 282", 284" as shown in FIG. 29A. Also, each telescoping portion 282", 284" may have projections 296 which act as mechanical fasteners for engaging tissue within the CS 46 (FIG. 24C). When the telescoping portions 282", 284" are drawn together, as described above, the smaller diameter sections 282" are retained in the telescoped position by a locking mechanism operating on the flexible tensile member 238, such as previously described, thereby maintaining the shortened condition of the fastening system.

FIGS. 30, 31A and 31B illustrate another catheter based system 300 for placing magnets adjacent the mitral annulus, such as within the LV 14 (Fig. A). In this system, a delivery catheter 304 receives a plurality of annular magnets 306. Magnets 306, for example, may have roughened outer surfaces 306a for tissue engagement purposes. The catheter 304 has an outer diameter which is expandable to frictionally retain the magnets 306 at spaced apart locations. An internal tube 308 may be withdrawn, to the left as illustrated in FIG. 30, to release the magnets 306 from their frictional engagement with the outer surface of the delivery catheter 304. As one example, the delivery catheter 304 is shown with a manipulator wire 310 for orienting the direction of the distal tip 312, and also a core wire 314 for facilitating insertion and removal of the delivery catheter 304. Once the magnets 306 are magnetically coupled to additional magnets (not shown) across the annulus tissue, for example, the internal tube 308 may be withdrawn thereby releasing the delivery catheter 304 from magnets 306 and facilitating its removal by, for example, pulling on the core wire 314. The magnets 306 may be coupled together by a thin flexible sheath 316 or other suitable structure.

FIGS. 32A-32C illustrate another catheter based system of fasteners comprising a series of magnets 320 held for sliding movement along parallel wires 322, 324. Additional parallel wires 326, 328 are provided as guide wires to guide the assembly during insertion through a catheter (now shown) to a location adjacent the annulus. A suitable mechanism (not shown), is provided for pushing the magnets 320 together along wires 322, 324 to reduce annulus tissue, for example, with respect to additional movable magnets (not shown) on the opposite side of the tissue. The series of magnets 320 is locked in the position shown in FIG. 32B, for example. In this embodiment, magnets 320 are coated with a soft polymer 320a which frictional engages small stop members 322a, 324a on wires 322, 324 to assist with retaining desired positions of the magnets 322, 324.

FIGS. 33, 33A and 33B illustrate another system of fasteners placed via a delivery catheter 242 and including a coupling mechanism 244 and locking mechanism 250 as described above in connection with FIGS. 25A-25D. This system is similar to that described in FIGS. 26A and 26B in that bellows or crumple zones 330 are provided between magnets 232, as best illustrated in FIGS. 33A and 33B to accommodate movement of adjacent magnets 232 together as they slide along the flexible tensile member 238 while flexible tensile member 238, which is rigidly attached to the most distal magnet 232, is pulled to the left as viewed in FIG. 33. The operation of this embodiment is otherwise the same as that described in connection with FIGS. 26A and 26B.

Figure 34A:
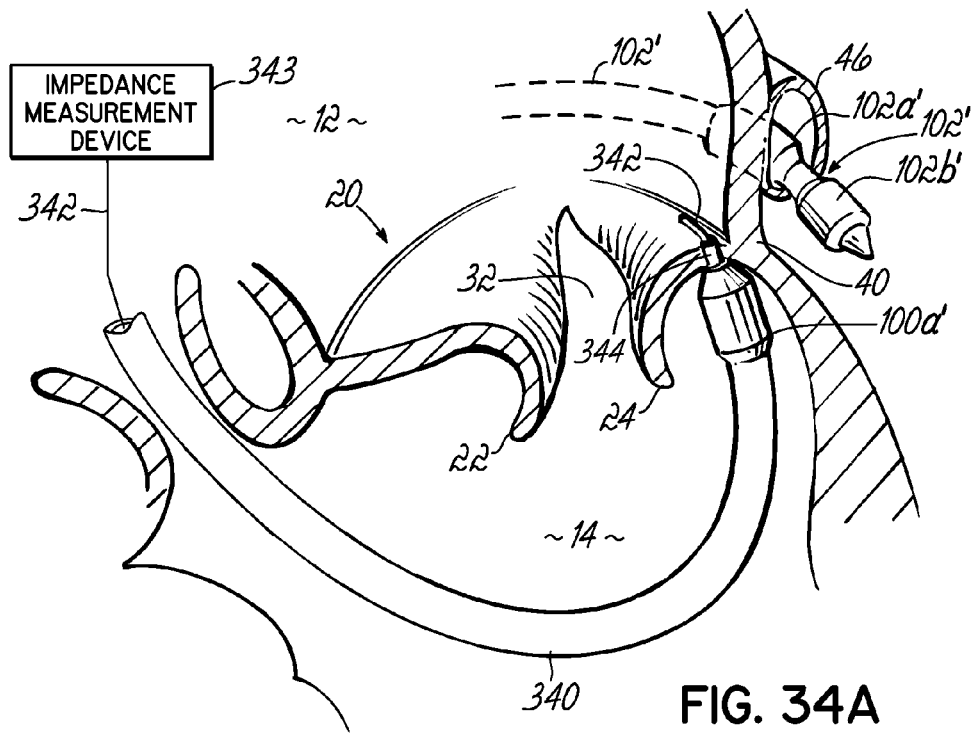
Figure 34B:
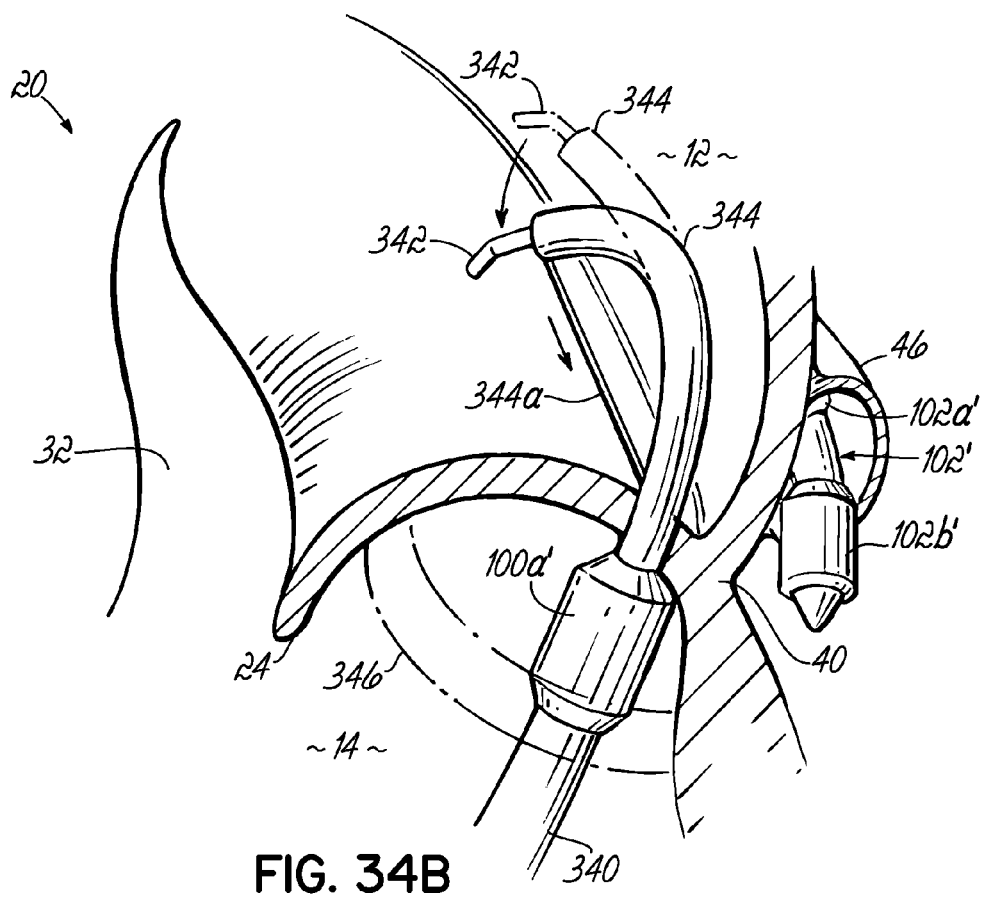
Figure 34C:
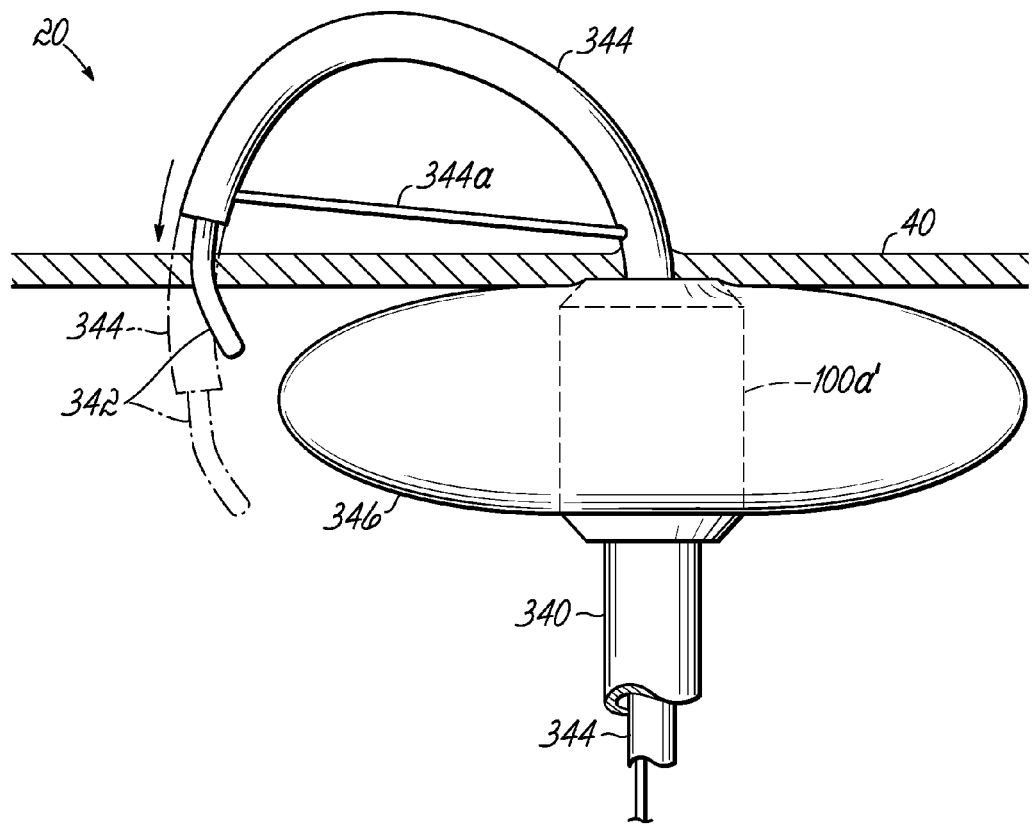
Figure 34D:
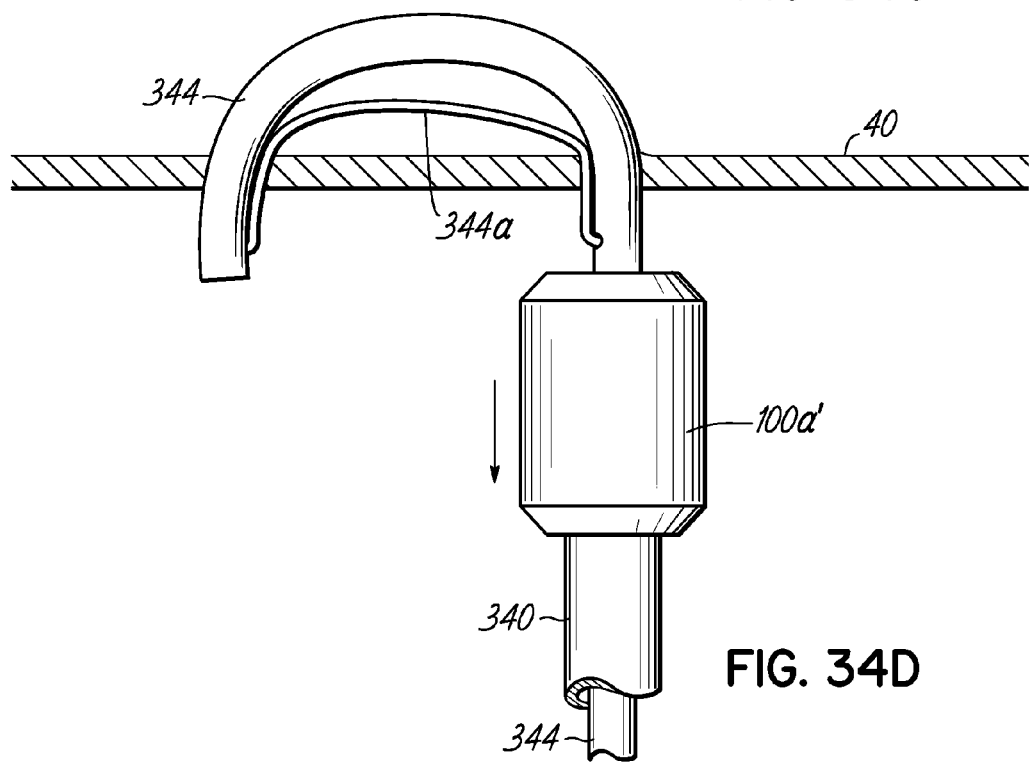

FIGS. 34A-34I comprise a series of illustrations of a catheter based system for applying a series of fasteners through tissue generally at the mitral valve annulus and using guidance magnets 102a', 102b' and 100a' (as previously described) in the CS 46 and the LV 14. In this embodiment, a left ventrical catheter 340 has a portion 342 which uses radio frequency (RF) to effectively drill an initial hole through the tissue and then insert a second larger diameter catheter portion 344 which is steerable, for example, as shown in FIGS. 34B-34D, to make a second hole in the annulus tissue 40. It will be appreciated that the various catheters disclosed herein may have distal portions which are steerable in various manners for accurate positioning purposes. In this embodiment, tip 344 is movable into a desired hook-like position by a guiding cable 344a which may be pulled to configure tip 344 into the hooked shape as shown. The catheters utilized herein can include unidirectional or bi-directional steering. A steering mechanism may be positioned within and/or on the devices. Typically, the steering mechanism may include a pull wire 344a terminating at a flat spring or collar. The steering system has a more flexible distal section compared to the proximal catheter tube body. When tension is placed on the pull wire 344a, the catheter distal end 344 is deflected into a curve, which helps direct the device within a heart chamber, for example. The pull wire 344a may be wound, crimped, spot welded or soldered to the flat spring or collar (not shown) placed in the catheter end 344. This provides a stable point within the device for the pull wire 344a to exert tensile force and thus steer the device. The more proximal portion of the catheter may be reinforced by incorporating a helically wound or braided wire therein to provide column support from which to better deflect the distal section 344. Alternatively, the steering mechanism may consist of a superelastic material having a desired three-dimensional geometric shape at its distal end and sufficient rigidity to impart this shape in the device. By retracting the preformed steering wire into the stiffer proximal section of the device, the distal end of the device straightens. Extending the preformed steering wire into the more flexible distal section of the device causes the distal section to assume the shape of the steering wire. Alternatively, a device with a curved section can incorporate a tube or rod that can be advanced through that section to straighten it. An additional feature that may be incorporated in the device is a preformed shape in the distal section of the device. The distal section may be preformed into a curve that biases the device to maximize tissue contact when the device is positioned into the appropriate heart chamber. This curve may consist of a single arc or a nonlinear geometry, such as an "S". A pre-shaped rod, hypotube, wire or coil, created from a memory elastic material such as nickel titanium or spring steel may be thermally formed into the desired geometry, and inserted into the distal section (including a separate lumen) of the device during manufacturing or advanced through a dedicated lumen while the device is positioned in the heart. The shaped wire may be attached to the distal tip of the device for those non-removable pre-shaped rods and secured to the handle of the device at its proximal end to provide a reinforcing structure throughout the entire length of the device. The device body may also or alternatively be thermally formed into a desired geometry.

As shown in FIG. 34A, the various systems of this invention may also include different manners of ensuring that the catheter device(s) is/are properly position adjacent to tissue prior to use. For example, an impedance measurement device 343 may be coupled to the perforating element itself, such as RF wire 342, or electrodes on the perforating element or on any separate element carried by the system. Such proximity determining devices may be used to confirm contact between the catheter device and the tissue surface by comparing the impedance between the electrode (such as RF wire 342) and a return path (indifferent patch electrode or second element electrode). When the electrode(s) only contact blood, the impedance is substantially higher than when the electrode element is in contact with the tissue surface. Each electrode is connected to a signal wire, with the signal wire connected to impedance measurement device 343. The signal wire may be connected to the impedance measurement device 343 by way of a connector and cable system. The measurement device 343 may be a power supply, a simple electrical resistance meter, or any other suitable device and method of use.

Figure 34E:
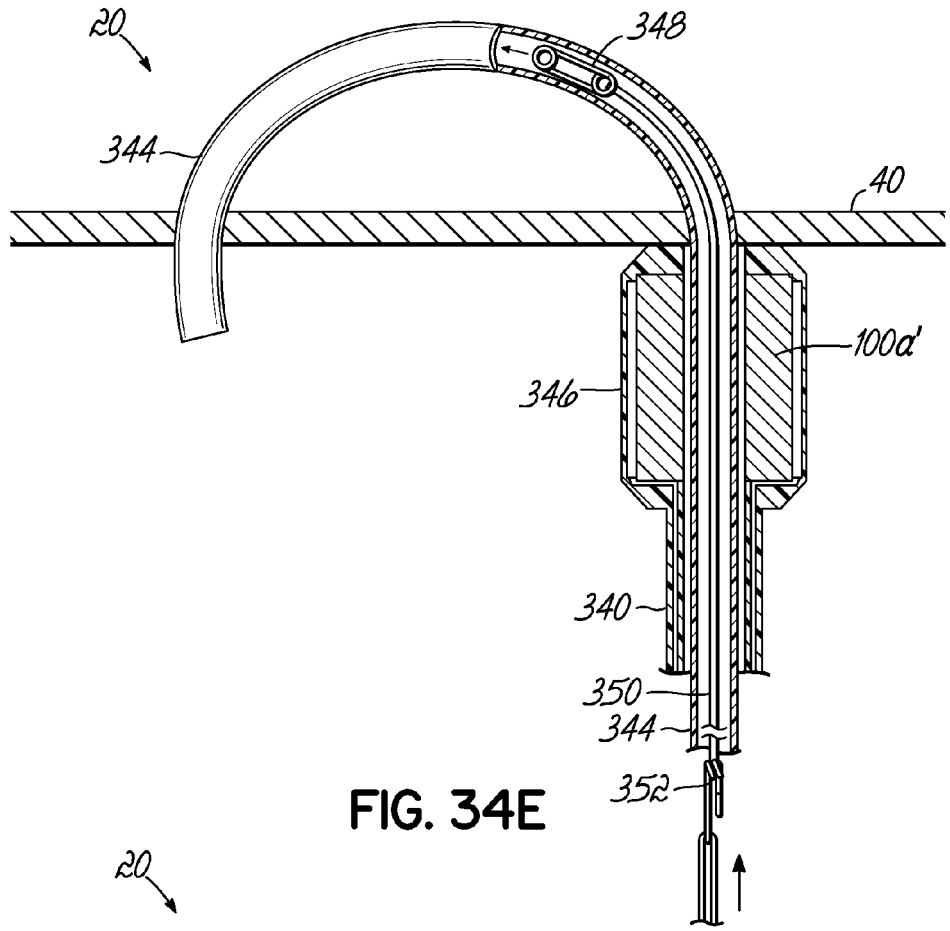
Figure 34F:
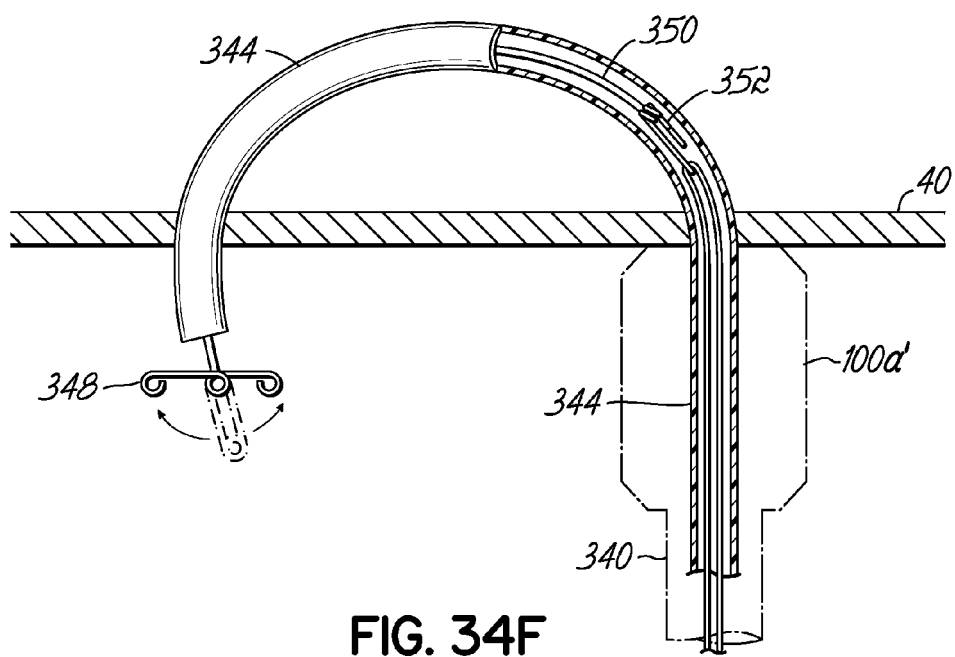
Figure 34G:
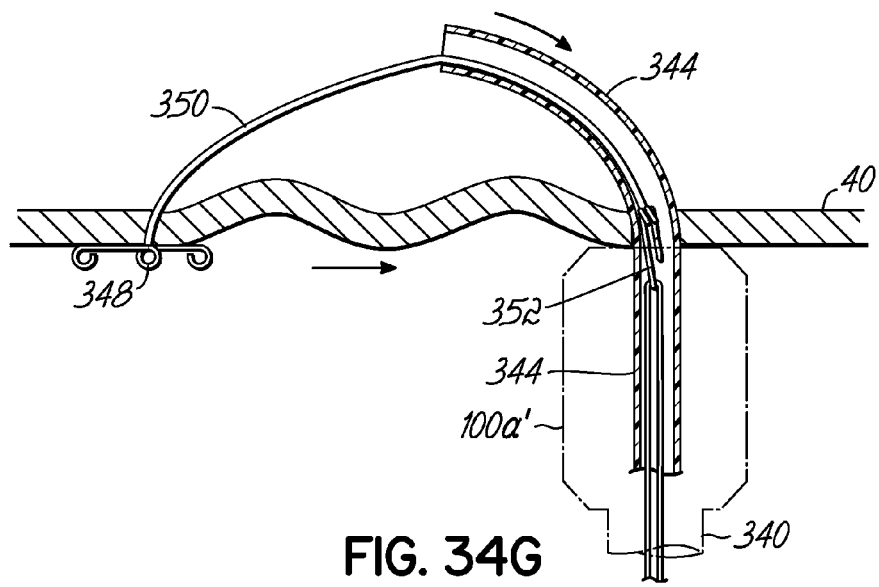
Figure 34H:
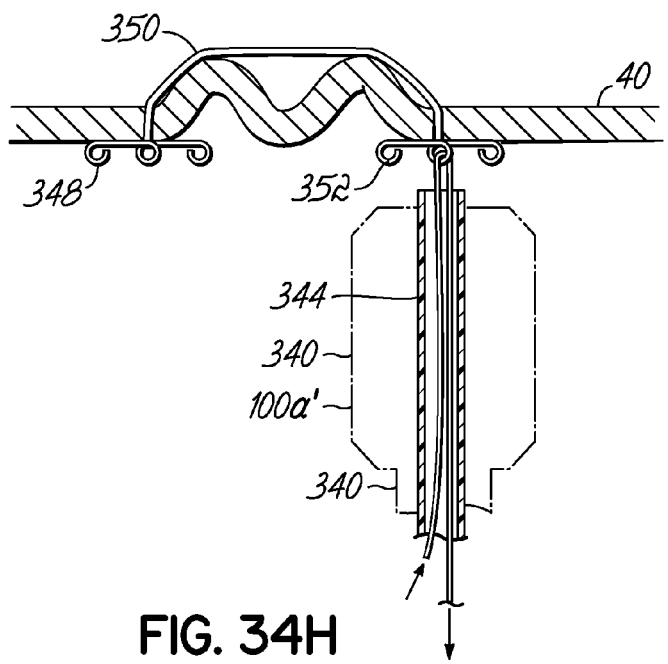
Figure 34I:
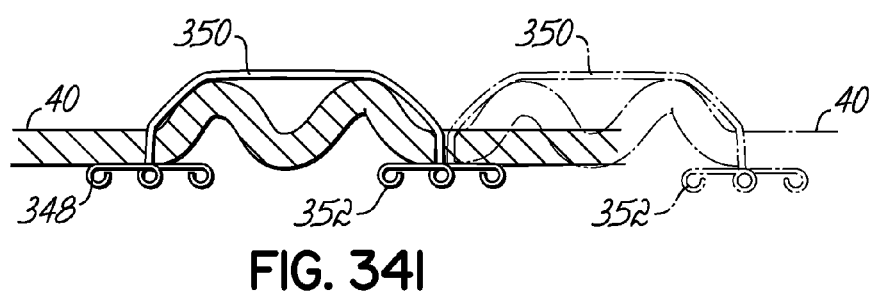

As further illustrated in FIG. 34C, a balloon portion 346 of the left ventricle catheter 340 may be inflated to stabilize the catheter 340 against the tissue 40 as the holes are being formed. As shown in FIGS. 34E and 34F, a fastener 348 is delivered through the lumen of the steerable catheter portion 344 and is coupled with a flexible tensile member 350 and another fastener 352. The first and second fasteners 348, 352 are deployed on the same side of the tissue 40 at spaced apart locations with the flexible tensile member 350 coupled therebetween. These fasteners 348, 352 may be formed essentially as torsion spring members which may have a portion which captures and locks against the flexible tensile member 350 in the deployed position as shown in FIG. 34F. Once the first fastener 348 is deployed as shown in FIG. 34G, the flexible tensile member 350 may be pulled to plicate the tissue 40 between the first fastener 348 and the steerable catheter portion 344. At this time, the second fastener 352 is delivered and captures and locks with the flexible tensile member 350 to lock the length of the flexible tensile member 350 between the two fasteners 348, 350 with the tissue plicated as shown in FIG. 34H. This process may be repeated, as necessary, to plicate additional annulus tissue 40 for further annulus reduction.

FIGS. 35A-35F illustrate another catheter device 360 for delivering multiple fasteners 362 attached with a flexible tensile member 364, for example, in the LV 14 at the annulus 40. As best shown in FIG. 35B, the catheter device 360 includes three fastener delivery portions 366, 368, 370. One portion 368 is a central portion at the distal end of the catheter device 360 and deploys a first fastener 362. Two additional fastener delivery portions 366, 370 are spaced on opposite sides of the central portion 368 and preferably may be actively moved to preferred positions relative to central portion 368 to deliver additional fasteners 362. A flexible tensile member 364 couples each fastener 362 together as well as to a plurality of pledgets or tissue support members 372. A fastener drive mechanism 374 is used to drive one or more of the fasteners 362 through the tissue and comprises a reciprocating rod 376 which is activated by spring force developed in a coil spring 378. When a pair of magnets 380, 382 are decoupled by pulling a wire or cable 384, for example, the spring forces the reciprocating rod 376 upwardly as viewed in FIG. 35B to drive the fastener 362 through the tissue 40. It will be appreciated that similar mechanisms may be used with flexible drive rods 386, 388 in driving the outer fasteners 362 through the tissue, or this same mechanism 374 may be coupled with flexible drive rods 386, 388 to simultaneously drive each of the fasteners 362 through the tissue 40. All three fasteners 362 are thereby deployed, in addition to the pledgets 372, as illustrated in FIG. 35E. Then, the drawstring or flexible tensile member 364 are pulled tight to plicate the tissue 40 as shown in FIG. 35F and a crimp member 390 is applied to lock the flexible tensile member 364 in the tensioned position to retain the plicated tissue 40 in the desired state.

FIG. 36 illustrates an alternative embodiment of the catheter device 360 shown in FIG. 35A-35F, in which the distal end of the catheter device 360' includes a magnet 400 for locking up temporarily with one or more magnets (not shown) in the CS 46 (Fig. A) as previously described. This allows the catheter device 360' to be accurately positioned and temporarily locked in place proximate the annulus 40 while the anchors or fasteners 362 are being delivered, cinched and locked in place as previously described with respect to FIGS. 35A-35F.

FIGS. 37A-37C illustrate another alternative catheter delivery device or system 410, and valve support/fastener system 412 for plicating annulus tissue 40 and pulling a posterior leaflet 24 toward an anterior leaflet 22. In this embodiment, a C-shaped support member 414 is initially retained within a catheter 416 in a nonactivated, compact state as shown in FIG. 37A. When the support member 414 is pushed from the distal end of the catheter 416, it springs into a deployed or activated state as shown in FIGS. 37B and 37C. The anchors or fasteners 418 are retained on the rod shaped support member 414 for sliding movement and are coupled together by one or more flexible tensile members 420. An additional flexible tensile member 422 extends from another catheter portion 424 and provides for secondary cinching or drawstring action. A magnet 426 is rigidly coupled to a central fastener or anchor 418 at P2, as shown, or otherwise coupled to the support rod 414 and temporarily locks up with a magnet 428 in the CS 46 generally as previously described. Fasteners or anchors 418 are then connected to the annulus tissue 40 such as by using additional fastening elements (not shown) which are delivered via another catheter (not shown) within the LV 14, in one of the manner previously described. Once the anchors or fasteners 418 are secured to the tissue 40, the flexible tensile members 420 are pulled thereby pulling each of the fasteners or anchors 418 toward one another along the support member 414. A final or secondary pulling action may be obtained by pulling the flexible tensile member ends 422 extending into the catheter portion 424 extending from the main catheter 416. Various manners may be used to retain the flexible tensile members 420, 422 and anchors 418 at the new positions shown in FIG. 37C, such as by using crimp members (not shown), or integrated ratchet-type or frictional engagement structure (not shown) which automatically locks the flexible tensile members 420, 422 in place as they are pulled.

Figure 38A:
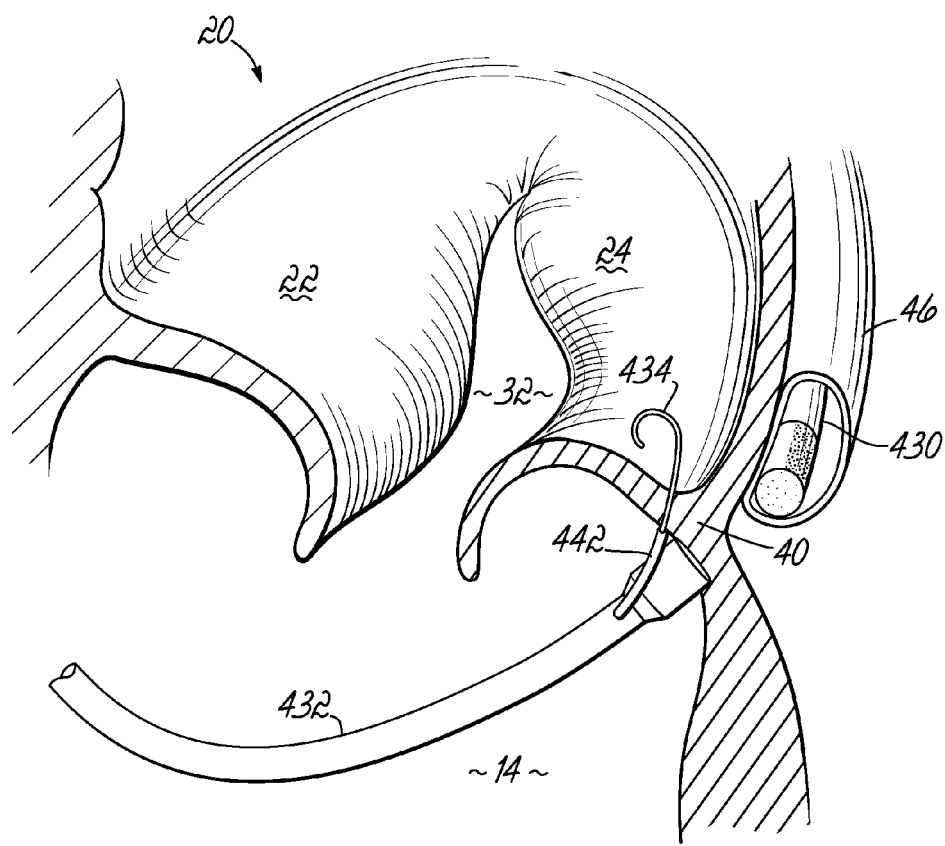
Figures 38B, 38C:
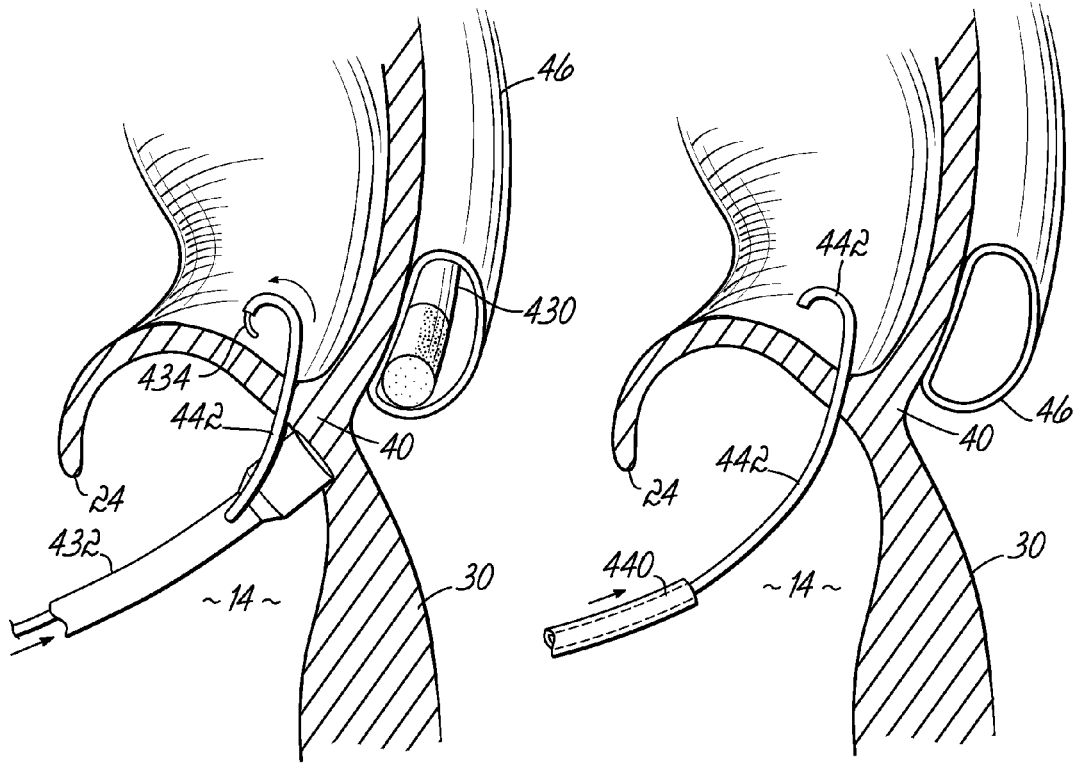
Figures 38D, 38E:
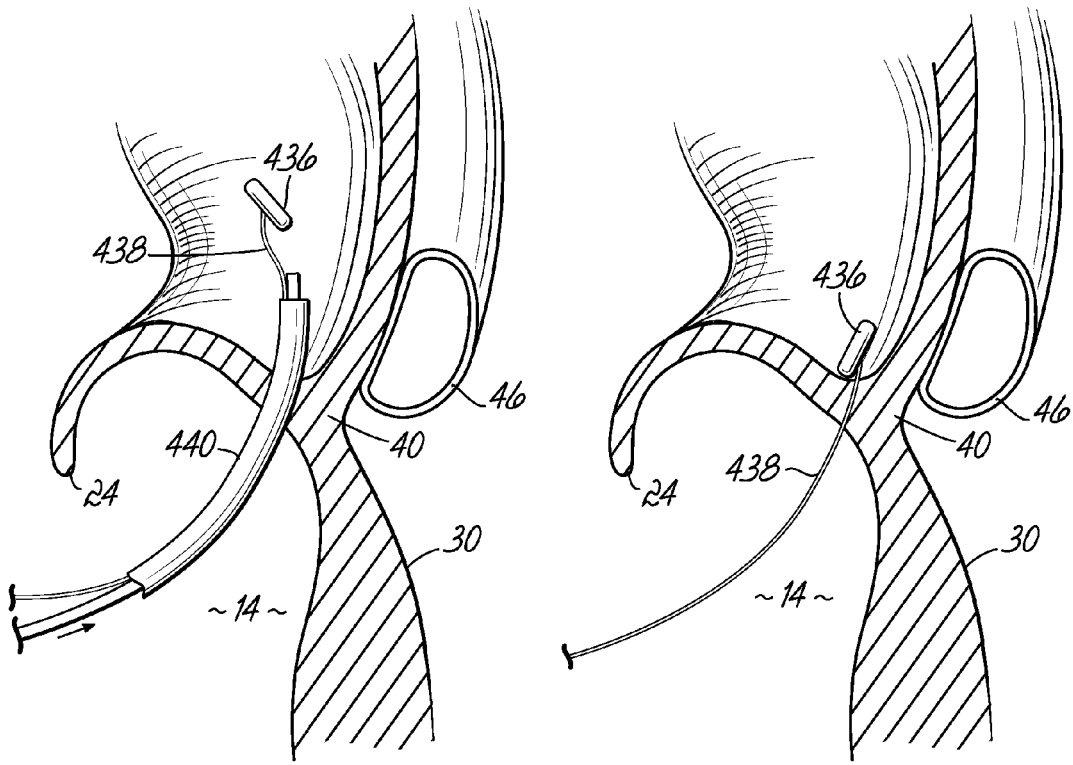
Figure 38F:
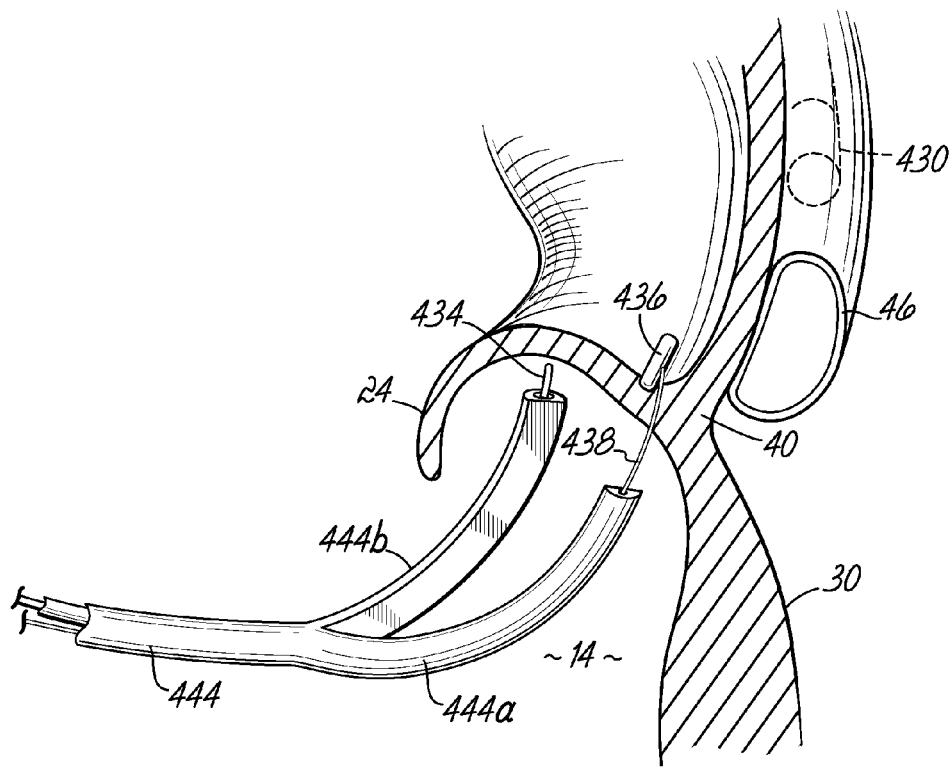
Figure 38G:
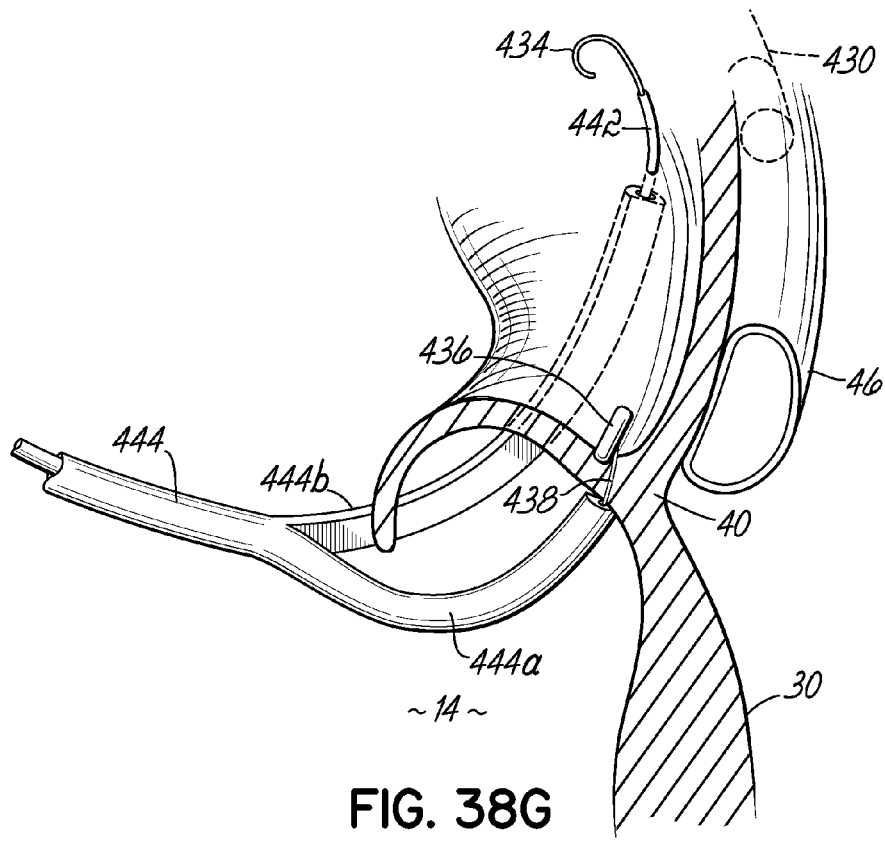
Figure 38H:
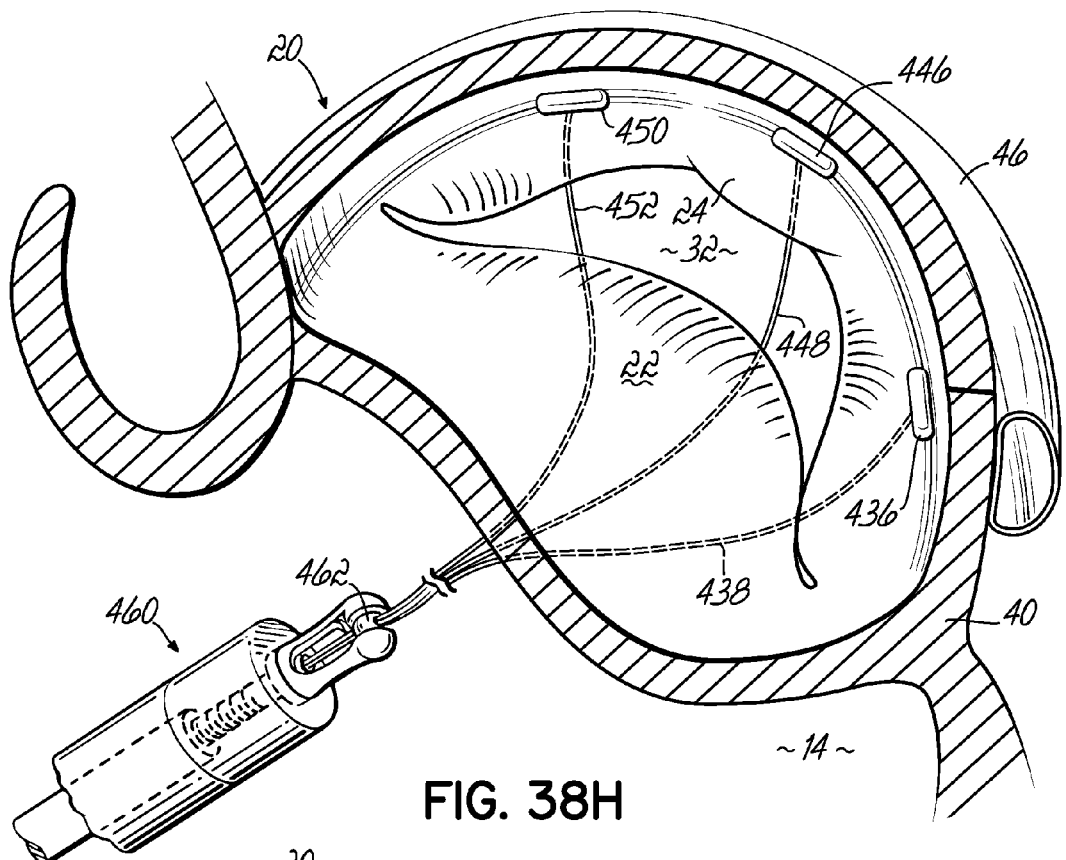
Figure 38I:
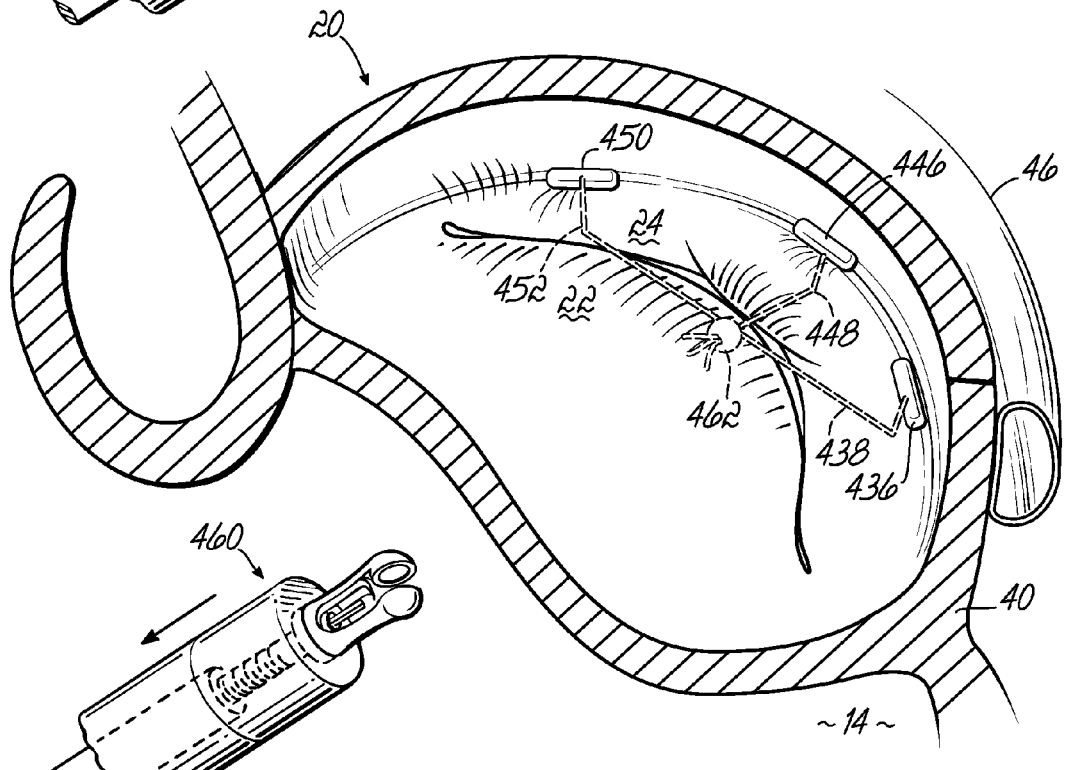

FIGS. 38A-38I illustrate another catheter based system and method for delivering, for example, three fasteners or anchors coupled to respective flexible tensile members and cinched together to reduce a mitral valve annulus 40. In this embodiment, as shown in FIG. 38A, a CS catheter 430 and LV catheter 432 may temporarily lock up through magnetic coupling and an initial hole may be formed through the annulus tissue 40 using RF energy applied via a wire 434. A first fastener or anchor 436 coupled with a flexible tensile member 438 may be deployed through the hole using a catheter 440 threaded over a guide tube 442. The catheter 440 may be removed and another catheter 444 having bifurcated portions 444a, 444b may be used by threading one of the bifurcated portions 444a over the flexible tensile member 438. Alternatively, once the first fastener 436 and flexible tensile member 438 are deployed as shown in FIG. 38F, the second portion 444b of the catheter 440 may be activated and moved to a spaced apart location to form a hole using an RF wire 434 and then deploy a second fastener 446 and flexible tensile member 448 (FIG. 38H). Then, the first catheter portion 444a and second catheter portion 444b are removed and the first catheter portion 444a is threaded along the second flexible tensile member 448. A third anchor 450 and attached flexible tensile member 452 are then deployed from the second catheter portion 444b resulting in three deployed anchors 436, 446, 450 and flexible tensile members 438, 448, 452 as shown in FIG. 38H. A crimping and cutting device 460 is then used to pull the flexible tensile members 438, 448, 452 and fasteners or anchors 436, 446, 450 together to thereby pull the posterior leaflet 24 toward the anterior leaflet 22 and then a crimp member 462 is applied to the flexible tensile members 438, 448, 452 and cut to result in the system being fastened generally as shown in FIG. 38I. As alternatives to RF energy, other manners and devices may be used for forming a hole through tissue prior to or while inserting an anchor or fastener. For example, these may include needles, blades, coring devices, etc. which can effectively create a starter hole in the tissue such that less force is required to drive an anchor into or through the tissue.

As shown in FIGS. 39A and 39B, the crimping and cutting device 460 includes a crimping portion 470 comprising jaws 472a, 472b with projections 472 for applying force to the crimp member 462 and a cutting portion 474 coupled with an RF energy source 476. After the crimping portion 470 is actuated to crimp the crimp member 462 onto the flexible tensile members 438, 448, 452, the RF energy source 476 is activated to cut the flexible tensile members 438, 448, 452 as shown in FIG. 39B using cutting element a 477. To facilitate crimping, one threaded portion 478 of the device is rotated with respect to another portion 479. This pulls jaws 472a, 472b proximally to bring them together against the crimp member 462.

FIG. 40 illustrates the use of an additional magnet 480 in the left atrium 12 for supplying additional magnetic force at the junction of the annulus 40 and CS 46. An arrangement of magnets 480, 482, 484 may be used for temporarily locking up the catheter system at the location that it is desired to deliver a fastener or anchor (not shown), such as in those manners previously described. FIGS. 40B-40D illustrate an alternative fastener delivery system and method for delivering fasteners 486 in the left atrium 12 as opposed to the left ventricle 14 as previously described. This system is otherwise similar in that magnetic guidance and lock up first temporarily occurs between the various magnets 480, 482, 484 in the system. Once this magnetic lock up has taken place, a fastener 486 and flexible tensile member 488 may be delivered through a steerable portion 490a of a catheter 490 in the left atrium 12 such that the fastener 486 is delivered into the left ventricle 14. Steering mechanisms, such as those described elsewhere herein may be used to accurately direct catheter portion 490a. A number of fasteners 486 and attached flexible tensile member or members 488 may be deployed as shown in FIG. 40D and then cinched or drawn together using a crimping and cutting device 460 as previously described.

FIGS. 41A-41C illustrate another embodiment of a catheter delivered fastening system. In this embodiment, it will be understood that a series of fasteners 500, 502, 504 and attached flexible tensile members 506, 508, 510 may be delivered as previously described and as shown in FIGS. 41A and 41B. A delivery catheter 520 may include a balloon 522 for stabilizing against the tissue 40 and/or for positioning respective arms 520a, 520b, 520c of the catheter device 520 while delivering the anchors or fasteners 500, 502, 504 and each of their attached flexible tensile members 506, 508, 510. A valve support member 530 may then be delivered through a catheter (not shown) as shown in FIG. 41B. The support member 530 has eyelets 532, 534, 536 which are threaded over each of the respective flexible tensile members 506, 508, 510. Respective crimps 538, 540 are applied to the outer eyelets 532, 536 and the flexible tensile members 506, 510 cut proximate to each crimp member 538, 540. The central flexible tensile member 508 is pulled to thereby pull the posterior leaflet 24 at P2 toward the anterior leaflet 22. When suitable tension and pulling action has taken place, a third crimp member 542 is applied proximate the central eyelet 534 at the apex of the V-shaped and the flexible tensile member 508 is cut proximate to the crimp member 542. This results in approximation of the posterior and anterior leaflets 22, 24 as shown in FIG. 41C.

FIGS. 42A and 42B illustrate one possible anchor or fastener 550 usable with the various systems of the present invention. Such an anchor 550 may be rigidly coupled to a flexible tensile member 552, or coupled such that the anchor or fastener 550 slides along the flexible tensile member 552, as necessitated by the fastening system in which the fastener 550 is being used.

FIG. 43 is a side elevational view of an alternative fastener 560 which is similar to that shown in FIGS. 42A and 42B, except that the fastener 560 has a curved outer profile. The convex surface 562 of the curved outer profile is adapted to engage tissue and cause less trauma to the tissue than the flat profile shown in FIGS. 42A and 42B.

FIGS. 44A-44C illustrate another alternative fastener 570 useful in the various systems and methods of this invention. This fastener 570 includes two radially expandable portions 572, 574 which may be delivered through a catheter 576 in their nonexpanded state shown in FIG. 44A, and then expanded on opposite sides of the tissue 40 to be trapped therebetween, as shown in FIGS. 44B and 44C.

While the present invention has been illustrated by a description of various preferred embodiments and while these embodiments has been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known.

What is claimed is:

1. A method of modifying the spatial relationship between a coronary sinus and an annulus of a mitral valve, the coronary sinus lying at least partially apart from the annulus at least at one location, comprising:
   applying a fastener through the annulus and into the coronary sinus;
   temporarily anchoring the coronary sinus to the annulus at least at the one location while applying the fastener; and
   using at least the applied fastener to bring the coronary sinus closer to the annulus at least at the one location.

2. The method of claim 1, wherein using at least the applied fastener to bring the coronary sinus closer to the annulus further comprises: moving the coronary sinus downwardly to a position adjacent the annulus at least at the one location.

3. The method of claim 1, wherein temporarily anchoring the coronary sinus to the annulus further comprises moving the coronary sinus and annulus together with magnetic elements at least at the one location.

4. The method of claim 1, further comprising: modifying the annulus so as to reduce regurgitation of blood through the mitral valve.

5. The method of claim 4, wherein modifying the annulus further comprises:
   plicating the annulus with fasteners.

6. The method of claim 4, wherein modifying the annulus further comprises: moving the posterior and anterior sides of the annulus closer together, and fixing the annulus such that the posterior and anterior sides remain closer together.

7. The method of claim 4, wherein modifying the annulus further comprises: placing anchors in the coronary sinus, and cinching the anchors together.

8. A method of modifying the annulus of a mitral valve, wherein a coronary sinus is positioned proximate to the annulus at least at one location, the method comprising:
   applying a fastener through the annulus and into the coronary sinus;
   temporarily anchoring the coronary sinus to the annulus at least at the one location while applying the fastener; and
   modifying the annulus so as to reduce regurgitation of blood through the mitral valve using at least the applied fastener.

9. The method of claim 8, wherein temporarily anchoring the coronary sinus to the annulus further comprises moving the coronary sinus and annulus together with magnetic elements at least at the one location.

10. The method of claim 8, wherein modifying the annulus further comprises: plicating the annulus with fasteners.

11. The method of claim 8, wherein modifying the annulus further comprises: moving the posterior and anterior sides of the annulus closer together, and fixing the annulus such that the posterior and anterior sides remain closer together.

12. The method of claim 8, wherein modifying the annulus further comprises: placing anchors in the coronary sinus, and cinching the anchors together.

* * * * *